United States Patent
Utsunomiya et al.

(10) Patent No.: US 9,700,242 B2
(45) Date of Patent: Jul. 11, 2017

(54) MOTION INFORMATION PROCESSING APPARATUS AND METHOD

(71) Applicant: TOSHIBA MEDICAL SYSTEMS CORPORATION, Otawara-Shi (JP)

(72) Inventors: Kazuki Utsunomiya, Nasushiobara (JP); Kousuke Sakaue, Nasushiobara (JP); Satoshi Ikeda, Yaita (JP); Yoshihisa Yoshioka, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 34 days.

(21) Appl. No.: 14/801,516

(22) Filed: Jul. 16, 2015

(65) Prior Publication Data

US 2015/0325004 A1  Nov. 12, 2015

Related U.S. Application Data

(63) Continuation of application No. PCT/JP2014/051016, filed on Jan. 20, 2014.

(30) Foreign Application Priority Data

Jan. 18, 2013 (JP) ................................ 2013-006826
Jan. 22, 2013 (JP) ................................ 2013-009648
Jul. 25, 2013 (JP) ................................ 2013-154926

(51) Int. Cl.
*G06K 9/00* (2006.01)
*A61B 5/11* (2006.01)
(Continued)

(52) U.S. Cl.
CPC .......... *A61B 5/1127* (2013.01); *A61B 5/1071* (2013.01); *A61B 5/1121* (2013.01);
(Continued)

(58) Field of Classification Search
CPC ................ G06K 9/00; G06T 7/00; A61B 5/00
(Continued)

(56) References Cited

U.S. PATENT DOCUMENTS 7,254,253 B2 * 8/2007 Higaki ............... G06K 9/00335
                                                           382/103
9,327,399 B2 * 5/2016 Doi ....................... B62D 57/032
2013/0090574 A1 * 4/2013 Kuribayashi ......... A61B 5/1116
                                                           600/595

FOREIGN PATENT DOCUMENTS

JP  09-056697 A  3/1997
JP  2004-089355 A  3/2004
(Continued)

OTHER PUBLICATIONS

International Search Report mailed Apr. 28, 2014 for PCT/JP2014/051016 filed Jan. 20, 2014 with English Translation.
(Continued)

*Primary Examiner* — Abolfazl Tabatabai
(74) *Attorney, Agent, or Firm* — Oblon, McClelland, Maier & Neustadt, L.L.P.

(57) ABSTRACT

A motion information processing apparatus of an embodiment includes processing circuitry. The processing circuitry obtains motion information of an object person who executes a walking motion. The processing circuitry generates track information, which indicates a position of a landing point of a foot of the object person and a movement of the object person, based on the motion information obtained. The processing circuitry performs control in such a manner that the track information generated is displayed on a display.

32 Claims, 59 Drawing Sheets

(51) Int. Cl.
*A61B 5/00* (2006.01)
*A61B 5/107* (2006.01)
*G06T 7/246* (2017.01)
*H04N 3/36* (2006.01)

(52) U.S. Cl.
CPC ............ *A61B 5/1122* (2013.01); *A61B 5/742* (2013.01); *G06K 9/00348* (2013.01); *G06K 9/00369* (2013.01); *G06T 7/251* (2017.01); *A61B 2505/09* (2013.01); *G06T 2207/10016* (2013.01); *G06T 2207/10024* (2013.01); *G06T 2207/10028* (2013.01); *G06T 2207/30196* (2013.01); *G06T 2207/30241* (2013.01)

(58) Field of Classification Search
USPC ......... 382/103, 107, 236; 348/14.1, 97, 154, 348/155, 169, 208.1, 407.1, 352
See application file for complete search history.

(56) References Cited

FOREIGN PATENT DOCUMENTS

| | | |
|---|---|---|
| JP | 2010-172394 A | 8/2010 |
| JP | 2011-251013 A | 12/2011 |
| WO | WO 2005/096939 A1 | 10/2005 |
| WO | WO 2007/052631 A1 | 5/2007 |

OTHER PUBLICATIONS

International Written Opinion mailed Apr. 28, 2014 for PCT/JP2014/051016 filed Jan. 20, 2014.

* cited by examiner

FIG.3

| JOINT IDENTIFICATION INFORMATION | COORDINATE INFORMATION |
|---|---|
| 2a | (x1,y1,z1) |
| 2b | (x2,y2,z2) |
| 2c | (x3,y3,z3) |
| 2d | (x4,y4,z4) |
| 2e | (x5,y5,z5) |
| 2f | (x6,y6,z6) |
| 2g | (x7,y7,z7) |
| 2h | (x8,y8,z8) |
| 2i | (x9,y9,z9) |
| 2j | (x10,y10,z10) |
| 2k | (x11,y11,z11) |
| 2l | (x12,y12,z12) |
| 2m | (x13,y13,z13) |
| 2n | (x14,y14,z14) |
| 2o | (x15,y15,z15) |
| 2p | (x16,y16,z16) |
| 2q | (x17,y17,z17) |
| 2r | (x18,y18,z18) |
| 2s | (x19,y19,z19) |
| 2t | (x20,y20,z20) |

FIG.5

| NAME | NAME NUMBER | PERFORMANCE DATE | MOTION INFORMATION ||||
|------|-------------|------------------|-------------|---------|---------|---------|
| | | | COLOR IMAGE INFORMATION | DISTANCE IMAGE INFORMATION | SOUND RECOG-NITION RESULT | SKELETON INFORMATION |
| A | 1 | 20120801_1 | COLOR IMAGE INFORMATION | DISTANCE IMAGE INFORMATION | SOUND RECOG-NITION RESULT | SKELETON INFORMATION |
| | | 20120801_2 | COLOR IMAGE INFORMATION | DISTANCE IMAGE INFORMATION | SOUND RECOG-NITION RESULT | SKELETON INFORMATION |
| | | 20120802_1 | COLOR IMAGE INFORMATION | DISTANCE IMAGE INFORMATION | SOUND RECOG-NITION RESULT | SKELETON INFORMATION |
| | | . | . | . | . | . |
| | | . | . | . | . | . |
| B | 2 | 20120803_1 | COLOR IMAGE INFORMATION | DISTANCE IMAGE INFORMATION | SOUND RECOG-NITION RESULT | SKELETON INFORMATION |
| | | 20120804_1 | COLOR IMAGE INFORMATION | DISTANCE IMAGE INFORMATION | SOUND RECOG-NITION RESULT | SKELETON INFORMATION |
| | | 20120805_1 | COLOR IMAGE INFORMATION | DISTANCE IMAGE INFORMATION | SOUND RECOG-NITION RESULT | SKELETON INFORMATION |
| | | . | . | . | . | . |
| | | . | . | . | . | . |
| . | . | . | . | . | . | . |

FIG.6

| NAME | NAME NUMBER | PERFORMANCE DATE | ANALYSIS INFORMATION ||||||||||
|---|---|---|---|---|---|---|---|---|---|---|---|---|
| | | | LANDING POINT OF FOOT | ANGLE | VELOCITY | ACCELERATION | NUMBER OF STEPS | STRIDE | OVERLAPPED WALKING DISTANCE | STEP INTERVAL | WALKING RATE | . |
| A | 1 | 20120801_1 | . | . | . | . | . | . | . | . | . | . |
| | | 20120801_2 | . | . | . | . | . | . | . | . | . | . |
| | | 20120802_1 | . | . | . | . | . | . | . | . | . | . |
| | | . | | | | | | | | | | |
| | | . | | | | | | | | | | |
| B | 2 | 20120803_1 | . | . | . | . | . | . | . | . | . | . |
| | | 20120804_1 | . | . | . | . | . | . | . | . | . | . |
| | | 20120805_1 | . | . | . | . | . | . | . | . | . | . |
| | | . | | | | | | | | | | |
| | | . | | | | | | | | | | |
| . | . | . | | | | | | | | | | |

FIG.9
(A)
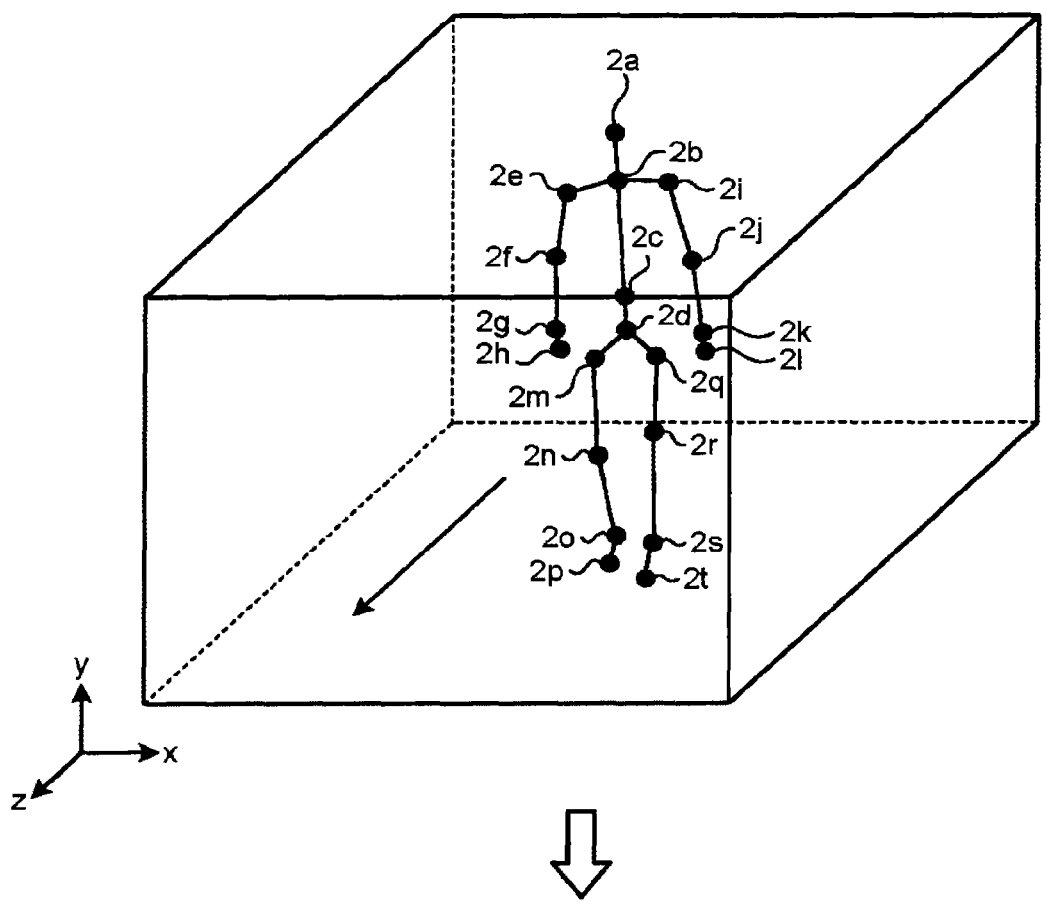
(B)
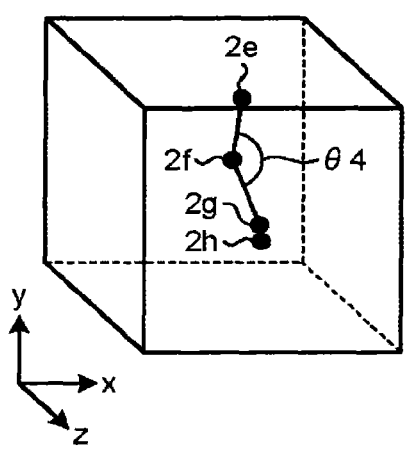

FIG.12A
(A)
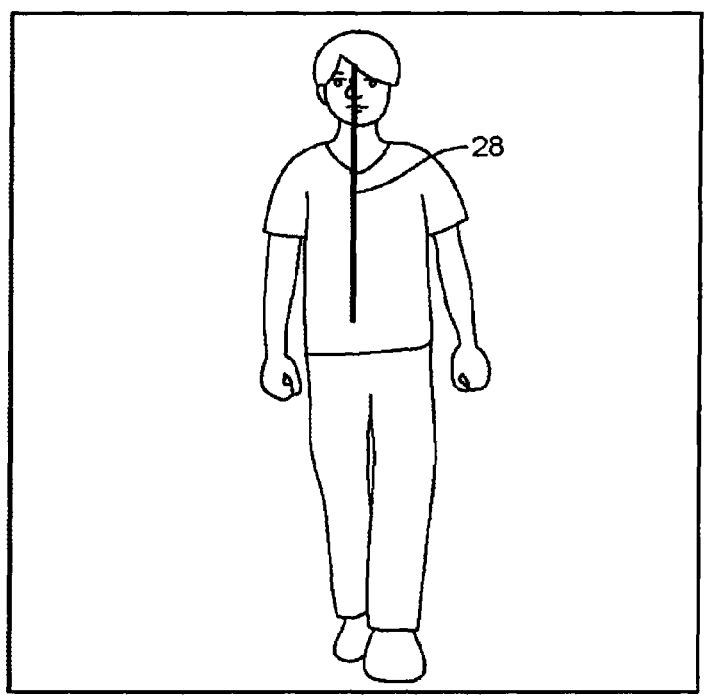
(B)
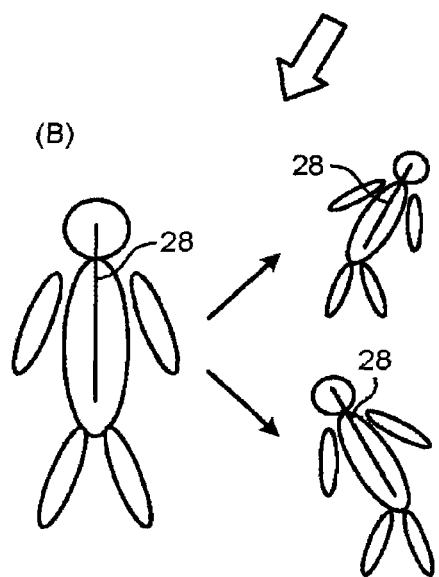
(C)
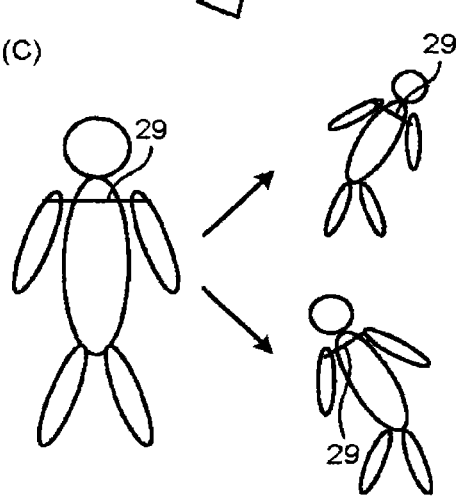

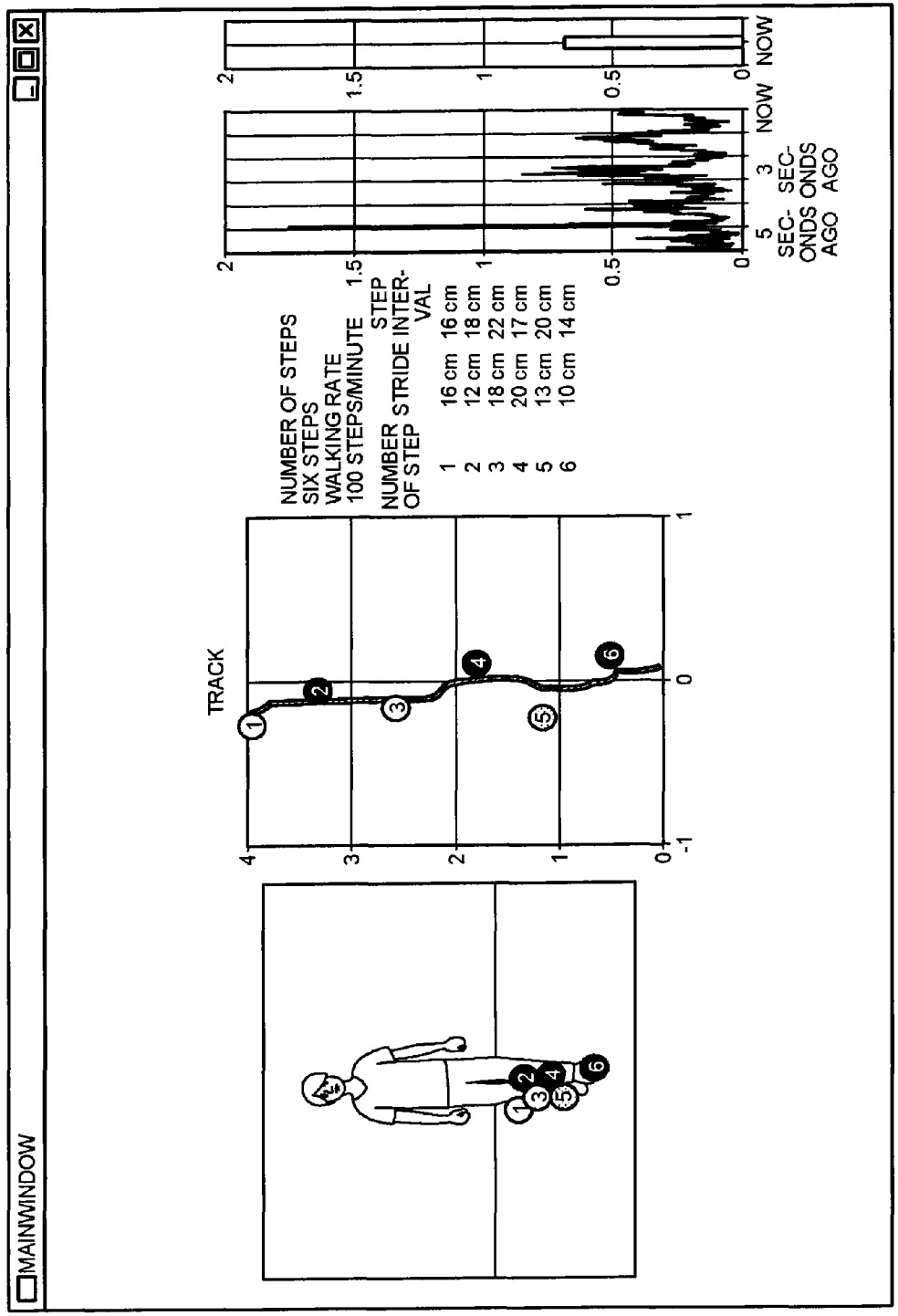

FIG.21

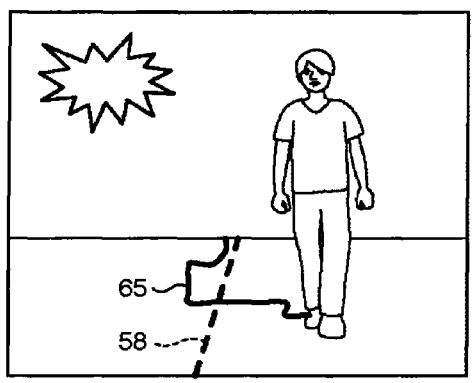

FIG.22

| WALKING STATE | WARNING |
|---|---|
| INCLINATION OF STRAIGHT LINE WHICH CONNECTS HEAD AND LOIN>20° | BODY IS INCLINED |
| INCLINATION OF STRAIGHT LINE WHICH CONNECT BOTH SHOULDERS>15° | SHOULDER IS INCLINED |
| MOVING DISTANCE IN HORIZONTAL DIRECTION OF POSITION OF CENTER OF GRAVITY IN ONE SECOND>50 cm | WALKING IS NOT STABLE, BODY IS SHAKING |
| DISTANCE BETWEEN REFERENCE LINE AND CENTER OF GRAVITY>30 cm | WALKING IS NOT PERFORMED ON REFERENCE LINE |
| AVERAGE MOVING VELOCITY OF RIGHT FOOT>> AVERAGE MOVING VELOCITY OF LEFT FOOT | LEFT FOOT IS DRAGGED |
| MOVEMENT IN HEIGHT DIRECTION OF FOOT<5 cm | FOOT IS DRAGGED |
| WALKING RATE>200 STEPS/MINUTE | WALKING IS PERFORMED TOO FAST |
| COORDINATE OF LOIN (IN WALKING TRAVELING DIRECTION)<<COORDINATE OF HEAD | SHOULDER IS ROUNDED, HEAD IS FACING DOWNWARD |

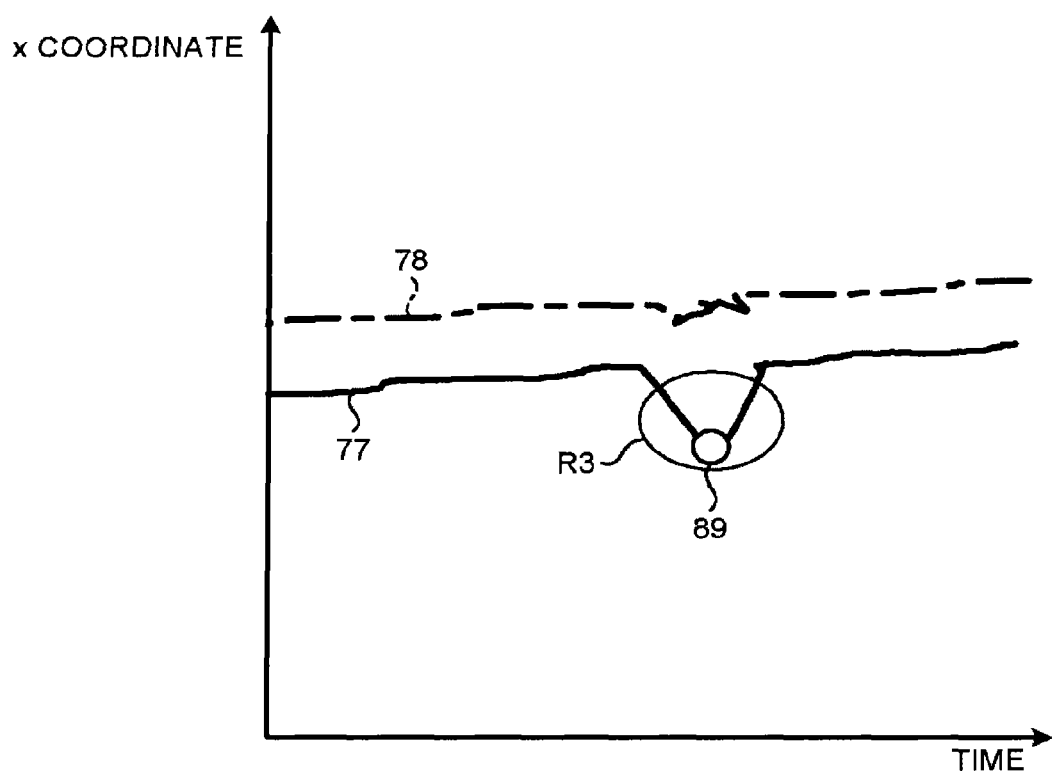

FRAME T

FIG.45

| DEPTH (m) | NUMBER OF TIMES |
|---|---|
| 0 TO 4 | 4 |
| 4 TO 8 | 3 |
| 8 TO 12 | 2 |

MOTION INFORMATION PROCESSING APPARATUS AND METHOD

CROSS-REFERENCE TO RELATED APPLICATIONS

This application is a continuation of PCT international application Ser. No. PCT/JP2014/051016 filed on Jan. 20, 2014 which designates the United States, incorporated herein by reference, and which claims the benefit of priority from Japanese Patent Application No. 2013-006826, filed on Jan. 18, 2013, Japanese Patent Application No. 2013-009648, filed on Jan. 22, 2013 and Japanese Patent Application No. 2013-154926, filed on Jul. 25, 2013, the entire contents of which are incorporated herein by reference.

FIELD

Embodiments described herein relate generally to a motion information processing apparatus and method.

BACKGROUND

Conventionally, in rehabilitation, many specialists work in cooperation in order to support a person having a physical or mental handicap caused by various causes such as illness, injury, or an aging phenomenon or having a congenital handicap to spend a better life. For example, in rehabilitation, many specialists such as a rehabilitation specialist physician, a rehabilitation nurse, a physical therapist, an occupational therapist, a speech therapist, a clinical psychotherapist, a prosthetist, and a social worker perform support in cooperation.

On the other hand, recently, development of a motion capture technique to digitally record a motion of a person or a substance is in progress. As a system of a motion capture technique, an optical-type, a mechanical-type, a magnetic-type, and a camera-type are known. For example, a camera-system in which a motion of a person is digitally recorded by attaching a marker to the person, detecting the marker by a tracker such as a camera, and processing the detected marker has been known. Also, as a system not using a marker or a tracker, a system to digitally record a motion of a person by measuring a distance from a sensor to a person with an infrared sensor and by detecting a size of the person or various motions of a skeleton has been known. As a sensor using such a system, for example, Kinect (registered trademark) is known.

BRIEF DESCRIPTION OF THE DRAWINGS

FIG. 3 is a table illustrating an example of skeleton information generated by the motion information generating circuitry according to the first embodiment;

FIG. 5 is a table illustrating an example of motion information stored by motion information storage circuitry according to the first embodiment;

FIG. 6 is a table illustrating an example of analysis information stored by analysis information storage circuitry according to the first embodiment;

FIG. 9 is a view for describing a second example of an analysis of an angle performed by the analyzing circuitry according to the first embodiment;

FIG. 12A is a view for describing a variation of superimposed image information generated by the generating circuitry according to the first embodiment;

FIG. 13 is a view illustrating an example of a display image displayed by control performed by display controlling circuitry according to the first embodiment;

FIG. 21 is a view illustrating an example of a warning display by display controlling circuitry according to a second embodiment;

FIG. 22 is a table for describing an example of a determination basis used by analyzing circuitry according to the second embodiment;

FIG. 25F is a graph for describing an example of an analysis of an irregular landing point performed by the analyzing circuitry according to the third embodiment by using an x coordinate;

FIG. 45 is a view illustrating an example of correspondence information stored in storage circuitry according to the seventh embodiment;

DETAILED DESCRIPTION

According to embodiments, a motion information processing apparatus includes processing circuitry. The processing circuitry configured to obtain motion information of an object person who executes a walking motion. The processing circuitry configured to generate track information, in which a position of a landing point of a foot of the object person and a track of a movement of the object person are indicated, based on the motion information obtained. The processing circuitry configured to perform control in such a manner that the track information generated is displayed on a display.

In the following, a motion information processing apparatus and method according to an embodiment will be described with reference to the drawings. Note that the motion information processing apparatus described in the following may be used as a single motion information processing apparatus or may be used, for example, by being embedded into a system such as a medical record system or a rehabilitation department system.

First Embodiment

Figure 1:
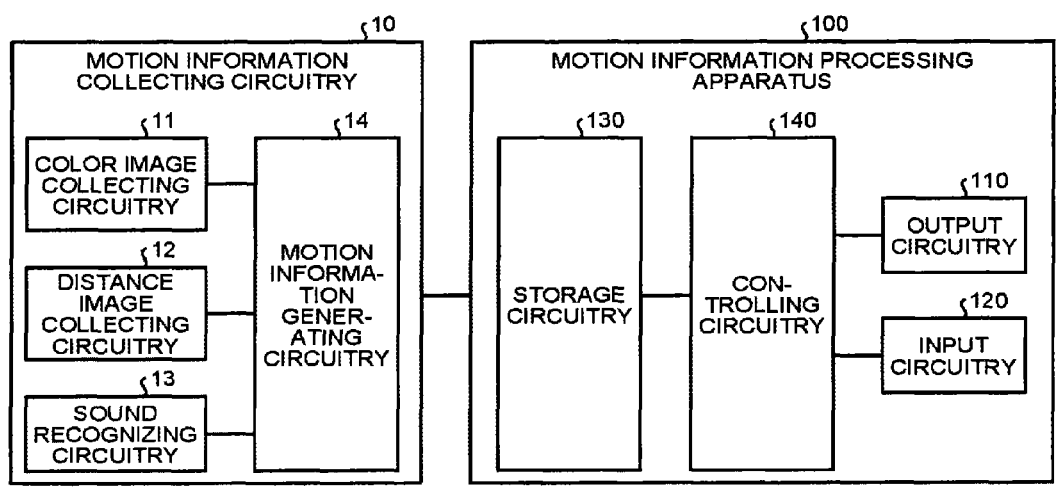
FIG. 1 is a view illustrating an example of a configuration of a motion information processing apparatus according to a first embodiment.

FIG. 1 is a view illustrating an example of a configuration of a motion information processing apparatus 100 according to a first embodiment. The motion information processing apparatus 100 according to the first embodiment is, for example, an apparatus to support rehabilitation performed in a medical institution, at home, or in an office. Here, the "rehabilitation" indicates a technique or a method to improve potential of a patient who has a handicap, a chronic disease, or a geriatric disease and is in a long treatment period and to recover and advance a vital function and a social function. The technique or the method includes, for example, functional training to recover and advance a vital function and a social function. Here, as the functional training, there is for example, walking training or range of joint motion training. Also, an object of rehabilitation will be referred to as an "object person." The object person is, for example, a sick person, an injured person, an elderly person, or a handicapped parson. Also, a person who helps an object person in rehabilitation will be referred to as a "helper." The helper is, for example, a healthcare professional, who works at a medical institution, such as a doctor, a physical therapist, or a nurse or a caregiver, a family member, or a friend who performs nursing-care of an object person at home. Also, rehabilitation will be simply referred to as "rehab."

As illustrated in FIG. 1, in the first embodiment, the motion information processing apparatus 100 is connected to motion information collecting circuitry 10.

The motion information collecting circuitry 10 detects a motion of a person, a substance, or the like in a space where rehabilitation is performed and collects motion information indicating the motion of the person, the substance, or the like. Note that the motion information will be described in detail when processing performed by motion information generating circuitry 14 described later is described. Also, as the motion information collecting circuitry 10, for example, Kinect (registered trademark) is used.

As illustrated in FIG. 1, the motion information collecting circuitry 10 includes color image collecting circuitry 11, distance image collecting circuitry 12, sound recognizing circuitry 13, and the motion information generating circuitry 14. Note that a configuration of the motion information collecting circuitry 10 illustrated in FIG. 1 is just an example and an embodiment is not limited thereto.

The color image collecting circuitry 11 photographs an object such as a person or a substance in a space, where rehabilitation is performed, and collects color image information. For example, the color image collecting circuitry 11 detects light, which is reflected on an object surface, with a light receiving element and converts visible light into an electric signal. Then, the color image collecting circuitry 11 generates color image information in one frame corresponding to a photographing range by converting the electric signal into digital data. The color image information in one frame includes, for example, photographing time information and information in which a red green blue (RGB) value is associated to each pixel included in one frame. The color image collecting circuitry 11 shoots a video of a photographing range by generating color image information in a plurality of successive frames from pieces of visible light detected successively. Note that the color image information generated by the color image collecting circuitry 11 may be output as a color image in which an RGB value of each pixel is arranged in a bitmap. Also, the color image collecting circuitry 11 includes, for example, a complementary metal oxide semiconductor (CMOS) or a charge coupled device (CCD) as the light receiving element.

The distance image collecting circuitry 12 photographs an object such as a person or a substance in a space where rehabilitation is performed and collects distance image information. For example, the distance image collecting circuitry 12 emits an infrared ray therearound and detects, with the light receiving element, reflection wave which is irradiation wave reflected on an object surface. Then, based on a phase difference between the irradiation wave and the reflection wave or a period of time from irradiation to detection, the distance image collecting circuitry 12 calculates a distance between the object and the distance image collecting circuitry 12 and generates distance image information in one frame corresponding to a photographing range. The distance image information in one frame includes, for example, photographing time information and information in which a distance between an object, which corresponds to each pixel included in the photographing range, and the distance image collecting circuitry 12 is associated to the pixel. The distance image collecting circuitry 12 shoots a video of a photographing range by generating distance image information in a plurality of successive frames from pieces of reflection wave detected successively. Note that the distance image information generated by the distance image collecting circuitry 12 may be output as a distance image in which color gradation corresponding to a distance of each pixel is arranged in a bitmap. Also, the distance image collecting circuitry 12 includes, for example, a CMOS or a CCD as a light receiving element.

The light receiving element may be shared as a light receiving element used in the color image collecting circuitry 11. Also, a unit of a distance calculated by the distance image collecting circuitry 12 is, for example, a meter [m].

The sound recognizing circuitry 13 collects a surrounding sound and performs specification of a direction of a sound source and sound recognition. The sound recognizing circuitry 13 includes a microphone array including a plurality of microphones and performs beam forming. The beam forming is a technique to selectively collect sound in a specific direction. For example, the sound recognizing circuitry 13 specifies a direction of a sound source by beam forming using the microphone array. Also, the sound recognizing circuitry 13 recognizes a word from the collected sound by using an already-known sound recognition technique. That is, the sound recognizing circuitry 13 generates, as a sound recognition result, information in which a word recognized by the sound recognition technique, a direction in which the word is spoken, and time at which the word is recognized are associated to each other.

The motion information generating circuitry 14 generates motion information indicating a motion of a person, a substance, or the like. The motion information is generated, for example, by capturing a motion (gesture) of a person as a plurality of kinds of successive posture (pose). An outline is described as follows. That is, by pattern matching using a human body pattern, the motion information generating circuitry 14 first acquires coordinates of each joint, which forms a skeleton of a human body, from the distance image information generated by the distance image collecting circuitry 12. The coordinates of each joint which coordinates are acquired from the distance image information are values indicated by a coordinate system of a distance image (hereinafter, referred to as "distance image coordinate system"). Thus, the motion information generating circuitry 14 then converts the coordinates of each joint in the distance image coordinate system into a value indicated by a coordinate system of a three-dimensional space where rehabilitation is performed (hereinafter, referred to as "world coordinate system"). The coordinates of each joint which coordinates are indicated by the world coordinate system are skeleton information in one frame. Also, pieces of skeleton information in a plurality of frames are motion information. In the following, processing in the motion information generating circuitry 14 according to the first embodiment will be described in detail.

Figure 2A:
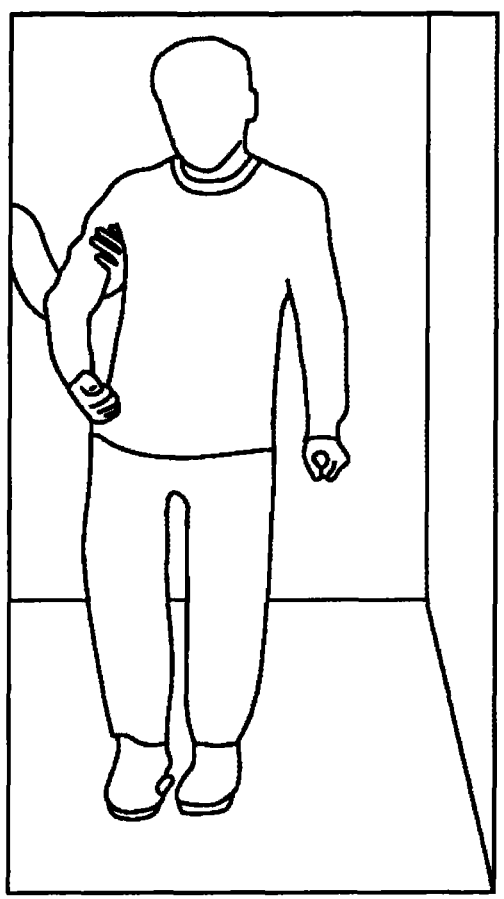
FIG. 2A is a view for describing processing in motion information generating circuitry according to the first embodiment.
Figure 2B:
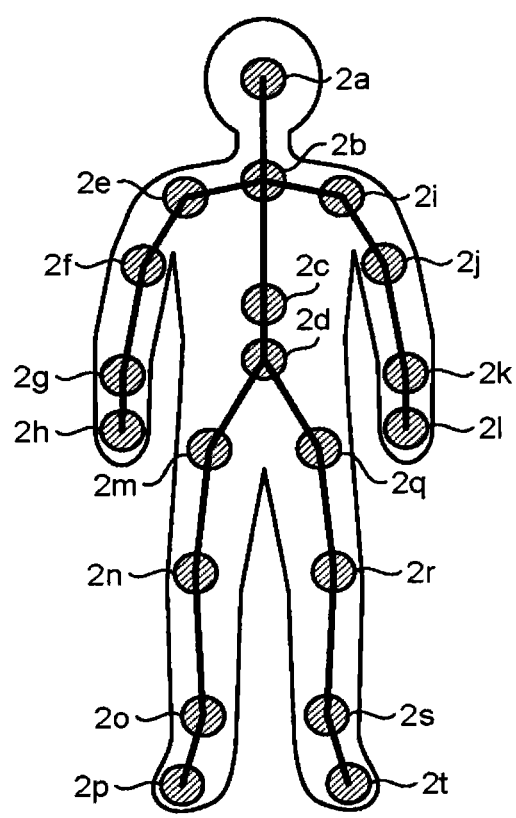
FIG. 2B is a view for describing processing in the motion information generating circuitry according to the first embodiment.
Figure 2C:
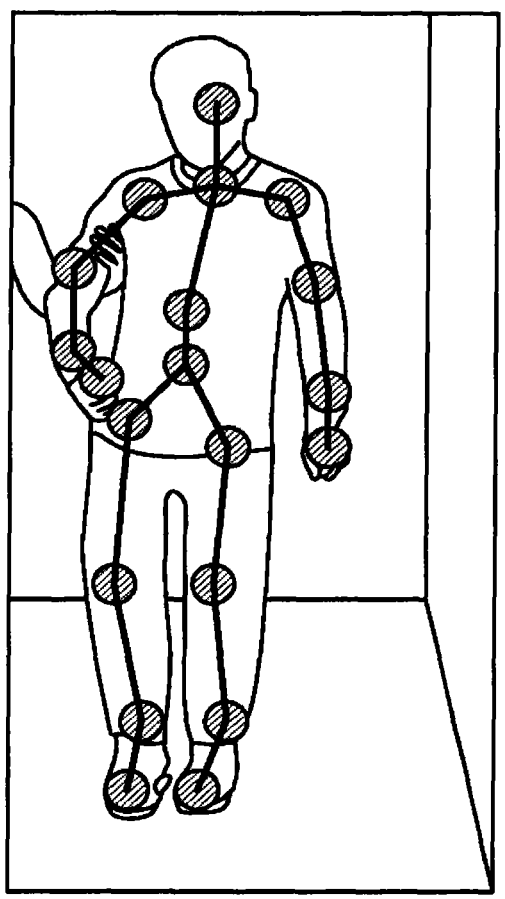
FIG. 2C is a view for describing processing in the motion information generating circuitry according to the first embodiment.

FIG. 2A to FIG. 2C are views for describing processing in the motion information generating circuitry 14 according to the first embodiment. In FIG. 2A, an example of a distance image generated by the distance image collecting circuitry 12 is illustrated. Note that in FIG. 2A, for convenience of description, an image expressed by a line-drawing is illustrated. However, an actual distance image is an image or the like expressed by color gradation corresponding to a distance. In the distance image, each pixel includes a three-dimensional value in which a "pixel position X" in a right/left direction of the distance image, a "pixel position Y" in an upward/downward direction of the distance image, and a "distance Z" between an object corresponding to the pixel and the distance image collecting circuitry 12 are associated to each other. In the following, values of coordinates in the distance image coordinate system will be expressed as a three-dimensional value (X, Y, Z).

In the first embodiment, the motion information generating circuitry 14 previously stores a human body pattern corresponding to various kinds of posture, for example, by learning. Each time distance image information is generated by the distance image collecting circuitry 12, the motion information generating circuitry 14 acquires the generated distance image information in each frame. Then, the motion information generating circuitry 14 performs pattern matching with respect to the acquired distance image information in each frame by using a human body pattern.

Here, the human body pattern will be described. In FIG. 2B, an example of the human body pattern is illustrated. In the first embodiment, since being a pattern used for pattern matching with the distance image information, the human body pattern is expressed in the distance image coordinate system. Also, similarly to a person drawn onto a distance image, information of a surface of a human body (hereinafter, referred to as "human body surface") is included. For example, the human body surface corresponds to a surface of a skin or clothing of the person. Moreover, as illustrated in FIG. 2B, the human body pattern includes information of each joint which forms a skeleton of a human body. That is, in the human body pattern, a relative positional relationship between the human body surface and each joint is already known.

In the example illustrated in FIG. 2B, the human body pattern includes information of 20 joints from a joint 2a to a joint 2t. Among these, the joint 2a corresponds to a head, the joint 2b corresponds to a center part of both shoulders, the joint 2c corresponds to a loin, and the joint 2d corresponds to a center part of a hip. Also, the joint 2e corresponds to a right shoulder, the joint 2f corresponds to a right elbow, the joint 2g corresponds to a right wrist, and the joint 2h corresponds to a right hand. Also, the joint 2i corresponds to a left shoulder, the joint 2j corresponds to a left elbow, the joint 2k corresponds to a left wrist, and the joint 2l corresponds to a left hand. Also, the joint 2m corresponds to a right hip, the joint 2n corresponds to a right knee, the joint 2o corresponds to a right ankle, and the joint 2p corresponds to a right tarsus. Also, the joint 2q corresponds to a left hip, the joint 2r corresponds to a left knee, the joint 2s corresponds to a left ankle, and the joint 2t corresponds to a left tarsus.

Note that in FIG. 2B, a case where the human body pattern includes information of 20 joints has been described but an embodiment is not limited thereto. A position of a joint and the number of joints may be set arbitrarily by an operator. For example, in a case of only capturing a change in a motion of limbs, it is not necessary to acquire information of the joint 2b and the joint 2c among the joint 2a to the joint 2d. Also, in a case of capturing a change in a motion of a right hand in detail, a joint of each finger of the right hand may be newly set in addition to the joint 2h. Note that each of the joint 2a, the joint 2h, the joint 2l, the joint 2p, and the joint 2t in FIG. 2B is an end part of a bone and is different from a so-called joint. However, since being an important point indicating a position and a direction of a bone, each of these is described as a joint for convenience of description.

By using the human body pattern, the motion information generating circuitry 14 performs pattern matching with distance image information in each frame. For example, the motion information generating circuitry 14 extracts, from the distance image information, a person in certain posture by performing pattern matching between the human body surface of the human body pattern illustrated in FIG. 2B and the distance image illustrated in FIG. 2A. In such a manner, the motion information generating circuitry 14 acquires coordinates of the human body surface of the person drawn onto the distance image. Also, as described above, in the human body pattern, a relative positional relationship between the human body surface and each joint is already known. Thus, the motion information generating circuitry 14 calculates coordinates of each joint in the person from the coordinates of the human body surface of the person drawn onto the distance image. In such a manner, as illustrated in FIG. 2C, the motion information generating circuitry 14 acquires, from the distance image information, coordinates of each joint which forms a skeleton of a human body. Note that the coordinates of each joint which coordinates are acquired here are coordinates in the distance coordinate system.

Note that the motion information generating circuitry 14 may use information, which indicates a positional relationship between joints, in an auxiliary manner when performing the pattern matching. The information indicating a positional relationship between joints includes, for example, a coupling relationship between joints (such as "joint 2a and joint 2b being coupled") or a range of motion of each joint. A joint is a part to couple two or more bones. An angle between bones varies according to a change in posture. Also, a range of motion varies depending on a joint. For example, the range of motion is expressed by the maximum value, the minimum value, and the like of an angle between bones coupled by each joint. For example, the motion information generating circuitry 14 learns a range of motion of each joint when learning a human body pattern and stores the range of motion while associating the range to each joint.

Subsequently, the motion information generating circuitry 14 converts coordinates of each joint in the distance image coordinate system into a value indicated in the world coordinate system. The world coordinate system is a coordinate system in a three-dimensional space where rehabilitation is performed and is, for example, a coordinate system with a position of the motion information collecting circuitry 10 as an origin, a horizontal direction as an x-axis, a vertical direction as a y-axis, and a direction orthogonal to an xy plane as a z-axis. Note that a value of a coordinate in the z-axis direction may be referred to as a "depth."

Here, processing of converting the distance image coordinate system into the world coordinate system will be described. In the first embodiment, the motion information generating circuitry 14 previously stores a conversion equation to convert the distance image coordinate system into the world coordinate system. For example, the conversion equation outputs coordinates in the world coordinate system when coordinates in the distance image coordinate system and an incident angle of reflection light corresponding to the coordinates are input. For example, the motion information generating circuitry 14 inputs coordinates (X1, Y1, Z1) of a certain joint and an incident angle of reflection light corresponding to the coordinates into the conversion equation and converts the coordinates (X1, Y1, Z1) of the certain joint into coordinates (x1, y1, z1) in the world coordinate system. Note that since a correspondence relationship between the coordinates in the distance image coordinate system and the incident angle of the reflection light is already known, the motion information generating circuitry 14 can input an incident angle corresponding to the coordinates (X1, Y1, Z1) into the conversion equation. Also, here, a case where the motion information generating circuitry 14 converts coordinates in the distance image coordinate system into coordinates in the world coordinate system has been described. However, it is also possible to convert coordinates in the world coordinate system into coordinates in the distance coordinate system.

Then, the motion information generating circuitry 14 generates skeleton information from coordinates of each joint indicated in the world coordinate system. FIG. 3 is a table illustrating an example of skeleton information generated by the motion information generating circuitry 14. Skeleton information in each frame includes photographing time information of the frame and coordinates of each joint. For example, as illustrated in FIG. 3, the motion information generating circuitry 14 generates skeleton information in which joint identification information and coordinate information are associated to each other. Note that in FIG. 3, the photographing time information is not illustrated. The joint identification information is identification information to identify a joint and is set previously. For example, joint identification information "2a" corresponds to a head and joint identification information "2b" corresponds to a center part of both shoulders. Similarly in different joint identification information, each piece of joint identification information indicates a corresponding joint. Also, the coordinate information indicates coordinates of each joint in each frame in the world coordinate system.

In a first line in FIG. 3, the joint identification information "2a" and the coordinate information "(x1, y1, z1)" are associated to each other. That is, the skeleton information in FIG. 3 indicates that a head is at a position of the coordinates (x1, y1, z1) in a certain frame. Also, in a second line in FIG. 3, the joint identification information "2b" and coordinate information "(x2, y2, z2)" are associated to each other. That is, skeleton information in FIG. 3 indicates that a center part of both shoulders is at a position of the coordinates (x2, y2, z2) in a certain frame. Similarly, with respect to a different joint, it is indicated that each joint in a certain frame is at a position indicated in coordinates.

In such a manner, the motion information generating circuitry 14 generates skeleton information in each frame by performing pattern matching with respect to distance image information in each frame and converting the distance image coordinate system into the world coordinate system at each time the distance image information in each frame is acquired from the distance image collecting circuitry 12. Then, the motion information generating circuitry 14 outputs the generated skeleton information in each frame to the motion information processing apparatus 100 and stores the information into storage circuitry 130 described later.

Note that processing in the motion information generating circuitry 14 is not limited to the above-described method. For example, in the above, a method in which the motion information generating circuitry 14 performs pattern matching by using a human body pattern has been described but an embodiment is not limited thereto. For example, a method in which pattern matching is performed by using a sectional pattern instead of or along with a human body pattern may be used.

Also, for example, in the above, a method in which the motion information generating circuitry 14 acquires coordinates of each joint from the distance image information has been described but an embodiment is not limited thereto. For example, a method in which the motion information generating circuitry 14 acquires coordinates of each joint by using color image information along with the distance image information may be used. In this case, for example, the motion information generating circuitry 14 performs pattern matching between a human body pattern expressed in a coordinate system of a color image and color image information and acquires coordinates of a human body surface from the color image information. In the coordinate system of the color image, information called the "distance Z" in the distance image coordinate system is not included. Thus, the motion information generating circuitry 14 acquires the information of the "distance Z" from distance image information and acquires coordinates of each joint in the world coordinate system by calculation processing using the two pieces of information.

Also, when necessary, the motion information generating circuitry 14 arbitrarily outputs, to the motion information processing apparatus 100, the color image information generated by the color image collecting circuitry 11, the distance image information generated by the distance image collecting circuitry 12, and the sound recognition result output from the sound recognizing circuitry 13 and stores these into the storage circuitry 130 described later. Note that it is possible to previously perform association of a pixel position of the color image information and a pixel position of the distance image information according to a position and a photographing direction of the color image collecting circuitry 11 and those of the distance image collecting circuitry 12. Thus, the pixel position of the color image information and the pixel position of the distance image information can be associated to the world coordinate system calculated by the motion information generating circuitry 14. In addition, by using the association and a distance [m] calculated by the distance image collecting circuitry 12, it is possible to calculate a height or a length of each part of a body (length of arm or length of abdomen) or to calculate a distance between two pixels designated on a color image. Similarly, it is also possible to previously perform association of photographing time information of the color image information and photographing time information of the distance image information. Also, when the motion information generating circuitry 14 refers to the sound recognition result and the distance image information and there is a joint 2a near a direction where a word is recognized at certain time, it is possible to output the word as a word spoken by a person including the joint 2a. Moreover, the motion information generating circuitry 14 arbitrarily outputs information indicating a positional relationship between joints to the motion information processing apparatus 100 when necessary and stores the information into the storage circuitry 130 described later.

Also, the motion information generating circuitry 14 generates depth image information in one frame corresponding to a photographing range by using a depth which is a value of a coordinate in the z-axis direction of the world coordinate system. In the depth image information in one frame, for example, photographing time information and information in which a depth corresponding to each pixel included in a photographing range is associated to the pixel are included. In other word, the depth image information is information to which depth information is associated instead of distance information associated to each pixel of distance image information. Each pixel position can be indicated in a distance image coordinate system similar to that of the distance image information. The motion information generating circuitry 14 outputs the generated depth image information to the motion information processing apparatus 100 and stores the information into the storage circuitry 130 described later. Note that the depth image information may be output as a depth image in which gradation of color corresponding to a depth of each pixel is arranged in a bitmap.

Note that here, a case where a motion of one person is detected by the motion information collecting circuitry 10 has been described but an embodiment is not limited thereto. The motion information collecting circuitry 10 may detect motions of a plurality of people when the people are included in a photographing range of the motion information collecting circuitry 10. Note that when a plurality of people is photographed in distance image information in an identical frame, the motion information collecting circuitry 10 performs association of skeleton information of the plurality of people which information is generated from the distance image information of the identical frame and outputs this as motion information to the motion information processing apparatus 100.

Also, a configuration of the motion information collecting circuitry 10 is not limited to the above-described configuration. For example, in a case of generating motion information by detecting a motion of a person with different motion capture such as that in an optical-type, a mechanical-type, or a magnetic-type, the motion information collecting circuitry 10 does not necessarily include the distance image collecting circuitry 12. In such a case, the motion information collecting circuitry 10 includes, as motion sensors, a marker mounted on a human body to detect a motion of a person and a sensor to detect the marker. Then, the motion information collecting circuitry 10 detects a motion of the person by using the motion sensors and generates motion information. Also, the motion information collecting circuitry 10 associates a pixel position of the color image information with coordinates of the motion information by using a position of the marker included in an image photographed by the color image collecting circuitry 11 and arbitrarily outputs this to the motion information processing apparatus 100 when necessary. Also, for example, the motion information collecting circuitry 10 may not include the sound recognizing circuitry 13 when the sound recognition result is not output to the motion information processing apparatus 100.

Also, in the above-described embodiment, the motion information collecting circuitry 10 outputs, as skeleton information, coordinates in the world coordinate system but an embodiment is not limited thereto. For example, the motion information collecting circuitry 10 may output coordinates in the distance image coordinate system before conversion and conversion from the distance image coordinate system to the world coordinate system may be performed on a side of the motion information processing apparatus 100 when necessary.

Referring back to FIG. 1, the motion information processing apparatus 100 performs processing to support rehabilitation by using the motion information output from the motion information collecting circuitry 10. More specifically, the motion information processing apparatus 100 generates and displays display information, with which it is possible to evaluate a walking condition, by using motion information of an object person performing walking training which information is collected by the motion information collecting circuitry 10. Also, the motion information processing apparatus 100 analyzes the motion information of the object person performing the walking training which information is collected by the motion information collecting circuitry 10.

As described above, conventionally, walking training has been performed as a kind of functional training of rehabilitation. In the walking training, walking executed by the object person is observed by a doctor, a physical therapist, or the like and a walking condition of the object person is evaluated. For example, in the walking training, various walking conditions such as a step pattern, a shake of an upper body, velocity of walking, a stride, and a step interval are evaluated. Here, conventionally, there is a case where there is a difference in evaluation of the walking condition between doctors and physical therapists. Thus, the motion information processing apparatus 100 according to the present embodiment is configured to provide display information, with which it is easier to evaluate a walking condition, in such a manner that a difference in evaluation of the walking condition is controlled. Also, the motion information processing apparatus 100 according to the present embodiment is configured to analyze a walking state including a landing point of a foot in walking of an object person in such a manner that it becomes easy to evaluate a walking condition.

For example, the motion information processing apparatus 100 is an information processing apparatus such as a computer or a workstation and includes output circuitry 110, input circuitry 120, the storage circuitry 130, and controlling circuitry 140 as illustrated in FIG. 1.

The output circuitry 110 outputs various kinds of information to support rehabilitation. More specifically, the output circuitry 110 outputs various kinds of information to evaluate a walking condition. Also, the output circuitry 110 outputs, for example, various kinds of information related to a walking state of an object person. For example, the output circuitry 110 displays a graphical user interface (GUI), through which an operator to operate the motion information processing apparatus 100 inputs various requests by using the input circuitry 120, displays display information, an output image, or the like generated in the motion information processing apparatus 100, or outputs a warning sound. Also, for example, the output circuitry 110 displays information related to a walking state of an object person which information is analyzed in the motion information processing apparatus 100 or outputs a warning sound. For example, the output circuitry 110 is a monitor, a speaker, a headphone, or a headphone part of a heat set. Also, the output circuitry 110 may be a display mounted on a body of a user such as an eyeglass-shaped display or a head-mounted display.

The input circuitry 120 received an input of various kinds of information to support rehabilitation. More specifically, the input circuitry 120 receives an input of various kinds of information to evaluate a walking condition. Also, the input circuitry 120 receives an input of various kinds of information related to an analysis of a walking state. For example, the input circuitry 120 receives an input of various requests (such as selection request of display information, selection request of item to be analyzed, or measurement request for execution of measurement on GUI) from an operator of the motion information processing apparatus 100 and transfers the received various requests to the motion information processing apparatus 100. For example, the input circuitry 120 is a mouse, a keyboard, a touch-command screen, a trackball, a microphone, or a microphone part of a head set. Also, the input circuitry 120 may be a sensor to acquire biological information such as a sphygmomanometer, a heart rate meter, or a thermometer.

The storage circuitry 130 is, for example, a semiconductor memory element such as a random access memory (RAM) or a flash memory or a storage apparatus such as a hard disk apparatus or an optical disk apparatus. Also, the controlling circuitry 140 can be realized when an integrated circuit such as an application specific integrated circuit (ASIC) or a field programmable gate array (FPGA) or a central processing unit (CPU) executes a predetermined program.

In the above, a configuration of the motion information processing apparatus 100 according to the first embodiment has been described. With such a configuration, the motion information processing apparatus 100 according to the first embodiment provides, by a configuration described in detail in the following, display information with which it is easy to evaluate a walking condition. Here, the motion information processing apparatus 100 according to the present application is configured to provide the above-described display information with which it is easy to evaluate a walking condition. In addition, the motion information processing apparatus 100 is configured to make it easy to evaluate a walking condition and make it possible to perform a clinically useful gait analysis. In the following, in each of the first embodiment and a second embodiment, a motion information processing apparatus to provide display information with which it is easy to evaluate a walking condition will be described. In each of a third embodiment and a fourth embodiment, a motion information processing apparatus to make it easy to evaluate a walking condition will be described. In each of fifth to seventh embodiments, a motion information processing apparatus to perform a clinically useful gait analysis will be described.

Figure 4:
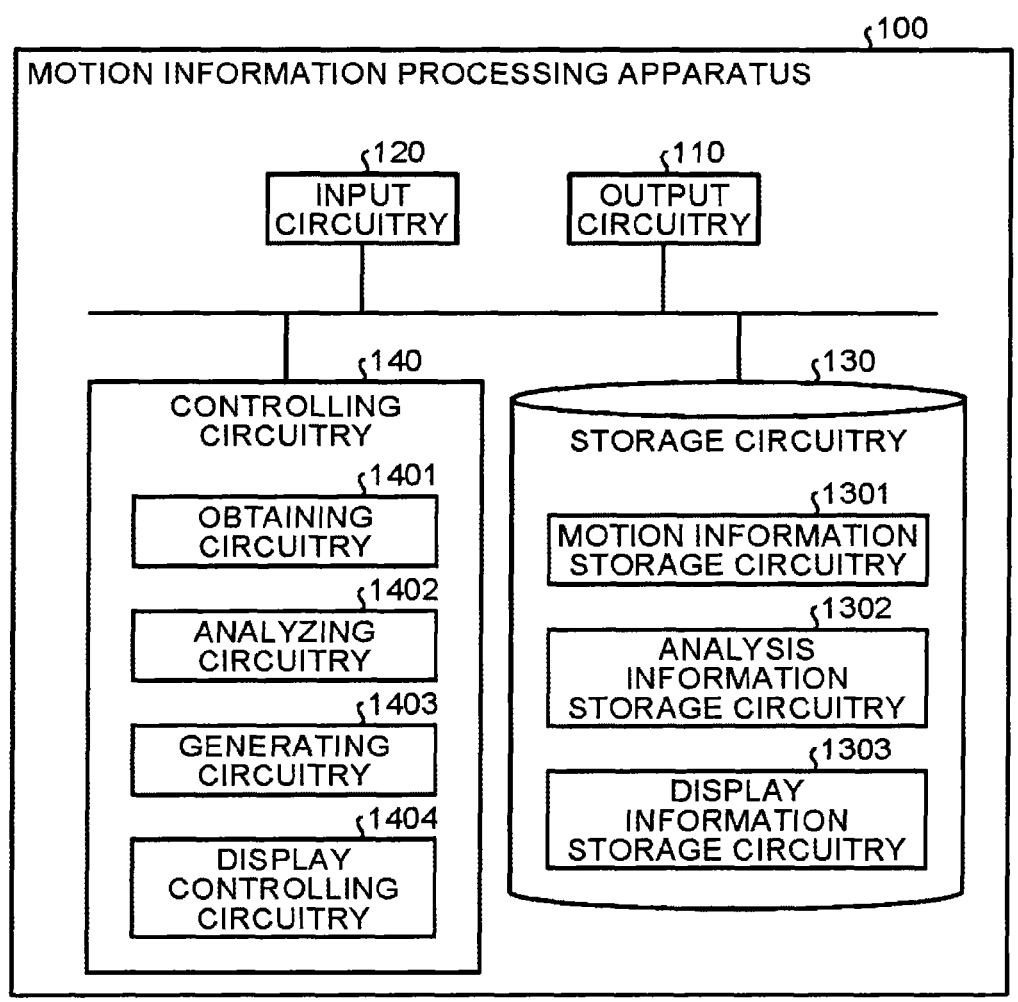
FIG. 4 is a view illustrating an example of a detail configuration of the motion information processing apparatus according to the first embodiment.

FIG. 4 is a view illustrating an example of a detail configuration of the motion information processing apparatus 100 according to the first embodiment. First, a detail of the storage circuitry 130 in the motion information processing apparatus 100 will be described. As illustrated in FIG. 4, in the motion information processing apparatus 100, for example, the storage circuitry 130 includes motion information storage circuitry 1301, analysis information storage circuitry 1302, and display information storage circuitry 1303.

The motion information storage circuitry 1301 stores various kinds of information collected by the motion information collecting circuitry 10. More specifically, the motion information storage circuitry 1301 stores motion information generated by the motion information generating circuitry 14. More specifically, the motion information storage circuitry 1301 stores skeleton information in each frame which information is generated by the motion information generating circuitry 14. Here, the motion information storage circuitry 1301 can further store color image information, distance image information, and a sound recognition result output from the motion information generating circuitry 14 while associating these into each frame.

FIG. 5 is a table illustrating an example of motion information stored by the motion information storage circuitry 1301 according to the first embodiment. As illustrated in FIG. 5, the motion information storage circuitry 1301 stores motion information in which a name number, a performance date, and motion information are associated to each other with respect to each name. Here, the "name number" is an identifier to uniquely identify an object person and is assigned to each name. The "performance date" indicates a date and time on which the object person performs walking training. The "motion information" indicates information collected by the motion information collecting circuitry 10.

For example, as illustrated in FIG. 5, the motion information storage circuitry 1301 stores "a name: A, a name number: 1, a performance date: 20120801_1, and motion information: color image information, distance image information, a sound recognition result, skeleton information, . . ." The above-described information indicates that motion information including the "color image information," the "distance image information," the "sound recognition result," and the "skeleton information" is stored as motion information of "first" walking performed on "August 1st" in "2012" by a person with the "name: A" the "name number" of which is "1."

Here, in the motion information illustrated in FIG. 5, "color image information," "distance image information," a "sound recognition result," and "skeleton information" in all frames photographed during execution of a walking motion are associated to time and stored in time series.

Also, as illustrated in FIG. 5, the motion information storage circuitry 1301 stores "a name: A, a name number: 1, a performance date: 20120801_2, and motion information: color image information, distance image information, sound recognition result, skeleton information, . . . " That is, the motion information storage circuitry 1301 similarly stores motion information of "second" walking performed on "August 1st" in "2012" by the person with the "name: A."

Also, as illustrated in FIG. 5, the motion information storage circuitry 1301 also stores, with respect to a person with "a name: B and a name number: 2," motion information including "color image information," "distance image information," a "sound recognition result," and "skeleton information." In such a manner, the motion information storage circuitry 1301 stores motion information of walking, which information is collected for each object person, while associating the information to each object person. Note that the motion information illustrated in FIG. 5 is just an example. That is, the motion information storage circuitry 1301 can store information other than the "color image information," the "distance image information," the "sound recognition result," and the "skeleton information" illustrated in FIG. 5 while further associating the information. Also, for example, when the motion information collecting circuitry 10 does not include the sound recognizing circuitry 13, storing is performed without the sound recognition result.

Also, each of the "color image information" and the "distance image information" included in the motion information includes image data in a BIT MAP, a JPEG, or a different binary format or a link or the like to the image data. Also, in addition to the above-described recognition information, the "sound recognition result" included in the motion information may be sound data itself or a link to recognition information or sound data.

The analysis information storage circuitry 1302 stores an analysis result by the controlling circuitry 140 described later. More specifically, the analysis information storage circuitry 1302 stores an analysis result which is analyzed by the controlling circuitry 140 described later by using motion information stored in the motion information storage circuitry 1301. FIG. 6 is a table illustrating an example of analysis information stored in the analysis information storage circuitry 1302 according to the first embodiment. Here, a "name number" is an identifier to uniquely identify an object person and is assigned to each name. A "performance date" indicates a date and time on which the object person performs walking training. Also, "analysis information" indicates information of an analysis result analyzed by the controlling circuitry 140 described later.

For example, as illustrated in FIG. 6, the analysis information storage circuitry 1302 stores "a name: A, a name number: 1, a performance date: 20120801_1, and analysis information: a landing point of a foot, an angle, velocity, acceleration, the number of steps, a stride, an overlapped walking distance, a step interval, a walking rate, . . . " The above-described information indicates that analysis information including a "landing point of a foot," an "angle," "velocity," "acceleration," the "number of steps," a "stride," an "overlapped walking distance," a "step interval," and a "walking rate" is stored as information of an analysis result analyzed by using motion information of "first" walking performed on "August 1st" in "2012" by a person with the "name: A" the "name number" of which is "1."

Here, the "landing point of a foot" is information indicating a position, where a foot of an object person touches a ground, and is stored, for example, as coordinate information. Also, the "angle" is information indicating an angle of a body of an object person during walking and information of an angle between a predetermined basis and a part of a body is stored. For example, the analysis information storage circuitry 1302 stores, as the "angle" of the analysis information, information such as an angle of a body in a vertical direction. Note that with respect to the information of the "angle" of the analysis information, a basis and a part of a body are arbitrarily set by an operator. Also, the "velocity" is information indicating velocity of an object person during walking. For example, information of velocity of a predetermined part (such as center of body) is stored. Also, the "acceleration" is information indicating acceleration of an object person during walking. For example, information of acceleration of a predetermined part is stored. Also, the "number of steps" is information indicating the number of steps the object person walks in walking training. Also, the "stride" is information indicating a distance in a traveling direction from a landing point of a right foot (left foot) to a landing point of a left foot (right foot) in walking by an object person. Also, the "overlapped walking distance" is information indicating a distance from landing of one foot to next landing of the foot. Also, the "step interval" is information indicating a distance in a direction orthogonal to a traveling direction from a landing point of a right foot (left foot) to a landing point of a left foot (right foot) in walking by an object person. Also, the "walking rate" is information indicating the number of steps in a unit time.

Similarly, as illustrated in FIG. 6, the analysis information storage circuitry 1302 stores, with respect to a person with "a name: B and a name number: 2," analysis information including a "landing point of a foot," an "angle," "velocity," "acceleration," the "number of steps," a "stride," an "overlapped walking distance," a "step interval," and a "walking rate." In such a manner, the analysis information storage circuitry 1302 stores analysis information, which is motion information of walking collected for each object person and analyzed by the controlling circuitry 140 described later, while associating the analysis information to each object person. Note that the analysis information illustrated in FIG. 6 is just an example. For example, walking time, a period of time in which a foot is on the ground, or the like may be also included. Various kinds of information included in analysis information are arbitrarily changed according to setting performed by an operator with respect to the controlling circuitry 140 described later. For example, there is a case where an item among the pieces of information illustrated in FIG. 6 is not calculated.

Referring back to FIG. 4, the display information storage circuitry 1303 stores display information generated by the controlling circuitry 140 described later. More specifically, the display information storage circuitry 1303 stores display information which is generated by the controlling circuitry 140 described later and with which it is easy to evaluate a walking condition of an object person. Note that a detail of the display information will be described later.

Next, a detail of the controlling circuitry 140 of the motion information processing apparatus 100 will be described. As illustrated in FIG. 4, in the motion information processing apparatus 100, the controlling circuitry 140 includes, for example, obtaining circuitry 1401, analyzing circuitry 1402, generating circuitry 1403, and display controlling circuitry 1404.

The obtaining circuitry 1401 obtains motion information of an object person who executes walking training. More specifically, the obtaining circuitry 1401 obtains the motion information collected by the motion information collecting circuitry 10 and stored in the motion information storage circuitry 1301. For example, according to analysis contents by the analyzing circuitry 1402 described later, the obtaining circuitry 1401 obtains at least one of color image information, distance image information, a sound recognition result, and skeleton information stored in each frame by the motion information storage circuitry 1301.

For example, when a landing point of a foot, an angle, velocity, and the like are analyzed by the analyzing circuitry 1402 described later, the obtaining circuitry 1401 obtains all pieces of color image information, distance image information, and skeleton information related to a series of walking motions in walking training of an object person.

The analyzing circuitry 1402 executes various kinds of analysis by using motion information of an object person who executes a walking motion which information is obtained by the obtaining circuitry 1401. More specifically, by using the motion information, which is obtained by the obtaining circuitry 1401, such as the color image information, the distance image information, the sound recognition result, and the skeleton information, the analyzing circuitry 1402 calculates analysis information such as a landing point of a foot, an angle, velocity, acceleration, the number of steps, a stride, an overlapped walking distance, a step interval, and a walking rate of the object person during walking and stores a calculated analysis result into the analysis information storage circuitry 1302.

Figure 7A:
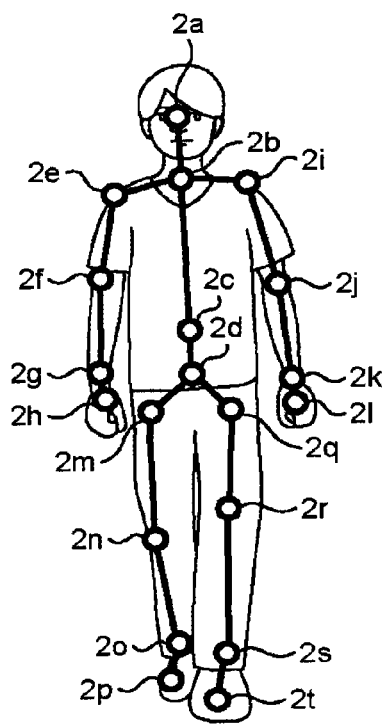
FIG. 7A is a view for describing an example of an analysis of a landing point of a foot performed by analyzing circuitry according to the first embodiment.
Figure 7B:
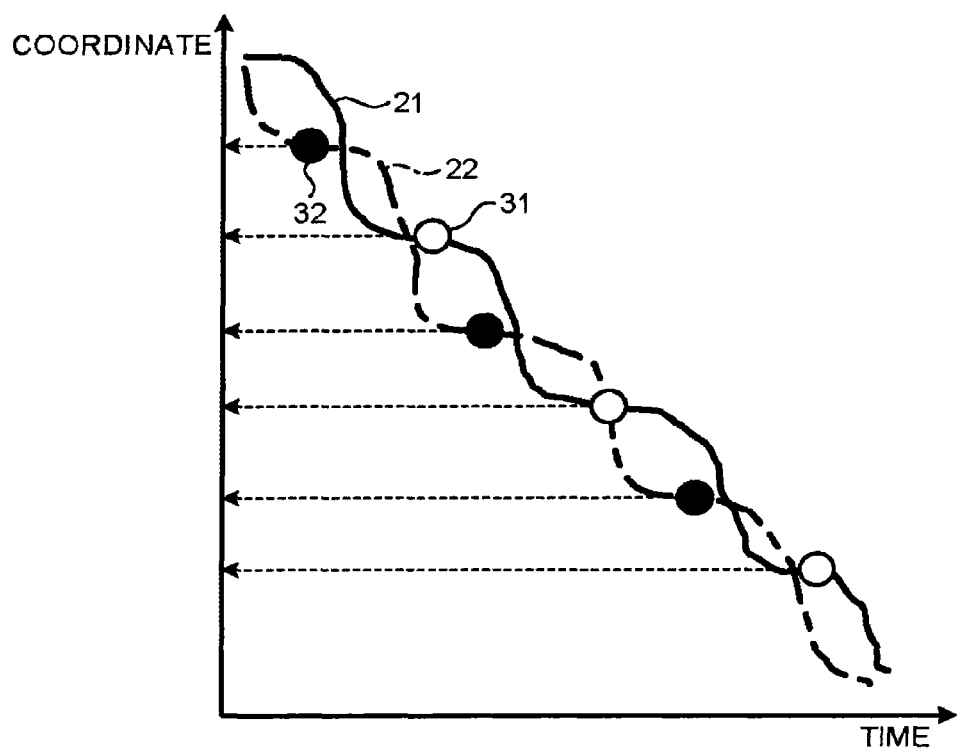
FIG. 7B is a graph for describing an example of an analysis of a landing point of a foot performed by the analyzing circuitry according to the first embodiment.

First, a case of analyzing a landing point of a foot will be described. FIG. 7A and FIG. 7B are a view and a graph for describing an example of an analysis of a landing point of a foot performed by the analyzing circuitry 1402 according to the first embodiment. In FIG. 7A and FIG. 7B, a case of calculating a landing point of a foot of an object person by using skeleton information in the motion information collected by the motion information collecting circuitry 10 is illustrated. FIG. 7A is a view schematically illustrating skeleton information in one frame which information is collected by the motion information collecting circuitry 10. Also, FIG. 7B is a graph illustrating an example of calculation of a landing point of a foot.

Here, in a case of calculating a landing point of a foot of the object person, for example, an operator such as a doctor or a physical therapist first inputs an instruction request of analysis through the input circuitry 120. Here, by inputting a name or a name number of an object person, a performance date, and the like, the operator makes the obtaining circuitry 1401 obtain intended motion information. The obtaining circuitry 1401 obtains, from the motion information storage circuitry 1301, motion information corresponding to the object person received through the input circuitry 120. Note that in a case where processing is executed along with walking training in real time, it is possible to perform setting in such a manner that motion information is obtained automatically without reception of an operation from the operator.

For example, as illustrated in FIG. 7A, the obtaining circuitry 1401 obtains, from the motion information storage circuitry 1301, skeleton information in each frame of a designated object person. By using the skeleton information obtained by the obtaining circuitry 1401, the analyzing circuitry 1402 calculates a landing point where a foot of the object person touches a ground. For example, as illustrated in FIG. 7A, the analyzing circuitry 1402 calculates a landing point by using coordinate information of a joint, which corresponds to each part of a foot, in the skeleton information of the object person executing the walking training.

For example, the analyzing circuitry 1402 calculates a landing point of an object person by using coordinate information of a joint "$2p$" corresponding to a right tarsus and that of a joint "$2t$" corresponding to a left tarsus. For example, the analyzing circuitry 1402 acquires a z coordinate of each of the joint "$2p$" corresponding to the right tarsus and the joint "$2t$" corresponding to the left tarsus from all frames and a graph with a vertical axis as a coordinate and a horizontal axis as time is created as illustrated in FIG. 7B.

That is, as illustrated in FIG. 7B, the analyzing circuitry 1402 calculates a curved line 21 indicating a temporal change in the z coordinate of the left tarsus and a curved line 22 indicating a temporal change in the z coordinate of the right tarsus. Then, for example, the analyzing circuitry 1402 determines that a time point at which a change in a value of the z coordinate in a unit time in each curved line is equal to or smaller than a predetermined threshold is a time point at which a foot touches a ground.

For example, as illustrated in FIG. 7B, the analyzing circuitry 1402 determines that a time point 31 at which a change in a coordinate in a unit time is equal to or smaller than a predetermined threshold in the curved line 21 indicating a temporal change in the z coordinate of the left tarsus is a time point at which a foot touches a ground. Similarly, as illustrated in FIG. 7B, the analyzing circuitry 1402 determines that a time point 32 at which a change in a coordinate in a unit time is equal to or smaller than a predetermined threshold in the curved line 22 indicating a temporal change in the z coordinate of the right tarsus is a time point at which a foot touches a ground. The analyzing circuitry 1402 outputs, to the generating circuitry 1403, skeleton information in a frame corresponding to the time point at which it is determined that a foot touches the ground.

Note that the above-described example is just an example and a coordinate to be used is not limited to the above-described example. That is, for example, there may be a case where a z coordinate of an ankle or a z coordinate of a knee is used in addition to the z coordinate of the tarsus. Also, for example, there may be a case where comprehensive determination is made by using not only a change in a z coordinate of a single joint but also a change in a z coordinate of each of two joints such as a tarsus and a knee. Also, a coordinate to be used is not limited to a z coordinate. For example, there may be a case where a y coordinate or an x coordinate is used.

For example, in a case of using a y coordinate, the analyzing circuitry 1402 determines whether a foot is on a ground based on a value of a y coordinate (height of each joint) in each joint. That is, the analyzing circuitry 1402 determines that a foot is on the ground when a value of the y coordinate of a joint is equal to or smaller than a predetermined threshold. Note that a predetermined threshold is set arbitrarily for each joint. Also, in a case of using an x coordinate, the analyzing circuitry 1402 determines that a foot is on the ground when a value of an x coordinate is substantially constant. That is, when an object person is walking, a value of the x coordinate of a joint of a foot on the ground does not change much but when the foot is in the air, the value of the x coordinate changes little by little. Thus, the analyzing circuitry 1402 determines that the foot is on the ground when the value of the x coordinate is substantially constant.

Also, there may be a case where determination is made by using a plurality of coordinates in a comprehensive manner. For example, there may be a case where a change in the z coordinate and a change in the y coordinate are analyzed and it is determined whether a foot touches the ground based on analysis results. Also, there may be a case where a predetermined coefficient is added to a value of each coordinate. For example, there may be a case where determination is made after a coefficient "a" is added to a value of the y coordinate.

Also, as described above, in addition to determination of landing of a foot, the analyzing circuitry 1402 can make determination that a foot is in the air. For example, when a change in a value of the z coordinate in a unit time exceeds a predetermined threshold, the analyzing circuitry 1402 determines that the foot is in the air. Also, for example, when a value of the y coordinate exceeds a predetermined threshold, the analyzing circuitry 1402 determines that the foot is in the air. Also, for example, when a value of the x coordinate changes little by little, the analyzing circuitry 1402 determines that the foot is in the air. Then, the analyzing circuitry 1402 determines that an opposite foot of the foot determined to be in the air is on the ground. For example, when a right foot is in the air during walking, the analyzing circuitry 1402 can determine that a left foot is on the ground. Also, by previously inputting coordinates of the ground into a system, the analyzing circuitry 1402 can determine that a foot is on the ground when the foot becomes close to the coordinates of the ground.

As described above, the analyzing circuitry 1402 analyzes a position (coordinate) of a landing point of a foot. Accordingly, for example, the analyzing circuitry 1402 analyzes an overlapped walking distance, a stride, a step interval, the number of steps, a walking rate, walking time, a period of time in which a foot is on the ground, or the like based on the analyzed position of the landing point. That is, the analyzing circuitry 1402 analyzes the above-described various kinds of information by using coordinates of the landing point. Here, the analyzing circuitry 1402 can calculate an overlapped walking distance, a stride, a step interval, or the like with a walking direction as a basis.

Note that in the above-described example, a case where an object person walks in a depth direction (z-axis direction) has been described as an example. However, a walking direction of the object person is arbitrary and the analyzing circuitry 1402 can correspond to the direction. That is, the analyzing circuitry 1402 can analyze a traveling direction of walking by the object person and can determine a landing point of a foot by the above-described method.

Figure 8:
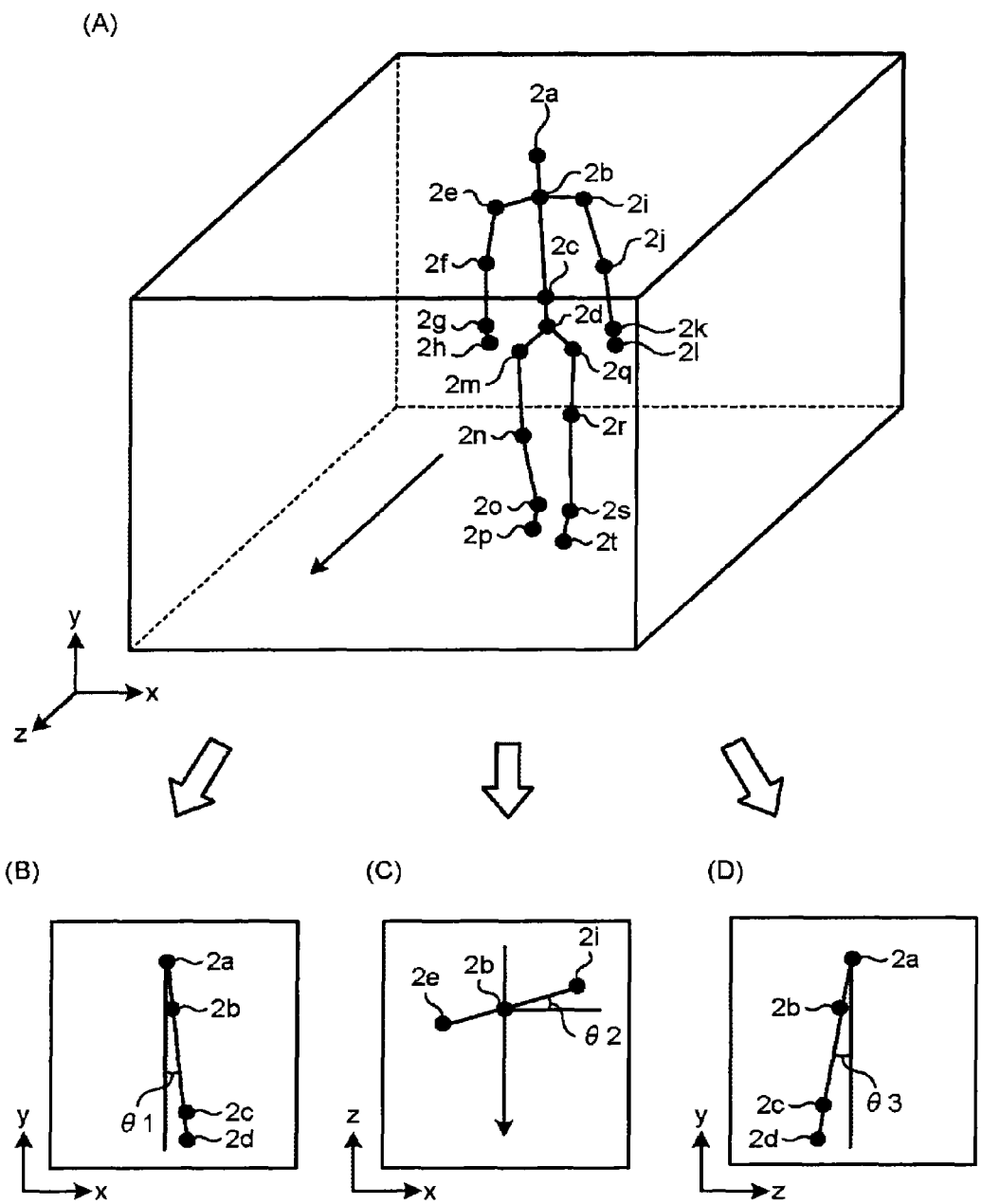
FIG. 8 is a view for describing a first example of an analysis of an angle performed by the analyzing circuitry according to the first embodiment.

Next, a case of analyzing an angle will be described. FIG. 8 is a view for describing a first example of an analysis of an angle performed by the analyzing circuitry 1402 according to the first embodiment. In FIG. 8, a case of calculating an angle of a predetermined part of a body of an object person during walking by using skeleton information in the motion information collected by the motion information collecting circuitry 10 is illustrated. Here, (A) in FIG. 8 is a part illustrating skeleton information in a world coordinate system of an object person executing walking training. Also, (B) to (D) in FIG. 8 are parts illustrating examples of calculation of an angle.

By using the skeleton information in each frame which information is obtained by the obtaining circuitry 1401, the analyzing circuitry 1402 calculates an angle between a predetermined basis and a predetermined part of a body of an object person. For example, as illustrated in (A) in FIG. 8, when the object person executes walking training in a direction of an arrow in the z-axis direction in a predetermined space (space where motion information collecting circuitry 10 can collect coordinate information) in the world coordinate system, the analyzing circuitry 1402 can calculate various angles.

For example, as illustrated in (B) in FIG. 8, the analyzing circuitry 1402 calculates an angle "θ1," in a vertical direction on an xy plane, of an axis (body axis) from the joint "2a" corresponding to a head to a joint "2d" corresponding to a center part of a hip. In such a case, the analyzing circuitry 1402 calculates a straight line which passes through coordinate information (x1, y1) of the joint "2a" corresponding to the head and coordinate information (x4, y4) of the joint "2d" corresponding to the center part of the hip in a predetermined frame and calculates, as the angle "θ1," an angle between the calculated straight line and a straight line which is in parallel with the y-axis. That is, the analyzing circuitry 1402 calculates a degree of an angle to the right/left in a case where the object person is seen from the front (right/left angle of object person).

Also, for example, as illustrated in (C) in FIG. 8, the analyzing circuitry 1402 calculates an angle "θ2," in a horizontal direction on the xz plane, of an axis from the joint "2e" corresponding to a right shoulder to the joint "2i" corresponding to a left shoulder. In such a case, the analyzing circuitry 1402 calculates a straight line which passes through coordinate information (x5, z5) of the joint "2e" corresponding to the right shoulder and coordinate information (x9, z9) of the joint "2i" corresponding to the left shoulder in a predetermined frame and calculates, as the angle "θ2," an angle between the calculated straight line and a straight line which is in parallel with an x-axis. That is, the analyzing circuitry 1402 calculates a degree of shaking of a body in a rotation direction centering on a body axis in a case where the object person is seen from the above.

Also, for example, as illustrated in (D) in FIG. 8, the analyzing circuitry 1402 calculates an angle "θ3," in a vertical direction on a yz plane, of an axis (body axis) from the joint "2a" corresponding to the head to the joint "2d" corresponding to the center part of the hip. In such a case, the analyzing circuitry 1402 calculates a straight line which passes through coordinate information (y1, z1) of the joint "2a" corresponding to the head and coordinate information (y4, z4) of the joint "2d" corresponding to the center part of the hip in a predetermined frame and calculates, as the angle "θ3," an angle between the calculated straight line and a straight line which is in parallel with the y-axis. That is, the analyzing circuitry 1402 calculates a degree of an angle to the right/left in a case where the object person is seen from a side (forward/backward angle of object person).

Also, the analyzing circuitry 1402 can use, as a predetermined basis, a part of a body of the object person. FIG. 9 is a view for describing a second example of an analysis of an angle performed by the analyzing circuitry 1402 according to the first embodiment. In FIG. 9, a case of calculating an angle between a part of a body of an object person and a predetermined part of the body of the object person during walking by using skeleton information in the motion information collected by the motion information collecting circuitry 10 is illustrated. Here, (A) in FIG. 9 is a part illustrating skeleton information in a world coordinate system of an object person executing walking training. Also, (B) in FIG. 9 is a part illustrating examples of calculation of an angle.

By using skeleton information in each frame which information is obtained by the obtaining circuitry 1401, the analyzing circuitry 1402 calculates an angle between a part of a body of the object person and a predetermined part of the body of the object person. For example, as illustrated in (A) in FIG. 9, when the object person executes walking training in a direction of an arrow in a z-axis direction in a predetermined space (space where motion information collecting circuitry 10 can collect coordinate information) in the world coordinate system, the analyzing circuitry 1402 can calculate various angles between a part of the body of the object person and a predetermined part of the body of the object person.

For example, as illustrated in (B) in FIG. 9, the analyzing circuitry 1402 calculates an angle "θ4" between a bone, which connects the joint "2e" corresponding to a right shoulder and the joint "2f" corresponding to a right elbow, and a bone which connects the joint "2f" corresponding to the right elbow and the joint "2g" corresponding to a right wrist. That is, the analyzing circuitry 1402 analyzes an angle of a right arm (right elbow) of the object person in a walking motion. In such a case, the analyzing circuitry 1402 calculates a straight line which passes through coordinate information (x5, y5, z5) of the joint "2e" corresponding to the right shoulder and coordinate information (x6, y6, z6) of the joint "2f" corresponding to the right elbow in a predetermined frame. Moreover, the analyzing circuitry 1402 calculates a straight line which passes through the coordinate information (x6, y6, z6) of the joint "2f" corresponding to the right elbow and coordinate information (x7, y7, z7) of the joint "2g" corresponding to the right wrist. Then, the analyzing circuitry 1402 calculates, as the angle "θ4," an angle between the two calculated straight lines.

In such a manner, by using coordinate information (x, y, z) of skeleton information in each frame which information is collected by the motion information collecting circuitry 10, the analyzing circuitry 1402 can calculate an angle between a predetermined basis and a predetermined part of the object person. Here, each of the examples illustrated in (B) to (D) in FIG. 8 and (B) in FIG. 9 is just an example. That is, the analyzing circuitry 1402 can calculate an angle between a basis set arbitrarily by an operator and an arbitrarily-selected part of a body in each frame.

Here, an angle to be calculated can be set arbitrarily as described above. For example, it is possible to perform setting in such a manner that an angle prescribed in a "range of joint motion display and measurement method (The Japan Orthopaedic Association and The Japanese Association of Rehabilitation Medicine): http://ci.nii.ac.jp/naid/110001856130" is calculated. Also, for example, a reference plane on a body (sagittal plane, horizontal plane, or frontal plane) can be used as a set basis. Also, for example, it is possible to preset an initial state of an object person as a basis and to analyze a difference between a state during walking and the initial state.

Next, a case of analyzing velocity will be described. When analyzing velocity, the analyzing circuitry 1402 calculates a moving distance [m] of a coordinate corresponding to a predetermined part of the object person in each predetermined period of time (such as 0.5 second). Then, based on the calculated moving distance in the predetermined period of time, the analyzing circuitry 1402 calculates moving velocity [m/second] of the object person in the predetermined period of time. Here, the analyzing circuitry 1402 can also calculate, as velocity of walking of the object person, an average value of moving velocity of the object person during walking training. For example, the analyzing circuitry 1402 calculates moving velocity of a part instructed by the operator through the input circuitry 120 (such as any of joints or part of body lead from each joint).

Also, the analyzing circuitry 1402 calculates acceleration by using the calculated velocity. More specifically, the analyzing circuitry 1402 calculates acceleration (change rate of velocity in unit time) by using velocity in a unit time which velocity is calculated by the above-described method.

As described above, the analyzing circuitry 1402 executes various kinds of analysis by using skeleton information of the object person in each frame which information is obtained by the obtaining circuitry 1401. Here, the analyzing circuitry 1402 can execute the above-described analysis automatically or according to an operation by the operator. Also, by using an analysis result, the analyzing circuitry 1402 determines whether walking by the object person is walking which satisfies a predetermined basis (stable walking). Then, the analyzing circuitry 1402 outputs a determination result to the display controlling circuitry 1404. Note that the determination performed by the analyzing circuitry 1402 will be described later. Moreover, the analyzing circuitry 1402 can execute measurement of a distance or the like as an analysis executed according to an operation by the operator. Note that the measurement of a distance performed by the analyzing circuitry 1402 will be described in detail in the following.

Referring back to FIG. 4, according to control performed by the display controlling circuitry 1404 described later, the generating circuitry 1403 generates display information to be displayed on the output circuitry 110. More specifically, based on the motion information obtained by the obtaining circuitry 1401, the generating circuitry 1403 generates track information indicating a position of a landing point of a foot of the object person. Also, the generating circuitry 1403 generates superimposed image information in which information of an angle of a predetermined part of a body of the object person is superimposed on color image information. Here, an angle of a predetermined part is at least one of a rotation angle indicating forward/backward shaking in a traveling direction of the object person and a rotation angle indicating shaking in an upward/downward direction of the object person. In other word, an angle of a predetermined part is a rotation angle around an axis in a vertical direction and a rotation angle around an axis in a traveling direction.

Moreover, based on the motion information obtained by the obtaining circuitry 1401, the generating circuitry 1403 generates track information indicating a track of a movement of the object person in addition to a track of a position of a landing point of a foot. Here, the track of the movement of the object person is a movement track of a feature position of the object person. Also, the feature position is at least one of a position of a predetermined part of the object person, a position calculated by using positions of a plurality of parts, a plurality of center positions of the object person, and a position of a center of gravity of the object person. In the following, generation of track information and generation of superimposed image information will be described serially. First, in the generation of the track information, the generating circuitry 1403 generates track information by using information such as an analysis result of a "landing point of a foot" which information is analyzed by the analyzing circuitry 1402 and stored in the analysis information storage circuitry 1302.

FIG. 10A to FIG. 10G are graphs for describing variations of track information generated by the generating circuitry 1403 according to the first embodiment. In each of FIG. 10A to FIG. 10G, a graph two-dimensionally illustrating a landing point of a foot and a track of a movement of a body in a space where the motion information collecting circuitry 10 can collect motion information is illustrated. That is, in each of FIG. 10A to FIG. 10G, a graph of when a footprint and a track of a movement of a body are seen from the above (graph illustrating footprint and track of body on xz plane in coordinate space in (A) in FIG. 8) is illustrated. Note that in FIG. 10A to FIG. 10G, description will be made by using track information of when walking is illustrated in a vertical direction but an embodiment is not limited thereto. For example, track information of when walking is illustrated in a horizontal direction or when walking is illustrated in a bird's eye view may be used.

Here, in each of FIG. 10A to FIG. 10G, when the object person executes walking training on a straight line, track information is illustrated in a region of one meter to each of the right and the left with a walked line as a center and four meters in a walking direction. Note that this region can be set arbitrarily as long as a size of an area where the motion information collecting circuitry 10 acquires motion information is not exceeded. Also, in each of FIG. 10A to FIG. 10G, a case where walking is started on an upper side in track information illustrated in each graph is illustrated.

Figure 10A:
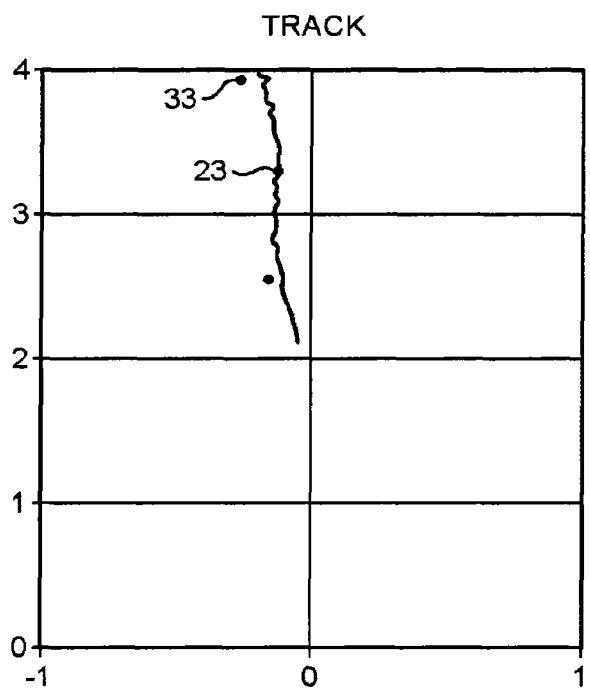
FIG. 10A is a graph for describing a variation of track information generated by generating circuitry according to the first embodiment.

For example, as illustrated in FIG. 10A, the generating circuitry 1403 illustrates, in a region of four meters by two meters, xz coordinates in the world coordinate system where the object person executes walking training. Then, the generating circuitry 1403 generates, in the region, track information indicating a foot print 33 of the object person and a track 23 of a body of the object person. In a case of generating the information, the generating circuitry 1403 first acquires, from the analysis information storage circuitry 1302, information of a landing point of a foot of the object person which information is analyzed by the analyzing circuitry 1402. Then, the generating circuitry 1403 acquires information at a time point at which a foot of the object person touches a ground from the acquired information of a landing point of a foot of the object person.

Moreover, the generating circuitry 1403 acquires, from the motion information storage circuitry 1301, values of coordinates of the joint "2p" corresponding to the right tarsus and values of coordinates of the joint "2t" corresponding to the left tarsus at the time point of acquisition. That is, the generating circuitry 1403 acquires coordinate information of each of the joints "2p" and "2t" from skeleton information in a frame corresponding to the time point at which the foot touches the ground. Then, the generating circuitry 1403 generates track information in which each of the acquired coordinates (x16, z16) of the joint "2p" corresponding to the right tarsus and the acquired coordinates (x20, z20) of the joint "2t" of the left tarsus is illustrated as a point on xz coordinates in a region of four meters by two meters.

The generating circuitry 1403 executes the above-described processing each time a right foot or a left foot of the object person touches the ground while the object person executes walking training and generates track information in which a landing point of a foot of the object person of when the object person performs the walking training is illustrated as a point.

Moreover, the generating circuitry 1403 generates, on xz coordinates in the region of four meters by two meters, track information indicating a track of a movement of a predetermined part of the object person during walking. That is, as illustrated in FIG. 10A, the generating circuitry 1403 generates track information indicating the track 23 of movement of the predetermined part (such as center of body) of the object person. In such a case, the generating circuitry 1403 acquires coordinate information in each frame of a part, a movement track of which is to be acquired, and generates the track 23 from the acquired coordinate information. For example, the generating circuitry 1403 acquires coordinate information in each frame of a center of an upper body (calculated, for example, from joint corresponding to both shoulder and joint corresponding to loin) and generates, from the acquired coordinate information (x, z) in each frame, track information in which a track of a movement of a body is illustrated as a curved line.

As described above, based on the skeleton information obtained by the obtaining circuitry 1401 and the analysis result from the analyzing circuitry 1402, the generating circuitry 1403 generates track information indicating a foot print and a track of a movement of the object person executing the walking training. Here, the generating circuitry 1403 can generate track information with various variations. In the following, with reference to FIG. 10B to FIG. 10G, variations of the track information will be described.

Figure 10B:
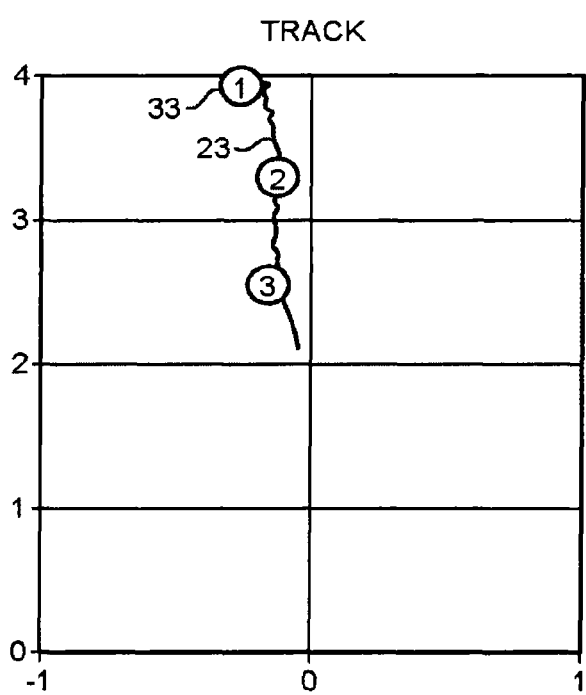
FIG. 10B is a graph for describing a variation of track information generated by the generating circuitry according to the first embodiment.

For example, as illustrated in FIG. 10B, the generating circuitry 1403 can generate track information in which a landing point of a foot (in the following, also referred to as foot print) is indicated by a circle numbered by an order of a stepping foot. That is, as illustrated in FIG. 10B, the generating circuitry 1403 generates track information indicating that walking is performed in an order of a first step, a second step, and a third step from a direction in the drawing.

Figure 10C:
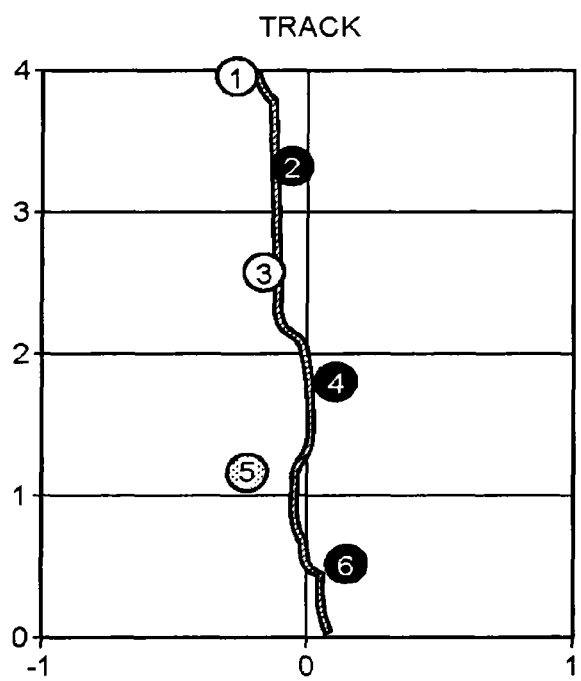
FIG. 10C is a graph for describing a variation of track information generated by the generating circuitry according to the first embodiment.

Also, for example, as illustrated in FIG. 10C, the generating circuitry 1403 can generate track information indicating which foot is put forward. That is, as illustrated in FIG. 10C, the generating circuitry 1403 can generate track information in which foot prints of the right foot and foot prints of the left foot are illustrated in different colors, the foot prints of the right foot which are a first step, a third step, and a fifth step being illustrated with outlined circles and the foot prints of the left foot which are a second step, a fourth step, and a sixth step being illustrated with black circles.

Here, for example, as illustrated in FIG. 10C, the generating circuitry 1403 can generate track information in which a foot print of when a body shakes or loses a balance is emphasized. For example, as illustrated in FIG. 10C, the generating circuitry 1403 can generate track information in which a fifth foot print is emphasized.

Also, the generating circuitry 1403 can generate track information corresponding to a period of time in which a foot of the object person is on the ground. For example, the generating circuitry 1403 generates track information in which a size of a foot print is increased in proportion to landing time or track information in which a color of a foot print is made thicker in proportion to landing time.

Figure 10D:
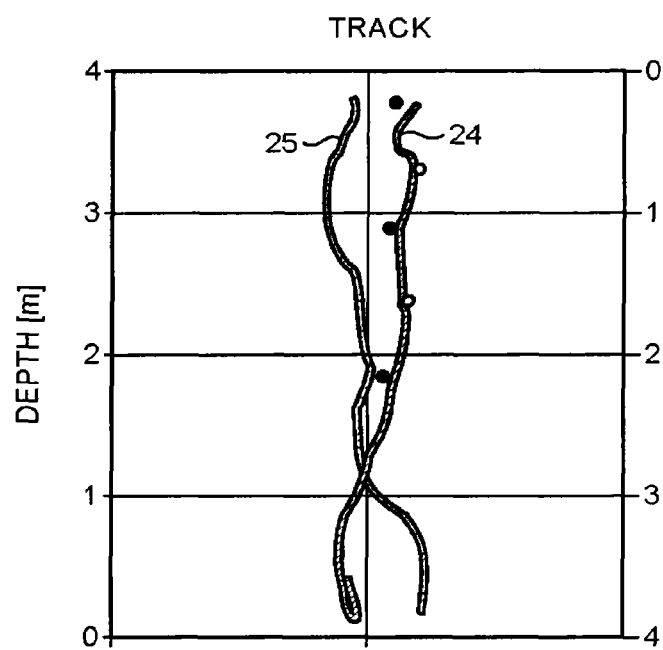
FIG. 10D is a graph for describing a variation of track information generated by the generating circuitry according to the first embodiment.

Also, for example, as illustrated in FIG. 10D, the generating circuitry 1403 can generate track information indicating a plurality of tracks of parts of a body of the object person. For example, as illustrated in FIG. 10D, the generating circuitry 1403 can generate track information indicating each of a track 24 which is a trace of a center of an upper body and a track 25 which is a trace of a right shoulder. In such a case, the generating circuitry 1403 acquires coordinate information of a center of an upper body and coordinate information of a joint "2e" corresponding to a right shoulder in all frames and generates each track from the acquired coordinate information.

Figure 10E:
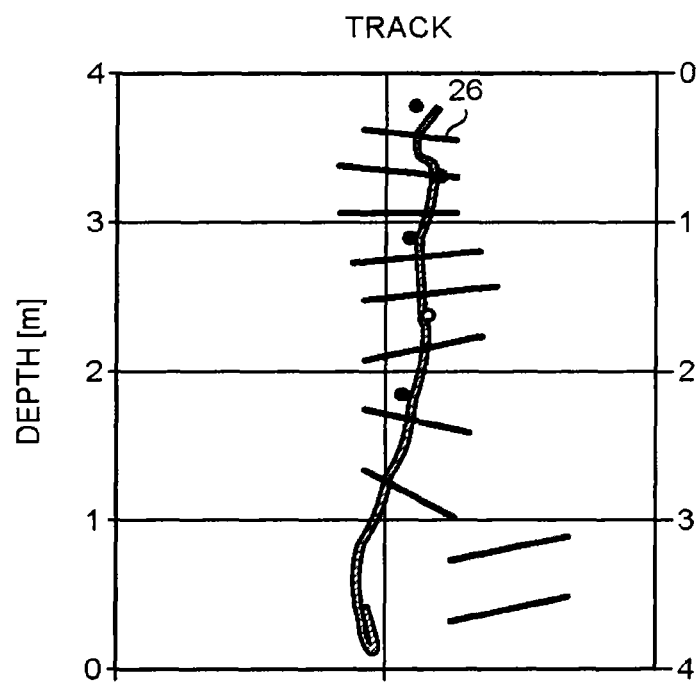
FIG. 10E is a graph for describing a variation of track information generated by the generating circuitry according to the first embodiment.

Also, for example, as illustrated in FIG. 10E, the generating circuitry 1403 can generate track information indicating an angle of a predetermined part of the body of the object person who executes walking training. For example, as illustrated in FIG. 10E, the generating circuitry 1403 can generate track information indicating a straight line 26 which connects a position of the joint "2e" corresponding to the right shoulder and a position of the joint "2*i*" corresponding to the left shoulder. Here, the generating circuitry 1403 acquires coordinate information of the joint "2*e*" corresponding to the right shoulder in each frame and coordinates of the joint "2*i*" corresponding to the left shoulder in each frame and calculates a straight line which connects joints in each frame.

Then, the generating circuitry 1403 extracts a straight line in each predetermined period of time and generates track information indicating the extracted straight line. That is, the straight line 26 illustrated in FIG. 10E is information indicating a segment which connects joints of the right shoulder and the left shoulder in each predetermined period of time. Note that a part indicated by the track information is selected arbitrarily. For example, there is a case where an angle of a head, a chest, or a loin is illustrated other than the segment which connects the right shoulder and the left shoulder which segment is illustrated in FIG. 10E.

Here, track information illustrated in FIG. 10E is an example of an angle in a traveling direction in walking. The generating circuitry 1403 can generate track information indicating a different angle. For example, the generating circuitry 1403 can generate track information indicating an angle in a horizontal direction. That is, the generating circuitry 1403 generates track information indicating information of an angle in the horizontal direction in FIG. 10E. For example, the generating circuitry 1403 generates track information in which a lower side in a horizontal direction of a straight line, which indicates an angle, is indicated in blue and an upper side thereof is indicated in read. Here, for example, the generating circuitry 1403 generates track information in a horizontal direction with a center of a body as a basis. When description is made by using the straight line 26 in FIG. 10E, the generating circuitry 1403 generates track information in which a lower side, in a horizontal direction with a center point of a body as a basis, of the straight line 26 is indicated in blue and an upper side thereof is indicated in red.

Figure 10F:
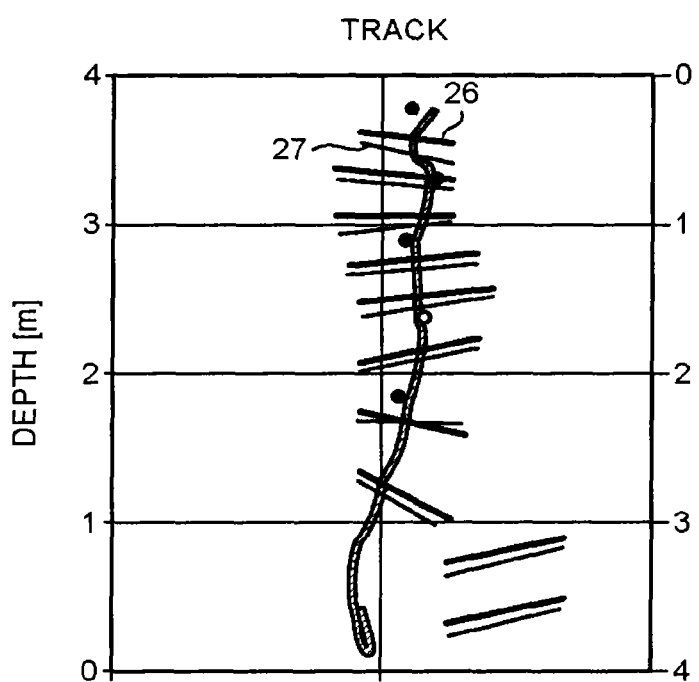
FIG. 10F is a graph for describing a variation of track information generated by the generating circuitry according to the first embodiment.

Also, there may be a case where two or more of the above-described angles are indicated simultaneously. For example, as illustrated in FIG. 10F, the generating circuitry 1403 can generate track information indicating a straight line 27 which connects a joint "2*m*" corresponding to a right hip and a joint "2*q*" corresponding to a left hip in addition to the straight line 26 which connects the joint "2*e*" corresponding to the right shoulder and the joint "2*i*" corresponding to the left shoulder.

Here, there may be a case where the generating circuitry 1403 displays the straight line 26 and the straight line 27 in an overlapped manner according to coordinates. Alternatively, as illustrated in FIG. 10F, it is also possible to generate track information by adding a predetermined coefficient to each of coordinate information of the joint "2*m*" corresponding to the right hip and coordinate information of the joint "2*q*" corresponding to the left hip in such a manner that the straight line 26 and the straight line 27 are separated from each other on the xz coordinates. Also, when generating a plurality of straight lines, the generating circuitry 1403 can generate track information indicating a straight line not only on the xz coordinates but also, for example, on xy coordinates or yz coordinates.

Also, when generating a plurality of straight lines, the generating circuitry 1403 can generate track information in which colors of the straight lines are changed. For example, the generating circuitry 1403 can generate track information which is illustrated in FIG. 10F and in which the straight line 26 is indicated in red and the straight line 27 is indicated in blue.

As described above, the generating circuitry 1403 can generate various kinds of track information. Here, it is possible to perform setting in such a manner that track information in a certain period of time is generated as each piece of track information. That is, the generating circuitry 1403 can generate not only track information including all pieces of information during execution of walking training but also track information in a certain period of time, for example, in a case where the walking training is performed for a long period of time. For example, the generating circuitry 1403 generates track information indicating a track of walking by the object person in 30 seconds. That is, when 30 seconds passes after the object person starts walking training, the generating circuitry 1403 deletes information in previous 30 seconds from a current time point and serially updates track information to which new information is added. Accordingly, for example, it is possible to control various kinds of information included in track information from becoming complicated.

Figure 10G:
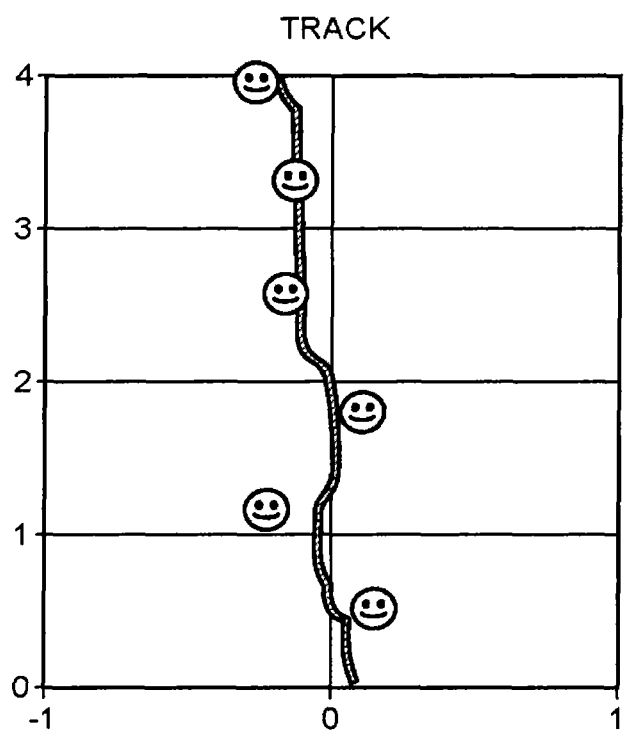
FIG. 10G is a graph for describing a variation of track information generated by the generating circuitry according to the first embodiment.

Also, the generating circuitry 1403 can generate track information in which information such as a foot print, a focus point, or a linear track is indicated not only with a simple point, a number, or a line but also with various characters. For example, as illustrated in FIG. 10G, the generating circuitry 1403 can generate track information in which a foot print of the object person is indicated with a smiley mark.

In the above, a case where the generating circuitry 1403 generates track information as display information has been described. Note that the above-described track information is just an example. Information included in the track information can be set arbitrarily. For example, it is also possible to arbitrarily set information included in track information based on an instruction to display/not to display the track information displayed on the output circuitry 110 according to control by the display controlling circuitry 1404 described later. For example, each of a foot print and a track of a movement of a body in the track information is displayed or not displayed.

Also, track information illustrated in each of FIG. 10A to 10G is just an example. Various different kinds of track information can be generated and displayed. For example, as illustrated in FIG. 7B, it is possible to generate graph information, in which a position of a landing point of a right/left foot of an object person is indicated on a graph with one axis as a position of the object person and the other axis as time in a walking motion, based on motion information obtained by the obtaining circuitry 1401.

Figure 11:
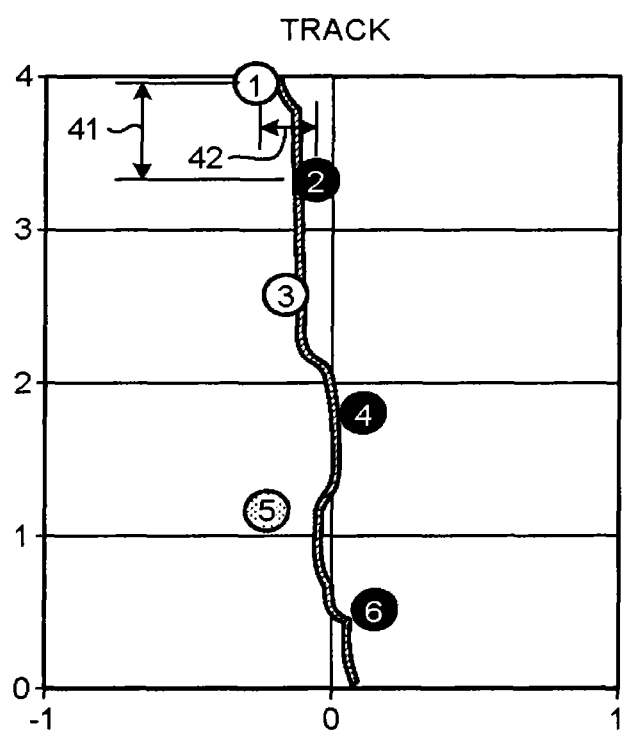
FIG. 11 is a graph for describing an example of measurement processing performed by the analyzing circuitry according to the first embodiment.

Here, in the track information generated by the generating circuitry 1403, it is possible to measure a distance or the like by a measurement function of the analyzing circuitry 1402. FIG. 11 is a graph for describing an example of measurement processing performed by the analyzing circuitry 1402 according to the first embodiment.

For example, as illustrated in FIG. 11, the analyzing circuitry 1402 calculates a distance of a stride 41 or a step interval 42. For example, when track information illustrated in FIG. 11 is displayed on the output circuitry 110 and an operator inputs a measurement request of each distance through the input circuitry 120, the analyzing circuitry 1402 calculates the stride 41 based on a value of a z coordinate in coordinate information corresponding to a first step and a value of a z coordinate in coordinate information corresponding to a second step. Similarly, the analyzing circuitry 1402 calculates the step interval 42 based on a value of an x coordinate in the coordinate information corresponding to the first step and a value of an x coordinate in the coordinate information corresponding to the second step.

Note that the above-described example is just an example and it is possible to arbitrarily execute measurement of a distance. For example, with the measurement function of the analyzing circuitry 1402, it is possible to calculate a distance from a foot print of a first step to a foot print of a second step based on values of an x coordinate and a z coordinate in coordinate information corresponding to the first step and values of an x coordinate and a z coordinate in coordinate information corresponding to the second step. Also, measurement processing by the above-described analyzing circuitry 1402 can be performed according to an instruction from an operator or can be performed automatically.

Next, a case where the generating circuitry 1403 generates image information as display information will be described. In such a case, first, the obtaining circuitry 1401 further obtains color image information stored in the motion information storage circuitry 1301. More specifically, when acquiring skeleton information of a predetermined object person automatically or according to an instruction from the operator, the obtaining circuitry 1401 obtains color image information corresponding to the object person from the motion information storage circuitry 1301.

Then, the generating circuitry 1403 generates superimposed image information in which various kinds of information are superimposed on the color image information generated by the obtaining circuitry 1401. More specifically, the generating circuitry 1403 generates superimposed image information in which information of an angle between a predetermined basis and a predetermined part of a body of the object person is superimposed on the color image information.

Figure 12B:
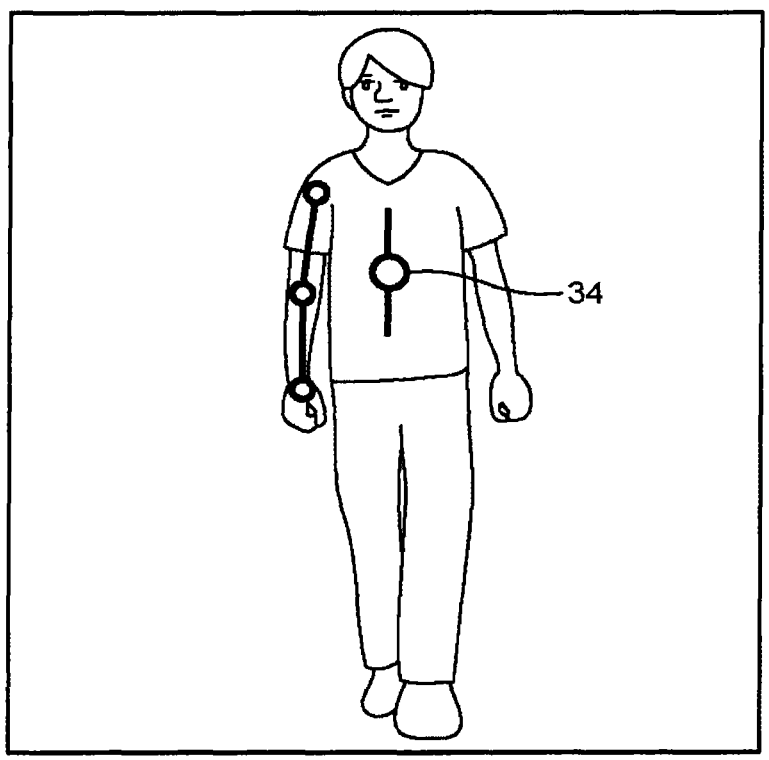
FIG. 12B is a view for describing a variation of superimposed image information generated by the generating circuitry according to the first embodiment.
Figure 12C:
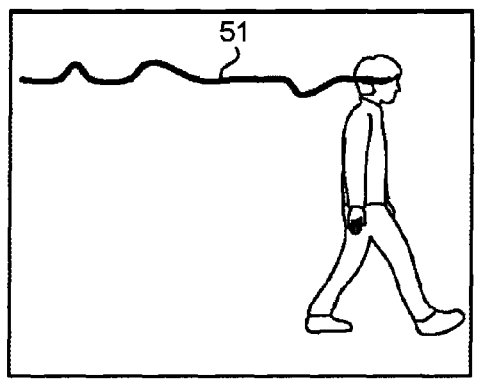
FIG. 12C is a view for describing a variation of superimposed image information generated by the generating circuitry according to the first embodiment.
Figure 12D:
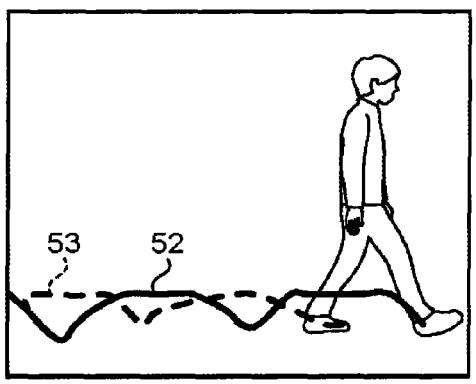
FIG. 12D is a view for describing a variation of superimposed image information generated by the generating circuitry according to the first embodiment.
Figure 12E:
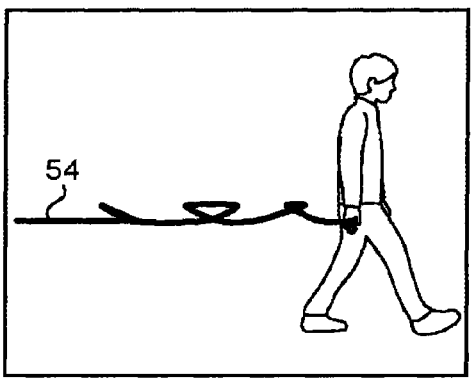
FIG. 12E is a view for describing a variation of superimposed image information generated by the generating circuitry according to the first embodiment.
Figure 12F:
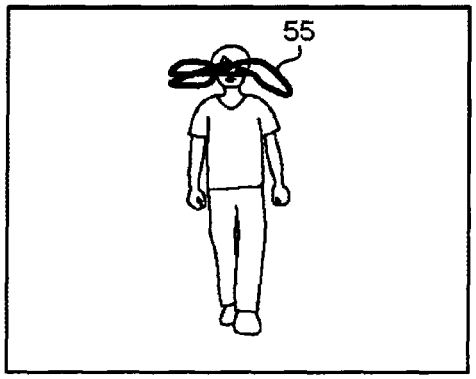
FIG. 12F is a view for describing a variation of superimposed image information generated by the generating circuitry according to the first embodiment.
Figure 12G:
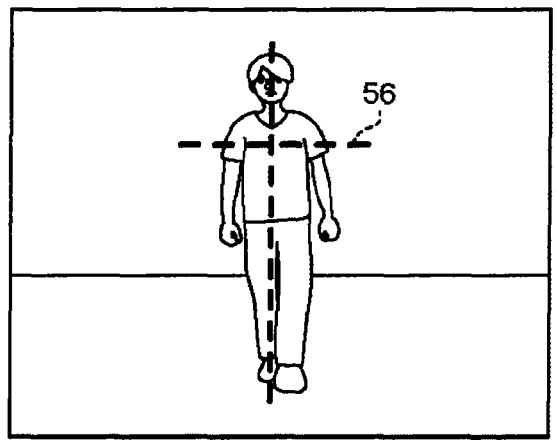
FIG. 12G is a view for describing a variation of superimposed image information generated by the generating circuitry according to the first embodiment.
Figure 12H:
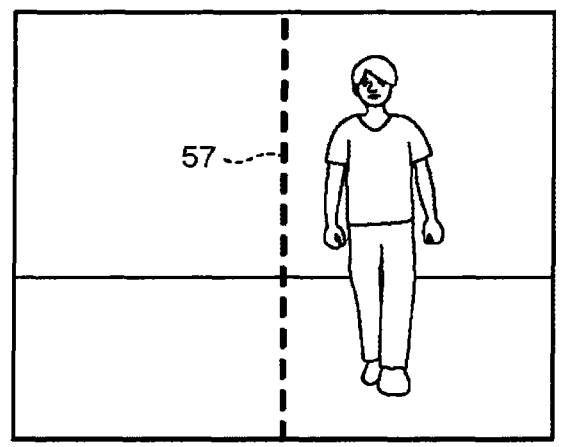
FIG. 12H is a view for describing a variation of superimposed image information generated by the generating circuitry according to the first embodiment.
Figure 12I:
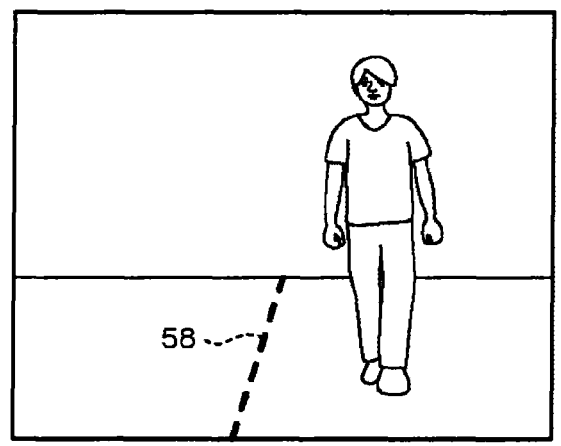
FIG. 12I is a view for describing a variation of superimposed image information generated by the generating circuitry according to the first embodiment.
Figure 12J:
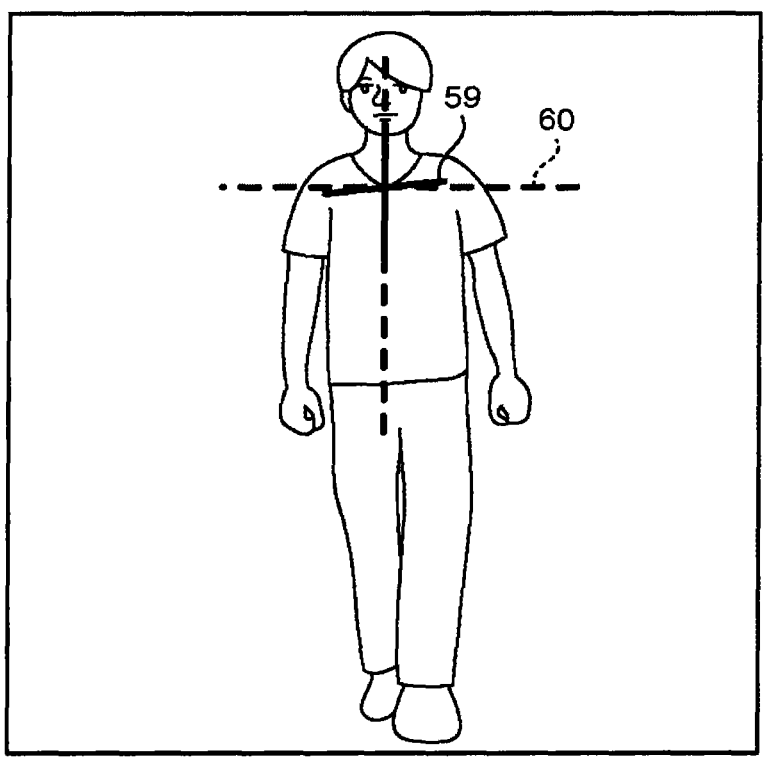
FIG. 12J is a view for describing a variation of superimposed image information generated by the generating circuitry according to the first embodiment.
Figure 12K:
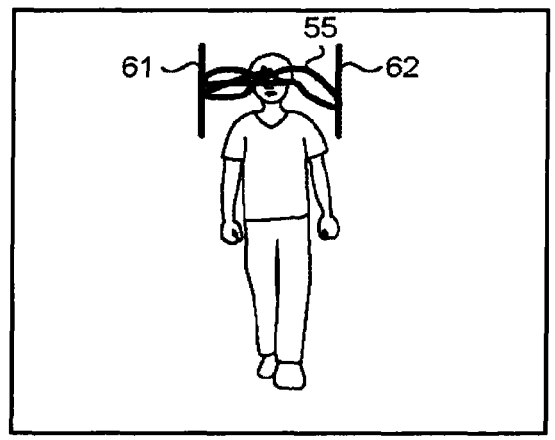
FIG. 12K is a view for describing a variation of superimposed image information generated by the generating circuitry according to the first embodiment.
Figure 12L:
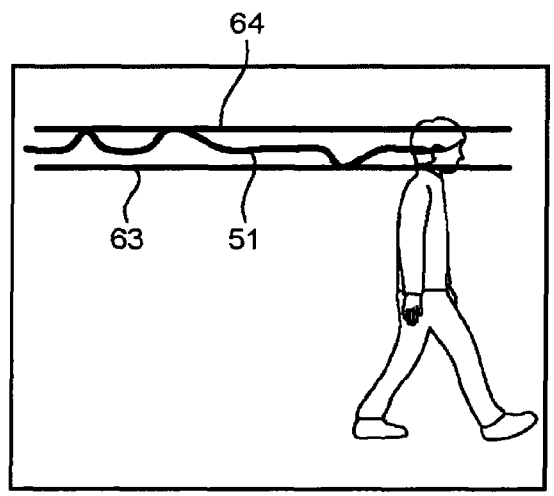
FIG. 12L is a view for describing a variation of superimposed image information generated by the generating circuitry according to the first embodiment.
Figure 12M:
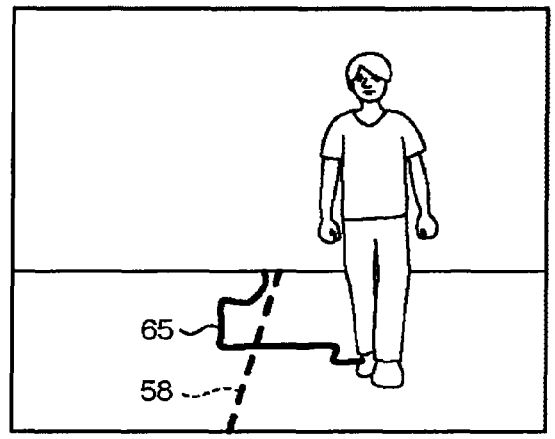
FIG. 12M is a view for describing a variation of superimposed image information generated by the generating circuitry according to the first embodiment.
Figure 12N:
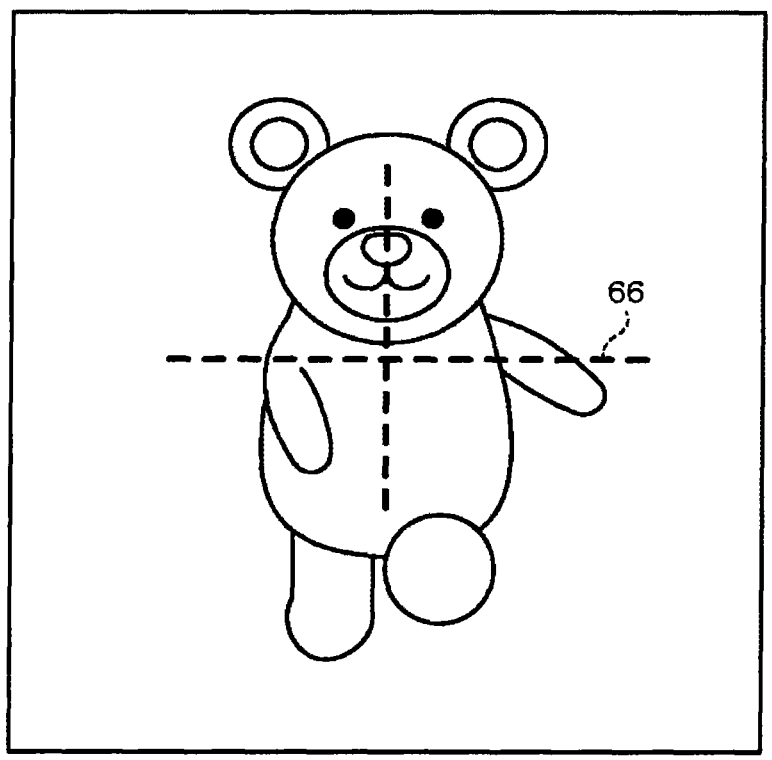
FIG. 12N is a view for describing a variation of superimposed image information generated by the generating circuitry according to the first embodiment.

FIG. 12A to FIG. 12N are views for describing variations of superimposed image information generated by the generating circuitry 1403 according to the first embodiment. For example, as illustrated in (A) in FIG. 12A, the generating circuitry 1403 generates superimposed image information in which a straight line 28 indicating an angle of the object person is superimposed on color image information in which the object person walks to the front in the drawing. Here, in (A) in FIG. 12A, a straight line which connects a joint corresponding to a head and a joint corresponding to a loin is illustrated. For example, as illustrated in (B) in FIG. 12A, the generating circuitry 1403 generates superimposed image information indicating an angle of the object person during walking. The operator can observe an angle of the straight line 28 in a vertical direction in the superimposed image information generated by the generating circuitry 1403.

Note that the example illustrated in (B) in FIG. 12A is just an example. The generating circuitry 1403 can generate superimposed image information in which a straight line which connects arbitrary positions of the object person (such as joint or predetermined position of predetermined bone) is superimposed on the color image information. For example, as illustrated in (C) in FIG. 12A, the generating circuitry 1403 can generate superimposed image information in which a straight line 29 which connects a joint corresponding to a right shoulder and a joint corresponding to a left shoulder is superimposed on the color image information. Accordingly, the operator can observe, for example, an angle of the straight line 29 in a horizontal direction.

Also, as illustrated in FIG. 12B, the generating circuitry 1403 can generate superimposed image information in which information, which indicates a point corresponding to a predetermined joint and a straight line (bone) to connect points, or an arbitrary position in the object person which position is calculated from a position of a joint is superimposed on the color image information. For example, as illustrated in FIG. 12B, the generating circuitry 1403 generates superimposed image information in which information of a segment which connects a point indicating a joint corresponding to a right shoulder, a point indicating a joint corresponding to a right elbow, and a point indicating a joint corresponding to a right wrist and information of a point 34 calculated as a center point between a joint position of a center of both shoulders and a joint position of a loin are superimposed on the color image information.

Here, the example illustrated in FIG. 12B is just an example and a point or a segment superimposed on the color image information can be set arbitrarily by the operator. That is, the operator can generate superimposed image information in which information of a joint at an intended position and that of a segment which connects joints are superimposed on the color image information. For example, the generating circuitry 1403 can generate superimposed image information in which a point and a segment are superimposed on a skeleton of each of lower limbs (such as right tarsus, right ankle, right knee, right hip, loin, left hip, left knee, left ankle, or left tarsus).

Also, as illustrated in FIG. 12C to FIG. 12F, the generating circuitry 1403 can generate superimposed image information in which a track of a predetermined position of the object person (such as joint or predetermined position of predetermined bone) during walking is superimposed on the color image information. Here, in each of FIG. 12C to FIG. 12E, a case of superimposing a track on color image information in which the object person walks from the left to the right in the drawing is illustrated. Also, in FIG. 12F, a case where the object person moves in a depth direction is illustrated. For example, as illustrated in FIG. 12C, the generating circuitry 1403 generates superimposed image information in which a track 51 indicating a temporal change in a position (coordinate) of a joint corresponding to a head on the color image information.

Also, the generating circuitry 1403 can generate superimposed image information in which a plurality of tracks of different positions is superimposed on the color image information. For example, as illustrated in FIG. 12D, the generating circuitry 1403 generates superimposed image information in which a track 52 indicating a temporal change in a position (coordinate) of a joint corresponding to a right tarsus and a track 53 indicating a temporal change in a position (coordinate) of a joint corresponding to a left tarsus are superimposed on the color image information. Here, by changing colors or thicknesses of the track 52 and the track 53 from each other, the generating circuitry 1403 generates superimposed image information with which it is possible to easily distinguish the track 52 and the track 53 from each other.

Similarly, as illustrated in FIG. 12E, the generating circuitry 1403 can also generate superimposed image information in which a track 54 indicating a temporal change in a position (coordinate) of a joint corresponding to a right hand is superimposed on the color image information. Here, each of the examples illustrated in FIG. 12C to FIG. 12E is just an example. A direction of the object person on which a track of is superimposed is arbitrary. That is, as illustrated in FIG. 12F, the generating circuitry 1403 can also generate superimposed image information in which a track 55 indicating a temporal change in a position (coordinate) of a joint corresponding to a head is superimposed on color image information in which the object person moves in the depth direction. Here, the generating circuitry 1403 can also superimposes a track, a thickness of which is changed, on the color image information. For example, in FIG. 12F, the generating circuitry 1403 can perform generation in such a manner that the track 55 becomes narrower along with a depth. That is, the generating circuitry 1403 can generate superimposed image information in which the track 55 which becomes thick as a depth becomes shallow is superimposed on color image information in which the object person walks to the front in the drawing.

As described above, the generating circuitry 1403 can generate superimposed image information in which information of a predetermined position of the object person is superimposed on the color image information. Here, the generating circuitry 1403 can also generate superimposed image information in which information of a basis is superimposed not only on the object person but also on a color image. For example, as illustrated in FIG. 12G, the generating circuitry 1403 generates superimposed image information in which a cross 56 indicating a basis is superimposed on color image information in the object person walks to the front in the drawing. Here, the generating circuitry 1403 generates a dotted line in a horizontal direction (horizontal line which passes through midpoint of both shoulder of object person) in the cross 56 based on information in the horizontal direction (horizontal component) which information is included in the color image information. Similarly, the generating circuitry 1403 generates a dotted line in a vertical direction (vertical line which passes through midpoint of joint corresponding to head of object person and joint corresponding to loin thereof) in the cross 56 based on information in the vertical direction (vertical component) which information is included in the color image information.

Note that in FIG. 12G, a case of using the cross 56 as a basis has been described but an embodiment is not limited thereto. For example, there may be a case where only a horizontal line or a vertical line is used. Also, there may be a case of generating a straight line to be a basis in a depth direction. Also, a basis is not limited to that in a horizontal direction, a vertical direction, or a depth direction. The operator can set an arbitrary basis. Accordingly, it is possible to understand a state of the object person during walking at a glance. Also, by generating a basis in such a manner that the basis passes through a predetermined position of the object person, a position of a basis (such as cross 56) also moves in response to movement of the object person when an image of walking by the object person is displayed. Thus, it is possible to understand a state of the object person with respect to the basis constantly.

In FIG. 12G, a basis is generated in such a manner as to pass through a predetermined position of the object person but an embodiment is not limited thereto. For example, as illustrated in FIG. 12H, the generating circuitry 1403 can generate superimposed image information in which a dotted line 57 to be a basis is superimposed on a center of the color image information. Also, as illustrated in FIG. 12I, the generating circuitry 1403 can generate superimposed image information in which a dotted line 58 to be a basis is superimposed on a floor on a screen. Accordingly, for example, the operator can observe whether the object person walks straight with respect to a screen of when the color image information is displayed or whether the object person walks straight with respect to a basis on the floor.

Also, the generating circuitry 1403 can generate superimposed image information in which information indicating a predetermined position of the object person (such as point or straight line) and information indicating a basis (such as dotted line illustrated in FIG. 12G to FIG. 12I) are superimposed on an identical piece of color image information. For example, as illustrated in FIG. 12J, the generating circuitry 1403 generates superimposed image information in which a cross 60 indicating a basis and a cross 59 indicating an angle of the object person are superimposed on color image information in which the object person walks to the front in the drawing.

In such a case, the generating circuitry 1403 generates a segment which connects the joint "2a" corresponding to the head and the joint "2c" corresponding to the loin and a segment which connects the joint "2e" corresponding to the right shoulder and the joint "2i" corresponding to the left shoulder. Also, as described in FIG. 12G, the generating circuitry 1403 generates the cross 60 by using a horizontal component and a vertical component included in the color image information. Note that generation of the cross 60 is not limited to the above-described example. For example, the generating circuitry 1403 can generate a cross 60 in which an intersection point of segments and an intersection point of coordinates are identical. That is, the generating circuitry 1403 generates a cross 60 in which a segment in a vertical direction and a segment in a horizontal direction intersect with each other at a position identical to an intersection point of segments which connect joints.

Accordingly, the generating circuitry 1403 generates superimposed image information in which an angle of the object person with respect to the cross 60 which is the basis is expressed by the cross 59. The generating circuitry 1403 generates superimposed image information in each frame by using color image information and skeleton information in each frame. That is, by successively displaying superimposed image information in each frame, the operator can observe in what degree the object person in the walking training is inclined from the basis in a video. Note that in the example in FIG. 12J, the cross 60 and the cross 59 are illustrated but an embodiment is not limited thereto. Superimposition can be performed with an arbitrary combination.

Also, the generating circuitry 1403 can generate superimposed image information in which various kinds of information are superimposed on the color image information in addition to a track of a predetermined position (such as joint or predetermined position of predetermined bone) of the object person during walking. For example, as illustrated in FIG. 12K, the generating circuitry 1403 generates superimposed image information in which the track 55 indicating a temporal change in the position of the joint corresponding to the head and a straight line 61 and a straight line 62 which are in contact with ends in the horizontal direction of the track 55 are superimposed on color image information in the object person moves in the depth direction. That is, the generating circuitry 1403 can generate superimposed image information indicating a range of movement of the head in the horizontal direction. Since the image is displayed on the output circuitry 110 by the display controlling circuitry 1404 described later, the operator can observe in what degree the object person moves in the horizontal direction during walking.

Also, the generating circuitry 1403 can generate superimposed image information including information indicating a range of movement of a predetermined part in a different direction similarly to that in the horizontal direction. For example, as illustrated in FIG. 12L, the generating circuitry 1403 generates superimposed image information in which the track 51 indicating a temporal change in the position of the joint corresponding to the head and a straight line 63 and a straight line 64 which are in contact with ends in the vertical direction of the track 51 are superimposed on color image information in which the object person moves in the horizontal direction. That is, the generating circuitry 1403 can generate superimposed image information indicating a range of movement of the head in the vertical direction.

Also, the generating circuitry 1403 can also generate superimposed image information in which information of a track of a predetermined part of the object person and information of a basis are superimposed on each other. For example, as illustrated in FIG. 12M, the generating circuitry 1403 can generate superimposed image information in which the dotted line 58 to be a basis and a track 65 of a right tarsus of the object person are indicated on a floor on a screen. Since the image is displayed on the output circuitry 110 by the display controlling circuitry 1404, the operator can observe in what degree the object person is deviated from the basis during walking.

Also, the generating circuitry 1403 can generate color image information in which information of the object person drawn onto the color image information is changed into an arbitrary character and generate superimposed image information in which information of an angle is superimposed on the generated color image. That is, as illustrated in FIG. 12N, the generating circuitry 1403 can change color image information of the object person in the walking training into color image information in which a bear walks and can generate superimposed image information in which a cross 66 is superimposed, as information of a basis, on the changed color image information. Here, the generating circuitry 1403 can generate superimposed image information in which information of an angle (such as information of straight line illustrated in FIG. 12A or information of segment to connect joints which information is illustrated in FIG. 12B) is further superimposed.

In the above, a case where the generating circuitry 1403 generates superimposed image information as display information has been described. Note that the above-described superimposed image information is just an example. Information included in the superimposed image information can be set arbitrarily. For example, it is also possible to arbitrarily set information included in the superimposed image information based on an instruction to display/not to display superimposed information displayed on the output circuitry 110 according to control by the display controlling circuitry 1404 described later. For example, a cross indicating an angle of a predetermined part and a cross of a basis in the superimposed image information are respectively displayed/undisplayed.

As described above, the generating circuitry 1403 generates track information, superimposed image information, or the like and stores the generated information into the display information storage circuitry 1303. Note that the generating circuitry 1403 can perform a direct output to the display controlling circuitry 1404.

Referring back to FIG. 4, the display controlling circuitry 1404 performs control in such a manner that the track information or the superimposed image information generated by the generating circuitry 1403 is displayed on the output circuitry 110. More specifically, the display controlling circuitry 1404 performs control in such a manner that display information stored into the display information storage circuitry 1303 is read and displayed on the output circuitry 110. For example, the display controlling circuitry 1404 performs control in such a manner that one or a combination of the track information illustrated in FIG. 10A to FIG. 10G and the superimposed image information illustrated in FIG. 12A to FIG. 12N is displayed on the output circuitry 110.

Figure 14:
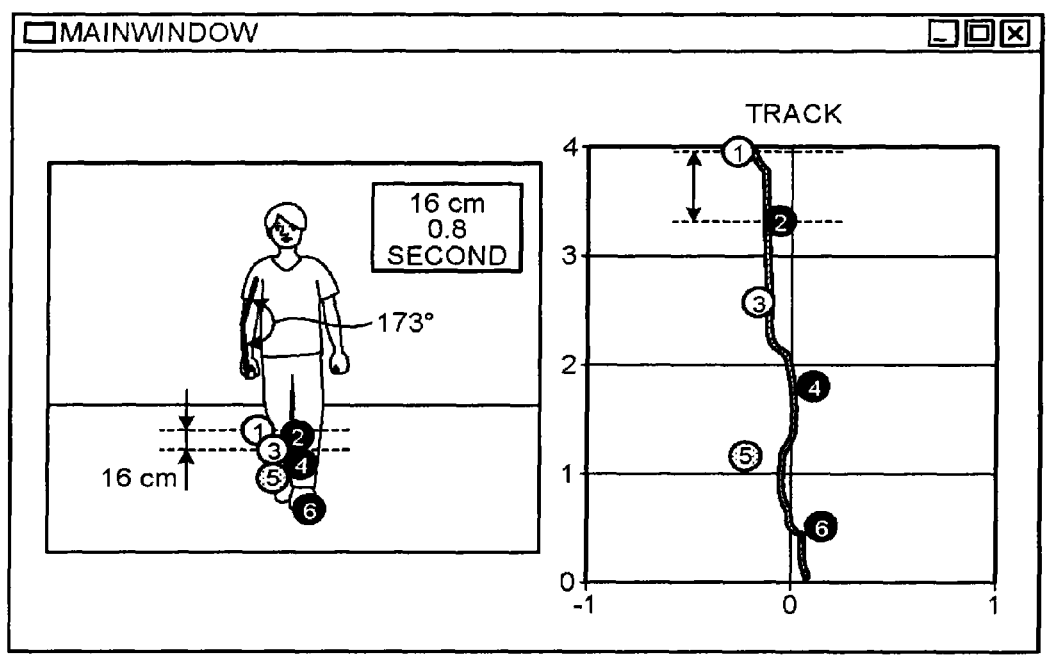
FIG. 14 is a view illustrating an example of a display image displayed by control performed by the display controlling circuitry according to the first embodiment.

In the following, an example of a display image displayed on the display controlling circuitry 1404 will be described with reference to FIG. 13 and FIG. 14. Each of FIG. 13 and FIG. 14 is a view illustrating an example of a display image displayed by control performed by the display controlling circuitry 1404 according to the first embodiment. For example, the display controlling circuitry 1404 displays display information (track information or superimposed image information) stored in the display information storage circuitry 1303 or an analysis result from the analyzing circuitry 1402 on a MainWindow (display screen) of the output circuitry 110.

For example, as illustrated in FIG. 13, the display controlling circuitry 1404 displays superimposed image information on which information of a foot print is superimposed, track information of the foot print, text information and graph information of an analysis result from the analyzing circuitry 1402 on the MainWindow in parallel. Here, these pieces of information are pieces of information in the same walking training of the same object person.

Also, the display controlling circuitry 1404 displays a user interface (UI) to measure a distance, an angle, time, or the like on a screen. For example, as illustrated in FIG. 14, the display controlling circuitry 1404 can display the UI to measure that a stride between a first step and a second step of the object person executing the walking training is "16 cm" and time therebetween is "0.8 second." In such a case, for example, the operator makes the analyzing circuitry 1402 measure a stride between the first step and the second step by clicking each of the "first step" and the "second step" in information of a foot print displayed by being superimposed on the superimposed image information. Alternatively, the operator can perform measurement in a similar manner by clicking the "first step" and the "second step" in information of a foot print included in the track information.

Accordingly, the analyzing circuitry 1402 analyzes a stride and the display controlling circuitry 1404 displays an analysis result on a screen. Here, it is also possible to make the analyzing circuitry 1402 measure time between the first step and the second step. That is, as illustrated in FIG. 14, the time "0.8 second" between the first step and the second step can be measured and displayed.

Also, as illustrated in FIG. 14, it is possible to measure and display an angle "173°" of a right arm of the object person during walking on the UI displayed on the display controlling circuitry 1404. In such a case, for example, the operator designates a right arm of the object person in the superimposed image information by using a mouse or the like. Accordingly, the analyzing circuitry 1402 analyzes an angle of the right arm of the object person at a time point of designation and the display controlling circuitry 1404 displays an analysis result on the screen.

In the above, an example of the display image displayed by the display controlling circuitry 1404 has been described. Note that the above-described example is just an example. The display controlling circuitry 1404 can display various kinds of information in various formats. Thus, next, an example of a display application realized by the motion information processing apparatus 100 according to the present embodiment will be described with reference to FIG. 15 to FIG. 19. FIG. 15 to FIG. 19 are views for describing an example of a display application realized by the motion information processing apparatus 100 according to the first embodiment.

Figure 15:
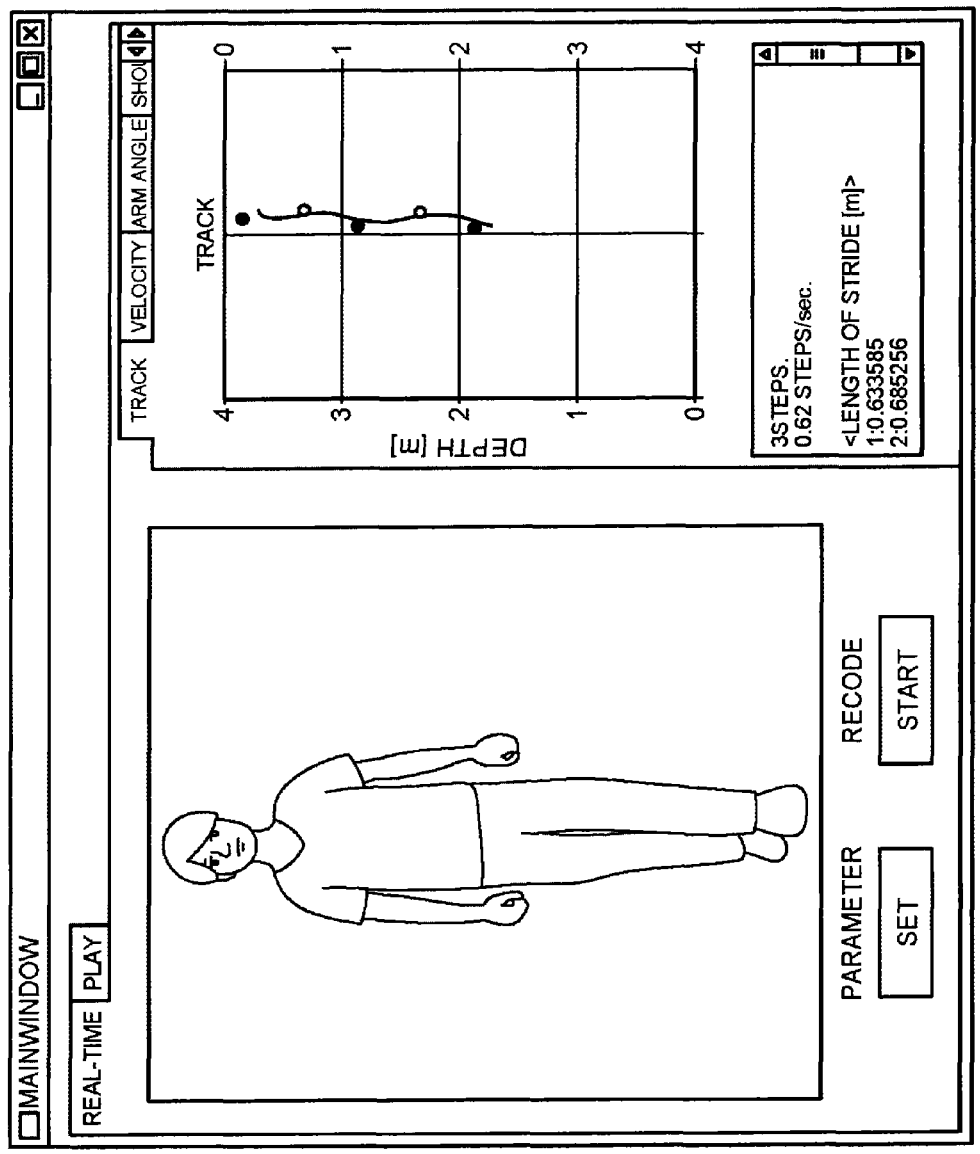
FIG. 15 is a view for describing an example of a display application realized by the motion information processing apparatus according to the first embodiment.

For example, as illustrated in FIG. 15, in the motion information processing apparatus 100 according to the present embodiment, a window including a region to display color image information on a left side and a region to display track information on a right side is displayed on a tab displayed in real time according to control by the display controlling circuitry 1404. In the window, the display controlling circuitry 1404 displays a state of walking of the object person executing a walking motion on the display region of the color image information in real time and displays track information of a foot print and a track of the object person seen from the above in the display region of the track information in real time.

Here, for example, as illustrated in a lower right part of the FIG. 15, the display controlling circuitry 1404 displays a measurement result of the number of steps, average velocity, a stride between steps, or the like. Note that the measurement result is measured by the analyzing circuitry 1402 and output to the display controlling circuitry 1404. Also, as illustrated in an upper right part of FIG. 15, the display controlling circuitry 1404 displays a window including tabs to switch displays of graphs indicated by a "Track," "Velocity," an "Arm Angle," a "Shoulder Angle," and the like. That is, by clicking these tabs, the operator can display each piece of information in a region in which track information is displayed.

Then, as illustrated in a lower part of FIG. 15, in a real-time tab, the display controlling circuitry 1404 displays a window including a "PARAMETER" SET button to set a parameter and a "RECODE" START button to execute a start and an end of recording.

Figure 16:
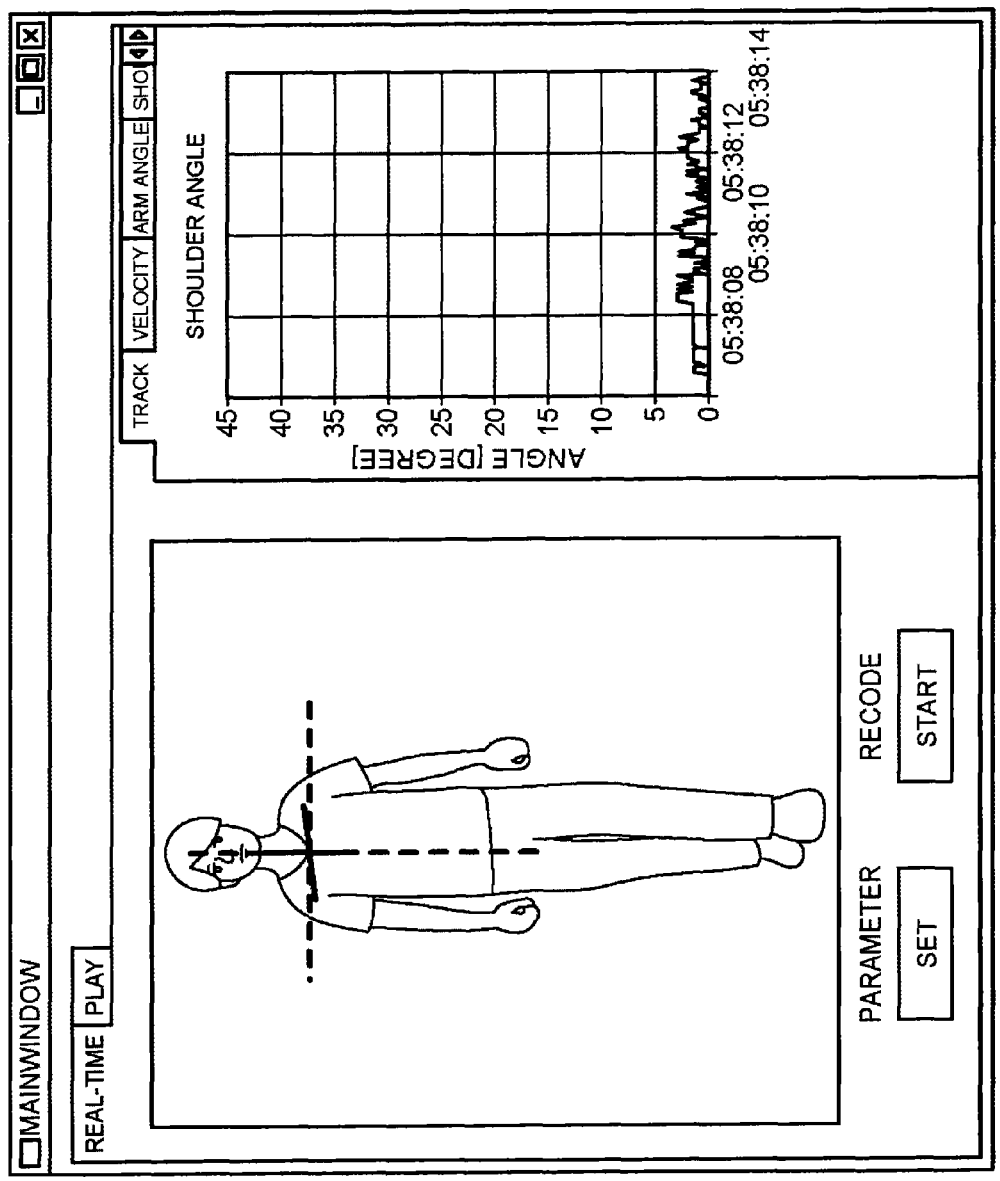
FIG. 16 is a view for describing an example of a display application realized by the motion information processing apparatus according to the first embodiment.

Here, in a real-time tab, it is possible to display superimposed image information in a region to display the color image information. For example, as illustrated in FIG. 16, the display controlling circuitry 1404 displays, on a left side of a window, superimposed image information on which information of an angle indicated by a cross (angle in horizontal and vertical direction) is superimposed. The information of an angle can be arbitrarily displayed by the operator.

For example, the operator can display the superimposed image information in the region to display the color image information and can display a graph indicating an angle of a shoulder at that time in parallel. That is, when the operator clicks the "Shoulder Angle" among upper right tabs in the window, the display controlling circuitry 1404 displays, in the region in which the track information has been displayed, a graph displaying a segment to connect both shoulders and an angle in the horizontal direction in time series, as illustrated in FIG. 16.

Also, in the display application according to the present embodiment, it is possible to display various kinds of information in parallel or to analyze a walking condition and display a determination result. In such a case, for example, as illustrated in FIG. 17, the display controlling circuitry 1404 displays a window, which displays superimposed image information, on a left side of the screen and displays graphs, which respectively indicate the "velocity" and the "angle" in time series, on a right side on the screen.

For example, the display controlling circuitry 1404 displays, on the window on the left side, superimposed image information on which information of an angle is superimposed. Also, the display controlling circuitry 1404 displays velocity (Velocity [m/Sec]: 000.46) in a three-dimensional space of a point indicated on an image (in drawing, point calculated as midpoint of joint position at center of both shoulders and joint position of loin) and an angle (Angle [degree]: 020.98) of a joint indicated on the image (in drawing, joint of right arm).

Here, in the window on the left side to display the superimposed image information, for example, a "Set Threshold" button to set a threshold for determination of a shake of a body or a "Reba Status" button to set ON/OFF of warning. For example, as a "Threshold" in a window illustrated in FIG. 17, a threshold of a shake in a width during walking is set and a value thereof is "0.05."

Figure 17:
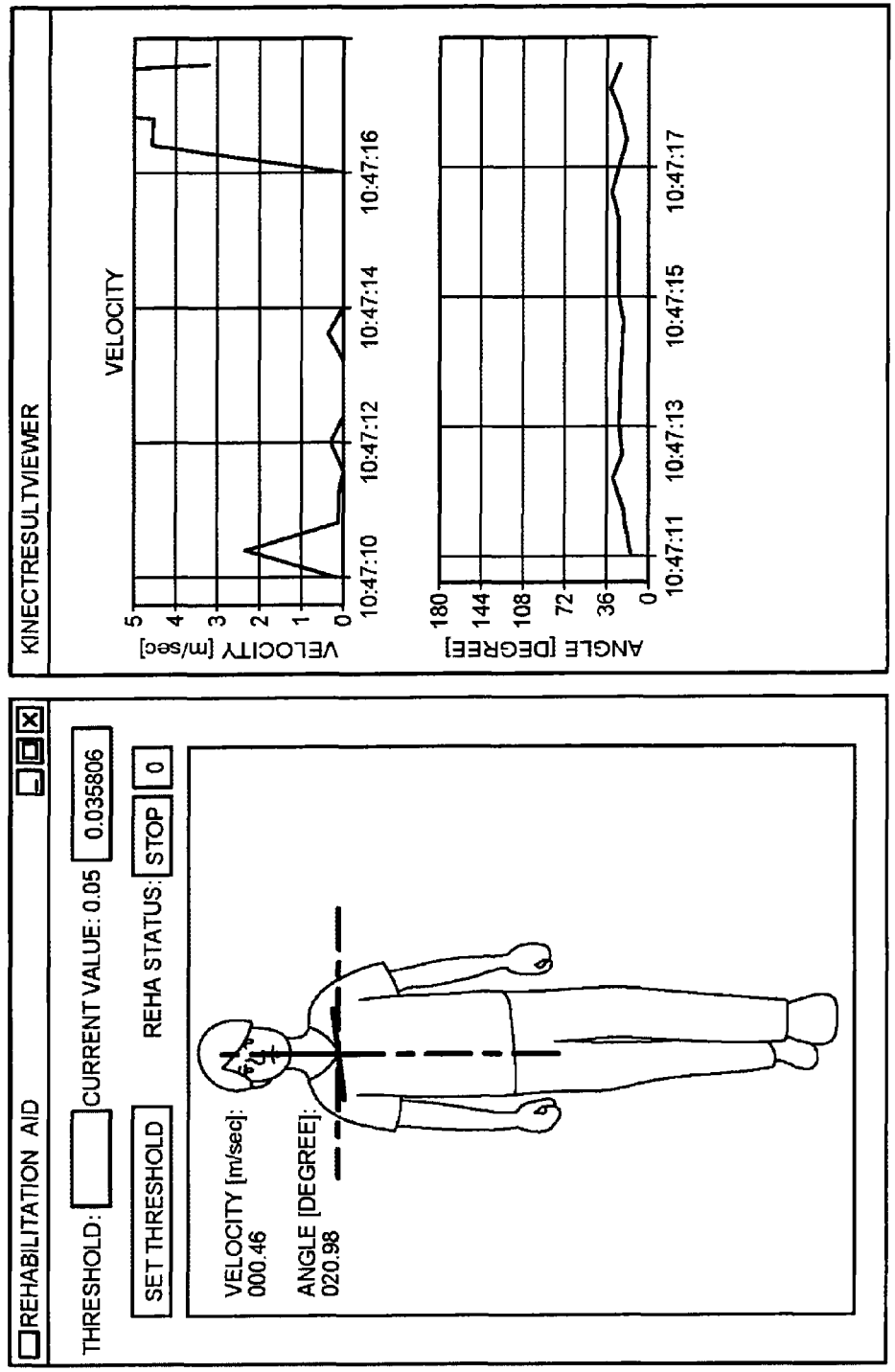
FIG. 17 is a view for describing an example of a display application realized by the motion information processing apparatus according to the first embodiment.

Moreover, as illustrated in FIG. 17, the display controlling circuitry 1404 displays a graph with a horizontal axis indicating time and a vertical axis indicating velocity (Velocity [m/Sec]) and a graph with a horizontal axis indicating time and a vertical axis indicating an angle (Angle [degree]) in parallel. These graphs are pieces of information analyzed by the analyzing circuitry 1402.

Then, for example, when determination of a shake of a body or the like is executed with respect to walking executed by the object person, the analyzing circuitry 1402 determines a shake of a body or the like of the object person in the walking with a set threshold as a determination basis. For example, as illustrated in FIG. 17, when a threshold of a shake in a width during walking is set, the analyzing circuitry 1402 analyzes a motion in a rotation direction centering on a body axis of the object person during walking based on motion information (coordinate of skeleton information) of the object person and determines whether a shake in the rotation direction centering on the body axis exceeds the threshold.

Figure 18:
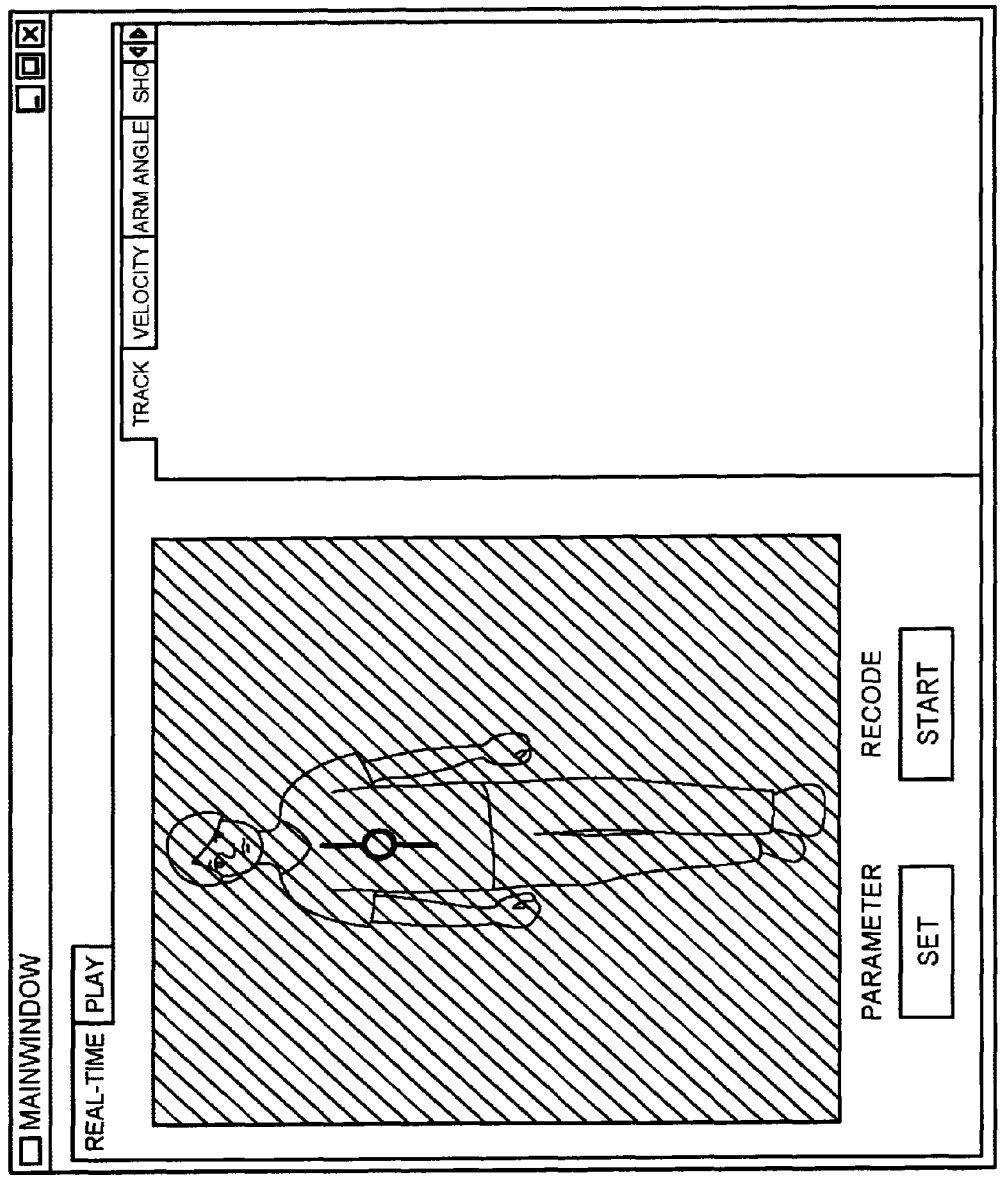
FIG. 18 is a view for describing an example of a display application realized by the motion information processing apparatus according to the first embodiment.

Here, when the shake in the rotation direction centering on the body axis exceeds the threshold, the analyzing circuitry 1402 outputs, to the display controlling circuitry 1404, information indicating that the shake exceeds the threshold. When receiving the information indicating that the shake exceeds the threshold, the display controlling circuitry 1404 displays information indicating that the walking executed by the object person is not stable walking. For example, as illustrated in FIG. 18, the display controlling circuitry 1404 displays a warning by coloring the whole region displaying the superimposed image information in red. Note that when receiving an output indicating that the shake of the body of the object person becomes equal to or lower than the threshold from the analyzing circuitry 1402, the display controlling circuitry 1404 stops displaying the warning and displays only the original superimposed image information.

Note that displaying of a warning by the display controlling circuitry 1404 is not limited to the example illustrated in FIG. 18 and may be executed on the track information such as what is illustrated in FIG. 100. Also, a warning is not only displayed on a screen but also notified, for example, by sound.

Figure 19:
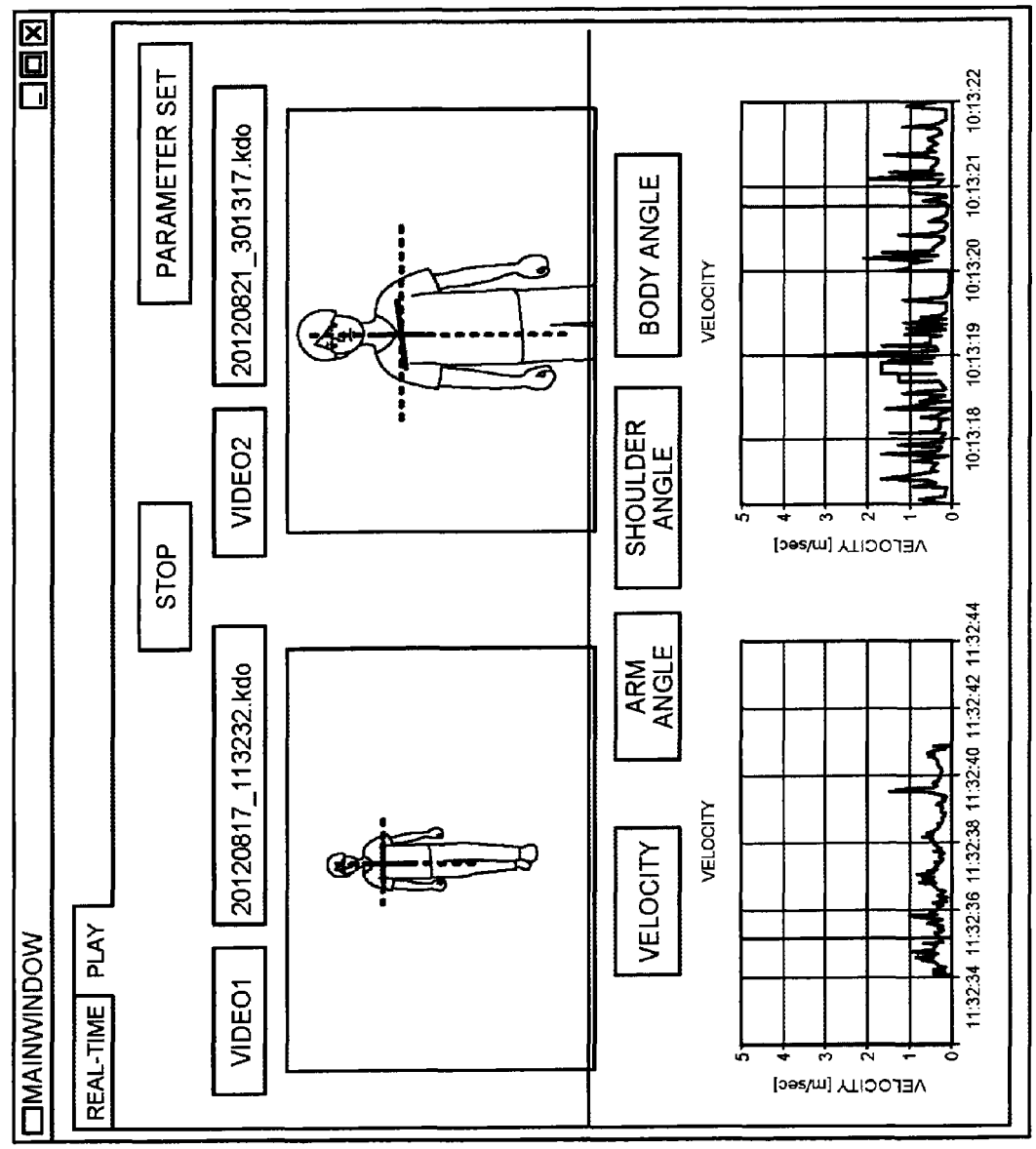
FIG. 19 is a view for describing an example of a display application realized by the motion information processing apparatus according to the first embodiment.

Also, in the display application according to the present embodiment, it is also possible to display a plurality of results in parallel. For example, as illustrated in FIG. 19, the display controlling circuitry 1404 displays pieces of walking data in different periods respectively on right and left parts of the window. For example, the display controlling circuitry 1404 displays superimposed image information and graph information respectively on the right and left regions. Here, the display controlling circuitry 1404 displays, in these regions, information designated by the operator.

That is, the display controlling circuitry 1404 displays image information such as the color image information or the superimposed image information on an upper side of each of the right and the left regions and displays track information or graph information on a lower side of each of the right and the left regions. Here, an object of a comparison display is not limited to data of the same object person. A parallel display with data of a different person can be performed. Thus, for example, the display controlling circuitry 1404 can display pieces of walking data of the same person in different periods in parallel or can display data of a person with a handicap in his/her leg and that of a person with no handicap in his/her leg in parallel.

Note that, for example, as illustrated in FIG. 19, in the window in which pieces of data of a plurality of object people are displayed in parallel, a selection region for selection of the display information stored in the display information storage circuitry 1303, a "Parameter SET" button for selection of a parameter to be displayed, a switch button for switching a graph, or the like is displayed.

Figure 20:
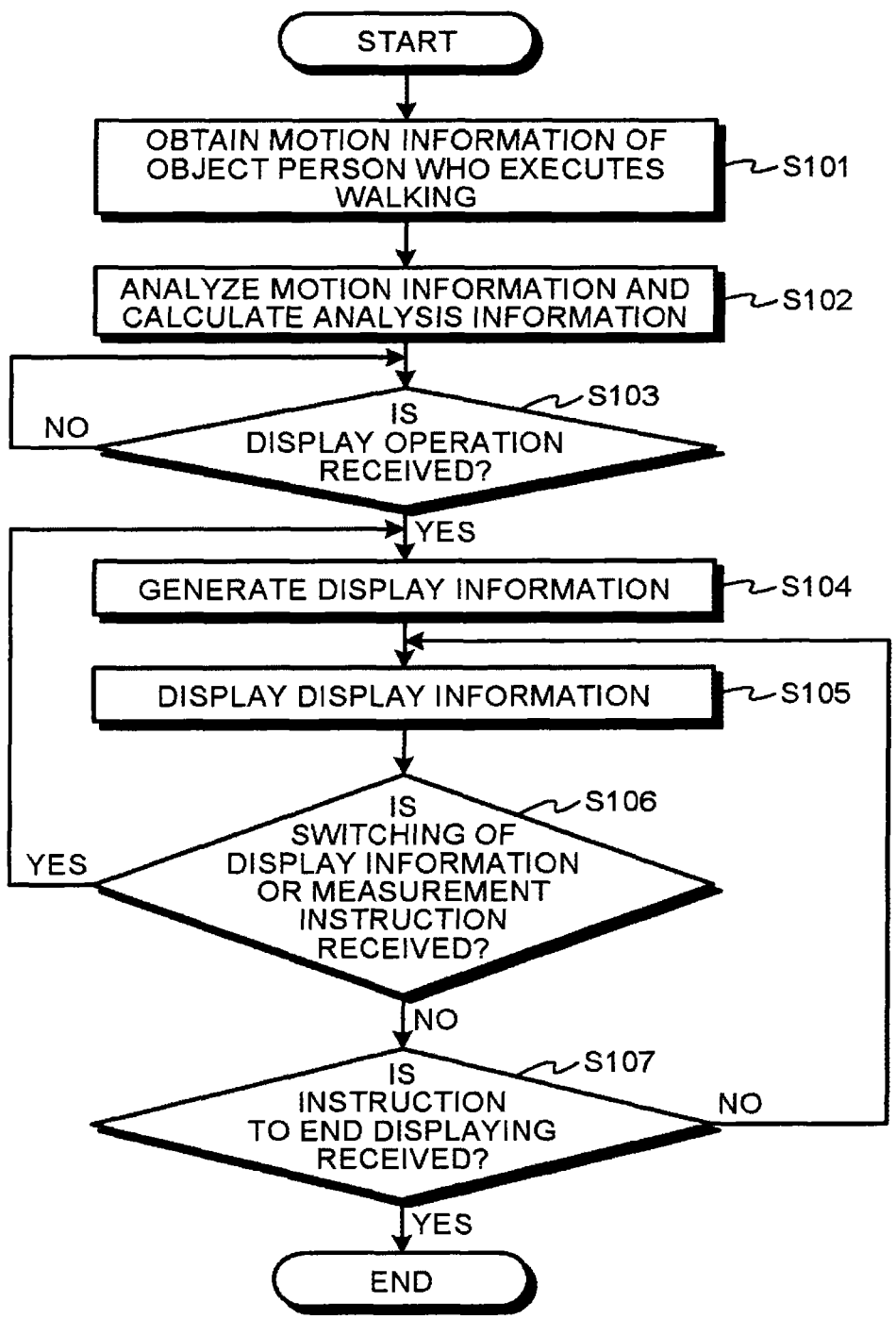
FIG. 20 is a flowchart illustrating a procedure of processing performed by the motion information processing apparatus according to the first embodiment.

Next, with reference to FIG. 20, processing in the motion information processing apparatus 100 according to the first embodiment will be described. FIG. 20 is a flowchart illustrating a procedure of processing performed by the motion information processing apparatus 100 according to the first embodiment. Note that in FIG. 20, a case where processing is performed in real-time is illustrated.

As illustrated in FIG. 20, in the motion information processing apparatus 100 according to the first embodiment, when walking training is started, the obtaining circuitry 1401 obtains motion information of the object person who executes the walking (step S101). Then, the analyzing circuitry 1402 analyzes acquired motion information and calculates analysis information (step S102). Then, the generating circuitry 1403 determines whether a display operation is received (step S103).

Here, when the display operation is received (yes in step S103), the generating circuitry 1403 generates display information (step S104) and the display controlling circuitry 1404 performs control in such a manner that the generated display information is displayed on the output circuitry 110 (step S105). Note that calculation of analysis information is kept performed until the display operation is received (no in step S103).

Then, the generating circuitry 1403 determines whether switching of display information or a measurement instruction is received (step S106). Here, when the switching of display information or the measurement instruction is received (yes in step S106), the generating circuitry 1403 goes back to step S104 and generates display information.

On the other hand, when the switching of display information or the measurement instruction is not received (no in step S106), the motion information processing apparatus 100 determines whether an instruction to end displaying is received (step S107). Here, when the instruction to end displaying is not received (no in step S107), the display controlling circuitry 1404 goes back to step S105 and keeps performing displaying. On the other hand, when the instruction to end displaying is received (yes in step S107), the motion information processing apparatus 100 ends processing.

As described above, according to the first embodiment, the obtaining circuitry 1401 obtains motion information of the object person executing a walking motion. Then, based on the motion information obtained by the obtaining circuitry 1401, the generating circuitry 1403 generates track information indicating a position of a landing point of a foot of the object person. Then, the display controlling circuitry 1404 performs control in such a manner that the track information generated by the generating circuitry 1403 is displayed on the output circuitry 110. Thus, the motion information processing apparatus 100 according to the first embodiment can display a landing point of a foot and a track of a movement in a two-dimensional manner in which it is possible to perform evaluation easily and can provide display information with which it is easy to evaluate a walking condition. As a result, the motion information processing apparatus 100 according to the first embodiment makes it possible to control a difference in evaluation of the walking among doctors, physical therapists, and the like.

Also, according to the first embodiment, the generating circuitry 1403 generates track information which further indicates an angle of a predetermined part of a body of the object person. Thus, by visually expressing a shake of the body or the like of the object person, the motion information processing apparatus 100 according to the first embodiment makes it possible to provide display information with which it is easier to evaluate a walking condition.

Also, according to the first embodiment, an angle of a predetermined part is at least one of a rotation angle indicating forward/backward shaking in a traveling direction of the object person and a rotation angle indicating shaking in an upward/downward direction of the object person. Thus, the motion information processing apparatus 100 according to the first embodiment makes it possible to provide, to an operator, useful information for evaluation of a state of walking.

Also, according to the first embodiment, the generating circuitry 1403 generates, based on the motion information obtained by the obtaining circuitry 1401, track information indicating a track of a movement of the object person in addition to a track of a position of a landing point of a foot. Thus, the motion information processing apparatus 100 according to the first embodiment makes it possible to provide detail information of a state of walking of the object person.

Also, according to the first embodiment, a track of a movement of the object person is a movement track of a feature position of the object person. The feature position is at least one of a position of a predetermined part of the object person, a position calculated by using positions of a plurality of parts, a plurality of center positions of the object person, and a position of a center of gravity of the object person. Thus, the motion information processing apparatus 100 according to the first embodiment makes it possible to observe a movement of the object person in detail.

Also, according to the first embodiment, the obtaining circuitry 1401 obtains motion information of the object person executing a walking motion. Based on the motion information obtained by the obtaining circuitry 1401, the generating circuitry 1403 generates graph information in which a position of a landing point of a right/left foot of the object person is indicated on a graph with one axis as a position of the object person and the other axis as time in a walking motion. The display controlling circuitry 1404 performs control in such a manner that the graph information generated by the generating circuitry 1403 is displayed on the output circuitry 110. Thus, the motion information processing apparatus 100 according to the first embodiment makes it possible to observe a temporal change in a step pattern of a right/left foot of the object person.

Also, according to the first embodiment, the generating circuitry 1403 generates pieces of information included in the track information in a predetermined format in such a manner that identification thereof becomes possible. That is, the generating circuitry 1403 generates information of a foot print in which the number of steps is indicated by a numeric character, performs coloring for distinguishing a right foot and a left foot from each other, or generates information with an arbitrary character. Thus, the motion information processing apparatus 100 according to the first embodiment makes it easy to perform various kinds of identification of when the operator observes display information, whereby effective diagnosis becomes possible.

Also, according to the first embodiment, the input circuitry 120 receives a selection operation to select information to be displayed on the output circuitry 110 from pieces of information included in the track information generated by the generating circuitry 1403. Then, the display controlling circuitry 1404 performs control in such a manner that the information selected by the selection operation received by the input circuitry 120 is displayed on display circuitry. Thus, the motion information processing apparatus 100 according to the first embodiment can effectively display information intended by the operator and can improve a diagnostic efficiency.

Also, according to the first embodiment, the obtaining circuitry 1401 further obtains image information of when the object person executes a walking motion. Then, the display controlling circuitry 1404 performs control in such a manner that the track information generated by the generating circuitry 1403 and the image information obtained by the obtaining circuitry 1401 are displayed on the output circuitry 110. Thus, the motion information processing apparatus 100 according to the first embodiment can show a state of walking of the object person along with the track information and can provide display information with which it is easier to evaluate a walking condition.

Also, according to the first embodiment, the generating circuitry 1403 generates superimposed image information in which information of an angle between a predetermined basis and a predetermined part of the object person is superimposed on the object person drawn onto the image information obtained by the obtaining circuitry 1401. Then, the display controlling circuitry 1404 performs control in such a manner that the track information and the superimposed image information generated by the generating circuitry 1403 are displayed on the output circuitry 110. Thus, the motion information processing apparatus 100 according to the first embodiment can further provide display information indicating a shake of a body or the like on a screen and can make it easier to evaluate a walking condition.

Also, according to the first embodiment, the analyzing circuitry 1402 determines whether a walking motion corresponding to the motion information obtained by the obtaining circuitry 1401 is walking which satisfies a predetermined basis. Then, when the analyzing circuitry 1402 determines that the walking does not satisfy the predetermined basis, the display controlling circuitry 1404 executes a warning display on track information corresponding to the walking motion which is determined to be a walking motion not satisfying the predetermined basis. Thus, the motion information processing apparatus 100 according to the first embodiment executes evaluation of a walking condition automatically and makes it possible to notify a result of the evaluation to an operator and an object person.

Also, according to the first embodiment, the analyzing circuitry 1402 analyzes a walking motion corresponding to the motion information obtained by the obtaining circuitry 1401. Then, the generating circuitry 1403 generates display information including an analysis result analyzed by the analyzing circuitry 1402. Then, the display controlling circuitry 1404 performs control in such a manner that display information which includes the analysis result and which is generated by the generating circuitry 1403 is displayed on output circuitry 110. Thus, for example, the motion information processing apparatus 100 according to the first embodiment makes it possible to provide display information including various kinds of analysis information such as distance information.

Second Embodiment

In the above, the first embodiment has been described. However, there are various different embodiments other than the above-described first embodiment.

In the above-described first embodiment, an example of track information in which a foot print of an object person moves in a vertical direction has been described. However, an embodiment is not limited to this. For example, in track information, a foot print of the object person may move in a rotation direction centering on a body axis.

In the above-described first embodiment, a case where image information such as superimposed image information, track information, and the like are displayed in parallel in comparison between different periods of the same person or comparison with a different person has been described. However, an embodiment is not limited to this. For example, there may be a case where pieces of information are superimposed on each other. For example, there may be a case where track information indicating a track of a foot print is overlapped and displayed. In such a case, for example, display controlling circuitry 1404 displays pieces of track information in different layers. Here, transmittance of information to be displayed may be changed.

In the above-described first embodiment, a case where a prescribed joint (such as tarsus, ankle, or knee) is used as a coordinate used for calculation of a landing point of a foot has been described. However, an embodiment is not limited to this. For example, there may be a case where a landing point of a foot is calculated by using a coordinate of a position set between predetermined joints.

In the above-described first embodiment, a case where the motion information processing apparatus 100 includes the analyzing circuitry 1402 has been described. However, an embodiment if not limited this. For example, there may be a case where the generating circuitry 1403 generates display information such as track information or superimposed image information by using an analysis result analyzed in the outside.

In the above-described first embodiment, a case where a landing point of a foot is calculated by analyzing coordinate information of a joint of an object person has been described. However, an embodiment is not limited to this. For example, there may be a case where a landing point of a foot is calculated by using information collected by motion capture a sensor of which is attached to a body of an object person or there may be a case where a landing point of a foot is calculated by a sheet using a pressure sensor.

In the above-described first embodiment, a case where a warning is displayed by coloring a whole region, in which superimposed image information is displayed, in red has been described (see FIG. 18). However, as described above, an embodiment is not limited to this. A warning can be displayed by various methods. FIG. 21 is a view illustrating an example of a warning display by display controlling circuitry 1404 according to the second embodiment. In FIG. 21, a dotted line 58 to be a basis is indicated on a ground on a screen and superimposed image information indicating a track 65 of a right tarsus of an object person is further indicated.

For example, as illustrated in FIG. 21, the display controlling circuitry 1404 displays a mark of a warning on the screen when the right tarsus moves away from the dotted line 58, which is the basis, for more than a predetermined threshold in walking of the object person. Note that the analyzing circuitry 1402 analyzes whether the predetermined threshold is exceeded. Accordingly, an operator can easily determine whether walking by the object person is stable walking. Here, a basis for determination whether walking by the object person is stable walking can be set arbitrarily. FIG. 22 is a view for describing an example of a determination basis used by analyzing circuitry 1402 according to the second embodiment.

For example, as illustrated in FIG. 22, the analyzing circuitry 1402 performs determination based on a determination basis in which a walking state and a warning are associated to each other. Here, the "walking state" is a stare during walking which state is for determination of unstable walking by the object person. Also, the "warning" indicates what kind of unstable state the object person is in when the object person becomes a corresponding walking state. For example, as illustrated in FIG. 22, when a "walking state" of the object person becomes a state of an "inclination of a straight line which connects a head and a loin>20°," the analyzing circuitry 1402 determines that a "body is inclined" and gives a notification to the display controlling circuitry 1404 to display a warning.

Similarly, the analyzing circuitry 1402 determines whether walking by the object person is stable by using a determination basis illustrated in FIG. 22. Here, the determination basis illustrated in FIG. 22 is just an example. Various different determination bases are set arbitrarily by the operator. Such a determination basis is stored, for example, in storage circuitry 130 and is arbitrarily referred to by the analyzing circuitry 1402.

As described above, the motion information processing apparatus 100 according to each of the first and second embodiments outputs display information analyzed by using the information collected by the motion information collecting circuitry 10. Here, the motion information processing apparatus 100 can also output, on output circuitry 110, display information analyzed by analyzing circuitry described in each of third and fourth embodiments and fifth to seventh embodiments described later. That is, the motion information processing apparatus 100 can output, from the output circuitry 110, display information analyzed by an analysis method described in each of the third and fourth embodiments described later and display information analyzed by an analysis method described in each of the fifth to seventh embodiments described later.

Third Embodiment

Figure 23:
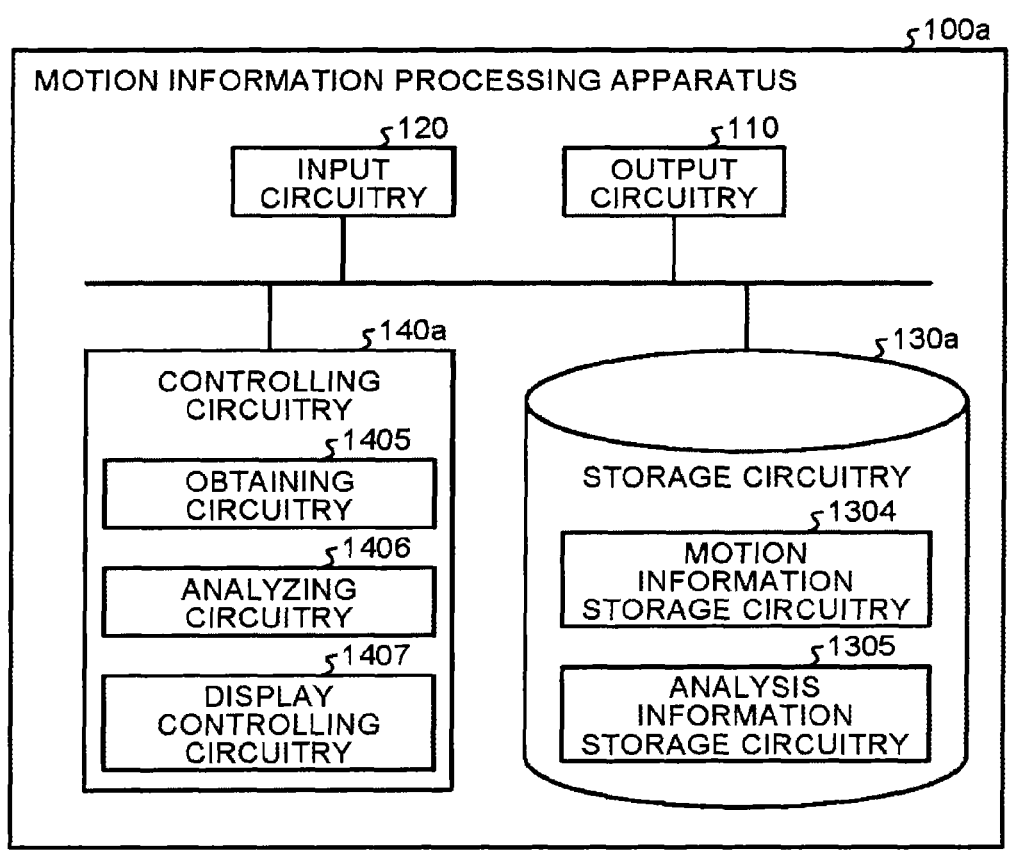
FIG. 23 is a view illustrating an example of a detail configuration of a motion information processing apparatus according to a third embodiment.

Next, a configuration of a motion information processing apparatus 100a according to the third embodiment will be described. Based on the configuration described in the first embodiment (configuration illustrated in FIG. 1), the motion information processing apparatus 100a according to the third embodiment makes it possible to evaluate a walking condition easily with a configuration described in detail in the following. FIG. 23 is a view illustrating an example of a detail configuration of the motion information processing apparatus 100a according to the third embodiment. Note that in the motion information processing apparatus 100a illustrated in FIG. 23, storage circuitry 130a and controlling circuitry 140a described later are different from those of the motion information processing apparatus 100 illustrated in FIG. 4. First, a detail of storage circuitry 130a in the motion information processing apparatus 100a will be described. As illustrated in FIG. 23, in the motion information processing apparatus 100a, for example, the storage circuitry 130a includes motion information storage circuitry 1304 and analysis information storage circuitry 1305.

The motion information storage circuitry 1304 stores various kinds of information collected by motion information collecting circuitry 10. More specifically, the motion information storage circuitry 1304 stores motion information generated by motion information generating circuitry 14. More specifically, the motion information storage circuitry 1304 stores skeleton information in each frame which information is generated by the motion information generating circuitry 14. Here, the motion information storage circuitry 1304 can further store color image information, distance image information, and a sound recognition result output from the motion information generating circuitry 14 while associating these into each frame.

For example, the motion information storage circuitry 1304 according to the third embodiment stores the motion information illustrated in FIG. 5 described above. That is, as illustrated in FIG. 5, the motion information storage circuitry 1304 stores motion information in which a name number, a performance date, and motion information are associated to each other with respect to each name. Here, the "name number" is an identifier to uniquely identify an object person and is assigned to each name. The "performance date" indicates a date and time on which the object person performs walking training. The "motion information" indicates information collected by the motion information collecting circuitry 10.

For example, as illustrated in FIG. 5, the motion information storage circuitry 1304 stores "a name: A, a name number: 1, a performance date: 20120801_1, and motion information: color image information, distance image information, a sound recognition result, skeleton information, . . . " The above-described information indicates that motion information including the "color image information," the "distance image information," the "sound recognition result," and the "skeleton information" is stored as motion information of "first" walking performed on "August 1st" in "2012" by a person with the "name: A" the "name number" of which is "1."

Here, in the motion information illustrated in FIG. 5, "color image information," "distance image information," a "sound recognition result," and "skeleton information" in all frames photographed during execution of a walking motion are associated to time and stored in time series.

Also, as illustrated in FIG. 5, the motion information storage circuitry 1304 stores "a name: A, a name number: 1, a performance date: 20120801_2, and motion information: color image information, distance image information, a sound recognition result, skeleton information, . . . " That is, the motion information storage circuitry 1304 similarly stores motion information of "second" walking performed on "August 1st" in "2012" by the person with the "name: A."

Also, as illustrated in FIG. 5, the motion information storage circuitry 1304 also stores, with respect to a person with "a name: B and a name number: 2," motion information including "color image information," "distance image information," a "sound recognition result," and "skeleton information." In such a manner, the motion information storage circuitry 1304 stores motion information of walking, which information is collected for each object person, while associating the information to each object person. Note that the motion information illustrated in FIG. 5 is just an example.

That is, the motion information storage circuitry 1304 can store information other than the "color image information," the "distance image information," the "sound recognition result," and the "skeleton information" illustrated in FIG. 5 while further associating the information. Also, for example, when the motion information collecting circuitry 10 does not include sound recognizing circuitry 13, storing is performed without the sound recognition result.

Also, each of the "color image information" and the "distance image information" included in the motion information includes image data in a BIT MAP, a JPEG, or a different binary format or a link or the like to the image data. Also, in addition to the above-described recognition information, the "sound recognition result" included in the motion information may be sound data itself or a link to recognition information or sound data.

The analysis information storage circuitry 1305 stores an analysis result by the controlling circuitry 140a described later. More specifically, the analysis information storage circuitry 1305 stores an analysis result which is analyzed by the controlling circuitry 140a described later by using the motion information stored in the motion information storage circuitry 1304. For example, the analysis information storage circuitry 1305 according to the third embodiment stores the analysis information illustrated in FIG. 6 described above. Here, the "name number" is an identifier to uniquely identify an object person and is assigned to each name. The "performance date" indicates a date and time on which the object person performs walking training. The "analysis information" indicates information of an analysis result analyzed by the controlling circuitry 140a described later.

For example, as illustrated in FIG. 6, the analysis information storage circuitry 1305 stores "a name: A, a name number: 1, a performance date: 20120801_1, and analysis information: a landing point of a foot, an angle, velocity, acceleration, the number of steps, a stride, an overlapped walking distance, a step interval, a walking rate, . . . " The above-described information indicates that analysis information including a "landing point of a foot," an "angle," "velocity," "acceleration," the "number of steps," a "stride," an "overlapped walking distance," a "step interval," and a "walking rate" is stored as information of an analysis result analyzed by using motion information of "first" walking performed on "August 1st" in "2012" by a person with the "name: A" the "name number" of which is "1."

Here, the "landing point of a foot" is information indicating a position, where a foot of an object person touches a ground, and is stored, for example, as coordinate information. Also, the "angle" is information indicating an angle of a body of an object person during walking and information of an angle between a predetermined basis and a part of a body is stored. For example, the analysis information storage circuitry 1305 stores, as the "angle" of the analysis information, information such as an angle of a body in a vertical direction. Note that with respect to the information of the "angle" of the analysis information, a basis and a part of a body are arbitrarily set by an operator. Also, the "velocity" is information indicating velocity of an object person during walking. For example, information of velocity of a predetermined part (such as center of body) is stored. Also, the "acceleration" is information indicating acceleration of an object person during walking. For example, information of acceleration of a predetermined part is stored. Also, the "number of steps" is information indicating the number of steps the object person walks in walking training. Also, the "stride" is information indicating a distance in a traveling direction from a landing point of a right foot (left foot) to a landing point of a left foot (right foot) in walking by an object person. Also, the "overlapped walking distance" is information indicating a distance from landing of one foot to next landing of the foot. Also, the "step interval" is information indicating a distance in a direction orthogonal to a traveling direction from a landing point of a right foot (left foot) to a landing point of a left foot (right foot) in walking by an object person. Also, the "walking rate" is information indicating the number of steps in a unit time.

Similarly, as illustrated in FIG. 6, the analysis information storage circuitry 1305 stores, with respect to a person with "a name: B and a name number: 2," analysis information including a "landing point of a foot," an "angle," "velocity," "acceleration," the "number of steps," a "stride," an "overlapped walking distance," a "step interval," and a "walking rate." In such a manner, the analysis information storage circuitry 1305 stores analysis information, which is motion information of walking collected for each object person and analyzed by the controlling circuitry 140a described later, while associating the analysis information to each object person. Note that the analysis information illustrated in FIG. 6 is just an example. For example, walking time, a period of time in which a foot is on the ground, or the like may be also included. Various kinds of information included in analysis information are arbitrarily changed according to setting performed by an operator with respect to the controlling circuitry 140a described later. For example, there is a case where an item among the pieces of information illustrated in FIG. 6 is not calculated.

Next, a detail of the controlling circuitry 140a of the motion information processing apparatus 100a will be described. As illustrated in FIG. 23, in the motion information processing apparatus 100a, for example, the controlling circuitry 140a includes obtaining circuitry 1405, analyzing circuitry 1406, and display controlling circuitry 1407.

The obtaining circuitry 1405 obtains motion information of an object person who executes walking training. More specifically, the obtaining circuitry 1405 obtains the motion information collected by the motion information collecting circuitry 10 and stored in the motion information storage circuitry 1304. For example, according to analysis contents by the analyzing circuitry 1406 described later, the obtaining circuitry 1405 obtains at least one of color image information, distance image information, a sound recognition result, and skeleton information stored in each frame by the motion information storage circuitry 1304.

For example, when a landing point of a foot, an angle, velocity, and the like are analyzed by the analyzing circuitry 1406 described later, the obtaining circuitry 1405 obtains all pieces of color image information, distance image information, and skeleton information related to a series of walking motions in walking training of an object person.

The analyzing circuitry 1406 executes various kinds of analysis by using the motion information of the object person who executes a walking motion which information is obtained by the obtaining circuitry 1405. More specifically, the analyzing circuitry 1406 analyzes a walking state including a position of a landing point of a foot of the object person based on a temporal change in a position of a predetermined part of the object person in the motion information obtained by the obtaining circuitry 1405. Also, by using motion information such as color image information, distance image information, a sound recognition result, and skeleton information obtained by the obtaining circuitry 1405, the analyzing circuitry 1406 calculates analysis information of a walking state such as an angle, velocity, acceleration, or a distance of the object person and stores the calculated analysis result into the analysis information storage circuitry 1305.

Figure 24:
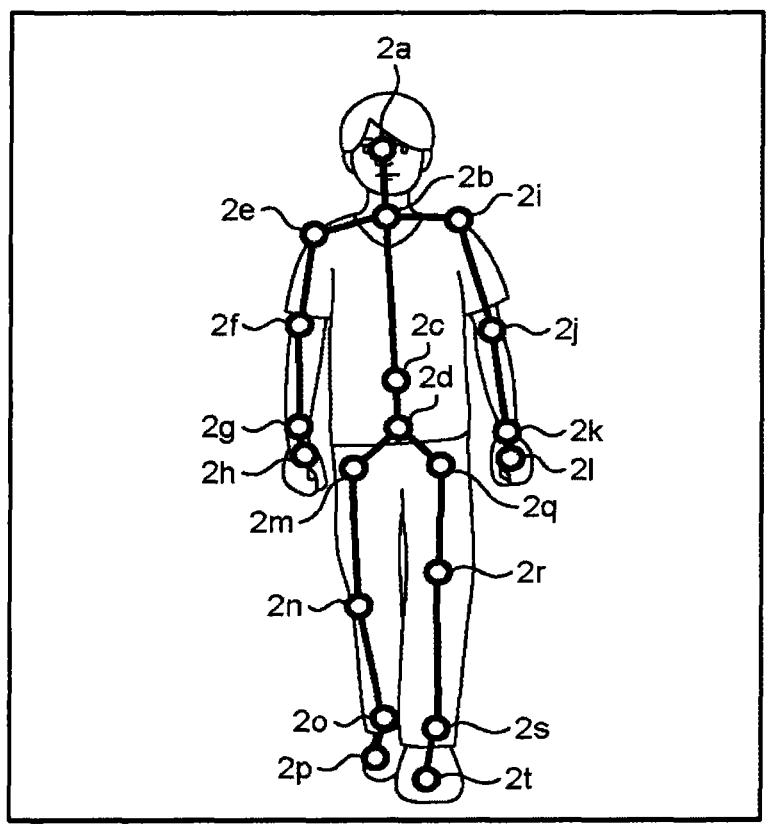
FIG. 24 is a view for describing an example of an analysis target in an analysis of a landing point of a foot performed by analyzing circuitry according to the third embodiment.

Here, first, a case of analyzing a landing point of a foot will be described. FIG. 24 is a view for describing an example of an analysis target in an analysis of a landing point of a foot performed by the analyzing circuitry 1406 according to the third embodiment. Note that in FIG. 24, skeleton information in one frame which information is collected by the motion information collecting circuitry 10 is illustrated schematically. For example as illustrated in FIG. 24, the analyzing circuitry 1406 calculates a landing point of a foot of an object person by using skeleton information in the motion information collected by the motion information collecting circuitry 10. That is, when a temporal and three-dimensional change in a position of a predetermined part of the object person in motion information (coordinate information) of the object person executing a walking motion is smaller than a predetermined threshold such as a case illustrated in FIG. 24, the analyzing circuitry 1406 determines that a foot of the object person is on a ground and sets, as a landing point, a position of the foot of the object person at a time point of the determination.

Here, in a case of calculating a landing point of a foot of the object person, for example, an operator such as a doctor or a physical therapist first inputs an instruction request of analysis through input circuitry 120. Here, by inputting a name, a name number, a performance date, and the like of an object person, the operator makes the obtaining circuitry 1405 obtain intended motion information. The obtaining circuitry 1405 obtains, from the motion information storage circuitry 1304, motion information corresponding to the object person received through the input circuitry 120. Note that in a case where analysis is executed along with walking training in real time, it is possible to perform setting in such a manner that motion information is obtained automatically without reception of an operation from the operator.

For example, as illustrated in FIG. 24, according to the above-described designation by the operator or designation by automatic acquisition, the obtaining circuitry 1405 obtains skeleton information of the designated object person in each frame from the motion information storage circuitry 1304. By using the skeleton information obtained by the obtaining circuitry 1405, the analyzing circuitry 1406 calculates a landing point where a foot of the object person touches a ground. For example, as illustrated in FIG. 24, the analyzing circuitry 1406 calculates a landing point by using coordinate information of a joint, which corresponds to each part of a foot, in the skeleton information of the object person executing the walking training.

For example, when a change amount of a predetermined part (such as joint corresponding to each part of foot) of the object person in a unit time is smaller than a predetermined threshold, the analyzing circuitry 1406 determines that a foot of the object person is on the ground. Here, the analyzing circuitry 1406 analyzes a change amount of a position of a predetermined part in a unit time in a traveling direction of walking of the object person, a body axis direction, or a direction orthogonal to the traveling direction. That is, for example, when a traveling direction of the object person is a depth direction in a coordinate space of motion information (skeleton information), the analyzing circuitry 1406 calculates a landing point of a foot by analyzing a change in a value of a z coordinate, a y coordinate, or an x coordinate in skeleton information of a predetermined part of the object person.

Here, the analyzing circuitry 1406 can analyze a traveling direction of walking by the object person. For example, based on a movement of a joint "2c" corresponding to a loin in xz coordinates (direction horizontal to ground), the analyzing circuitry 1406 analyzes a direction of walking by the object person. That is, the analyzing circuitry 1406 traces a movement of the joint "2c" in the xz coordinates and calculates an approximate curve with respect to a traced line. The analyzing circuitry 1406 analyzes a direction of the calculated approximate curve as a walking direction of the object person. Note that the above-described example is just an example and a joint to be used is not limited to the joint "2c" corresponding to the loin. Also, the analyzing circuitry 1406 can calculate a walking direction of the object person from a position of a landing point of a foot described later. That is, the analyzing circuitry 1406 calculates a walking direction by extracting a position of a landing point of a foot in time series.

Figure 25A:
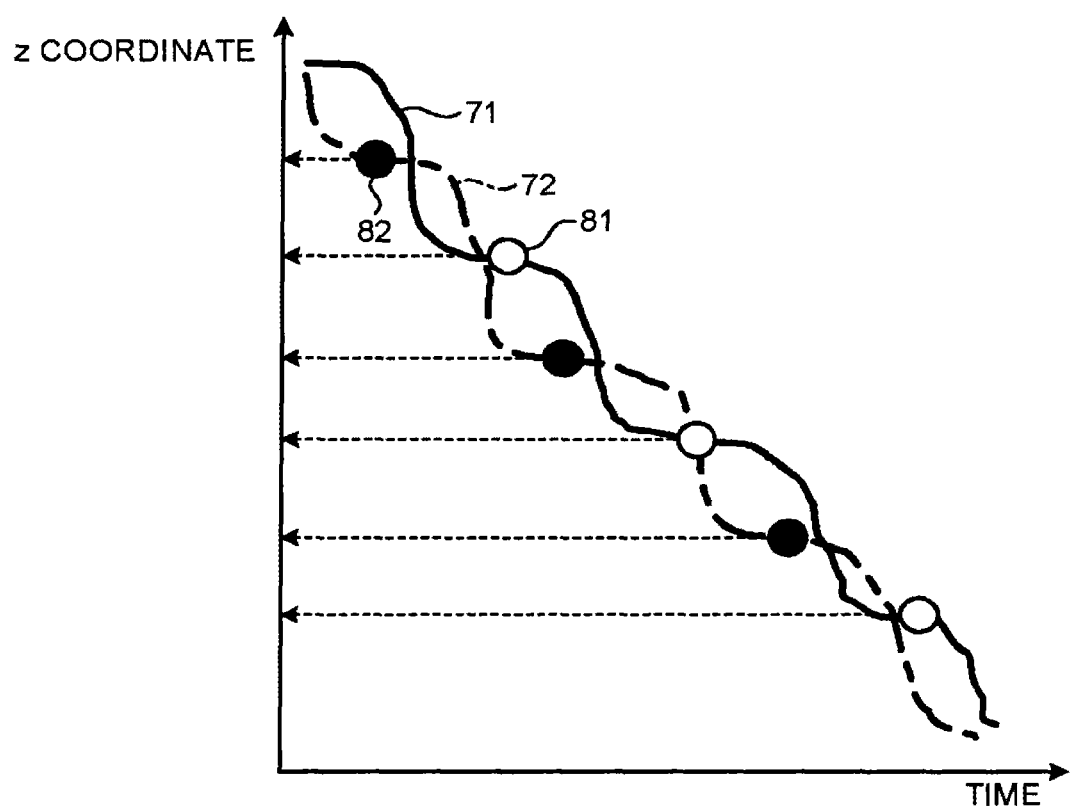
FIG. 25A is a graph for describing an example of an analysis of a landing point of a foot performed by the analyzing circuitry according to the third embodiment by using a z coordinate.

In the following, with reference to FIG. 25A to FIG. 25F, an example of an analysis of a landing point of a foot using each coordinate will be described. Note that in FIG. 25A to FIG. 25F, a description will be made with a case where the object person walks in a depth direction (z-axis direction) as an example. FIG. 25A is a graph for describing an example of an analysis of a landing point of a foot performed by the analyzing circuitry 1406 according to the third embodiment by using a z coordinate. For example, the analyzing circuitry 1406 acquires, from all frames, a value of a z coordinate of a joint "2p" corresponding to a right tarsus and a value of a z coordinate of a joint "2t" corresponding to a left tarsus and generates a graph with a vertical axis as the z coordinate and a horizontal axis as time, as illustrated in FIG. 25A.

That is, as illustrated in FIG. 25A, the analyzing circuitry 1406 calculates a curved line 71 indicating a temporal change in the z coordinate of the left tarsus and a curved line 72 indicating a temporal change in the z coordinate of the right tarsus. Then, for example, the analyzing circuitry 1406 determines that a time point at which a change in a value of the z coordinate in a unit time in each curved line is equal to or smaller than a predetermined threshold is a time point at which a foot touches a ground.

For example, as illustrated in FIG. 25A, the analyzing circuitry 1406 determines that a time point 81 at which a change in a coordinate in a unit time is equal to or smaller than a predetermined threshold in a curved line 71 indicating a temporal change in the z coordinate of the left tarsus is a time point at which a left foot touches a ground. Similarly, as illustrated in FIG. 25A, the analyzing circuitry 1406 determines that a time point 82 at which a change in a coordinate in a unit time in the curved line 72 indicating a temporal change in the z coordinate of the right tarsus becomes equal to or smaller than a predetermined threshold is a time point at which a right foot touches the ground. The analyzing circuitry 1406 stores, into the analysis information storage circuitry 1305, skeleton information in a frame corresponding to a time point at which it is determined that a foot touches the ground.

Note that the above-described example is just an example and a coordinate to be used is not limited to the above-described example. That is, for example, there may be a case where a z coordinate of an ankle or a z coordinate of a knee is used in addition to the z coordinate of the tarsus. Also, for example, there may be a case where comprehensive determination is made by using not only a change in a z coordinate of a single joint but also a change in a z coordinate of each of two joints such as a tarsus and a knee.

Also, in the above-described example, a case of determining that a time point at which a change in a z coordinate of a foot in a unit time is equal to or smaller than a predetermined threshold is a time point at which the foot touches a ground has been described. However, an embodiment is not limited to this. For example, there may be a case of determining that a time point at which a change in a z coordinate of a foot in a unit time is equal to or larger than a predetermined threshold is a time point at which an opposite foot of the foot touches the ground. For example, as illustrated in FIG. 25A, the analyzing circuitry 1406 determines that a time point at which a change in a unit time in the curved line 71 indicating a temporal change in the z coordinate of the left tarsus is equal to or larger than a predetermined threshold is a time point at which the right foot touches the ground. Similarly, as illustrated in FIG. 25A, the analyzing circuitry 1406 determines that a time point at which a change in a unit time in the curved line 72 indicating a temporal change in the z coordinate of the right tarsus is equal to or larger than a predetermined threshold is a time point at which the left foot touches the ground.

Figure 25B:
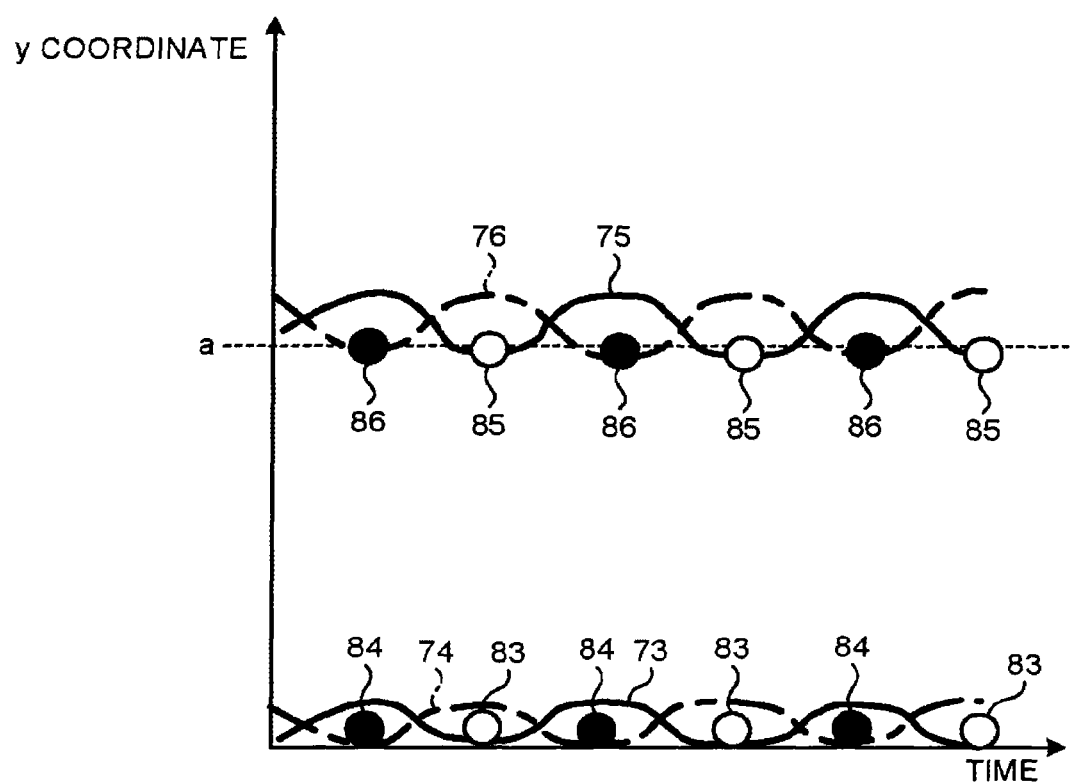
FIG. 25B is a graph for describing an example of an analysis of a landing point of a foot performed by the analyzing circuitry according to the third embodiment by using a y coordinate.

Next, a case of determining a landing point of a foot by using a y coordinate will be described. FIG. 25B is a graph for describing an example of an analysis of a landing point of a foot performed by the analyzing circuitry 1406 according to the third embodiment by using a y coordinate. For example, the analyzing circuitry 1406 acquires, from all frames, a value of a y coordinate of the joint "$2p$" corresponding to the left tarsus and a value of a y coordinate of the joint "$2t$" corresponding to the right tarsus and generates a graph with a vertical axis as the y coordinate and a horizontal axis as time, as illustrated in FIG. 25B.

That is, as illustrated in a lower curve and point in FIG. 25B, the analyzing circuitry 1406 calculates a curved line 73 indicating a temporal change in the y coordinate of the left tarsus and a curved line 74 indicating a temporal change in the y coordinate of the right tarsus. Then, for example, the analyzing circuitry 1406 determines that a time point at which a value of the y coordinate in each curved line becomes a predetermined value (such as "y=0") is a time point at which a foot touches the ground.

For example, as illustrated in the lower point in FIG. 25B, the analyzing circuitry 1406 determines that a time point 83 at which a value of a y coordinate becomes a predetermined value (such as "y=0") in the curved line 73 indicating a temporal change in the y coordinate of the left tarsus is a time point at which the left foot touches the ground. Similarly, as illustrated in the lower point in FIG. 25B, the analyzing circuitry 1406 determines that a time point 84 at which a value of a y coordinate becomes the predetermined value (such as "y=0") in the curved line 74 indicating a temporal change in the y coordinate of the right tarsus is a time point at which the right foot touches the ground. The analyzing circuitry 1406 stores, into the analysis information storage circuitry 1305, skeleton information in a frame corresponding to a time point at which it is determined that a foot touches the ground.

Also, for example, the analyzing circuitry 1406 acquires, from all frames, a value of a y coordinate of a joint "$2n$" corresponding to a right knee and a value of a y coordinate of a joint "$2r$" corresponding to a left knee and generates a graph with a vertical axis as a z coordinate and a horizontal axis as time, as illustrated in FIG. 25B.

That is, as illustrated in an upper curve and point in FIG. 25B, the analyzing circuitry 1406 calculates a curved line 75 indicating a temporal change in the y coordinate of the left knee and a curved line 76 indicating a temporal change in the y coordinate of the right knee. Then, for example, the analyzing circuitry 1406 determines that a time point at which a value of the y coordinate in each curved line becomes equal to or smaller than a predetermined threshold (such as "y=a") is a time point at which a foot touches the ground.

For example, as illustrated in the upper point in FIG. 25B, the analyzing circuitry 1406 analyzes that a time point 85 at which a value of a y coordinate becomes equal to or smaller than the predetermined threshold (such as "y=a") in the curved line 75 indicating a temporal change in the y coordinate of the left knee is a time point at which the left foot touches the ground. Similarly, as illustrated in the upper point in FIG. 25B, the analyzing circuitry 1406 determines that a time point 86 at which a value of a y coordinate becomes equal to or smaller than the predetermined value (such as "y=a") in the curved line 76 indicating a temporal change in the y coordinate of the right knee is a time point at which the right foot touches the ground. The analyzing circuitry 1406 stores, into the analysis information storage circuitry 1305, skeleton information in a frame corresponding to a time point at which it is determined that a foot touches the ground.

Note that the above-described example is just an example and a coordinate to be used is not limited to the above-described example. That is, for example, there may be a case where not only a y coordinate of a tarsus or a knee but also a y coordinate of an ankle is used. Also, for example, there may be a case where comprehensive determination is made by using not only a change in a y coordinate of a single joint but also a change in a y coordinate of each of two joints such as a tarsus and a knee.

Also, in the above-described example, a case of determining that a time point at which a change in a y coordinate of a foot in a unit time is equal to or smaller than a predetermined threshold is a time point at which the foot touches a ground has been described. However, an embodiment is not limited to this. For example, there may be a case of determining that a time point at which a change in a y coordinate of a foot in a unit time is equal to or larger than a predetermined threshold is a time point at which an opposite foot of the foot touches the ground. That is, the analyzing circuitry 1406 determines whether a foot is in the air and determines that the other foot is on the ground when one foot is in the air. For example, when a description is made with FIG. 25B as an example, the analyzing circuitry 1406 determines that a time point at which a value of a y coordinate becomes a predetermined value (such as "y>b") in the curved line 73 indicating a temporal change in the y coordinate of the left tarsus is a time point at which the right foot touches the ground. Similarly, the analyzing circuitry 1406 determines that a time point at which a value of a y coordinate becomes the predetermined value (such as "y>b") in the curved line 74 indicating a temporal change in the y coordinate of the right tarsus is a time point at which the left foot touches the ground.

Figure 25C:
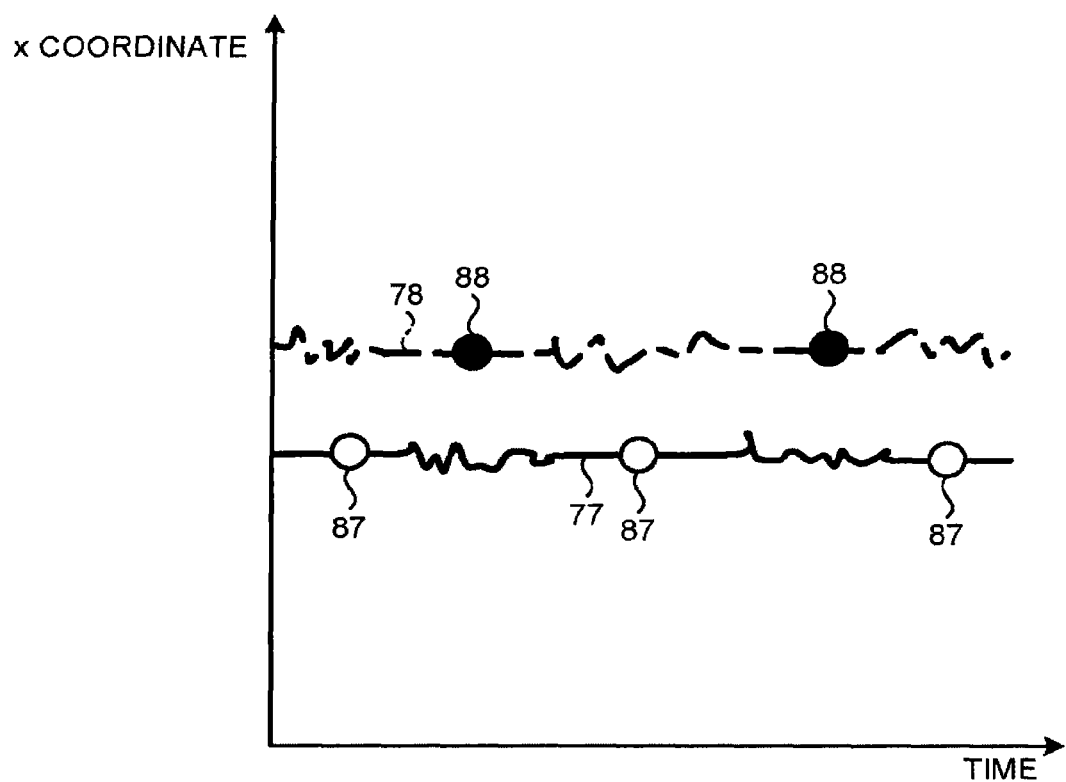
FIG. 25C is a graph for describing an example of an analysis of a landing point of a foot performed by the analyzing circuitry according to the third embodiment by using an x coordinate.

Next, a case of determining a landing point of a foot by using an x coordinate will be described. FIG. 25C is a graph for describing an example of an analysis of a landing point of a foot performed by the analyzing circuitry 1406 according to the third embodiment by using an x coordinate. For example, the analyzing circuitry 1406 acquires, from all frames, a value of an x coordinate of the joint "$2p$" corresponding to the right tarsus and a value of an x coordinate of the joint "$2t$" corresponding to the left tarsus and generates a graph with a vertical axis as the x coordinate and a horizontal axis as time, as illustrated in FIG. 25C.

That is, as illustrated in a curved line and a point in FIG. 25C, the analyzing circuitry 1406 calculates a curved line 77 indicating a temporal change in the x coordinate of the left tarsus and a curved line 78 indicating a temporal change in the x coordinate of the right tarsus. Then, for example, the analyzing circuitry 1406 determines that a time point at which a value of the x coordinate in each curved line becomes constant is a time point at which a foot is on the ground.

For example, as illustrated in FIG. 25C, the analyzing circuitry 1406 determines that a time point 87 at which a value of an x coordinate becomes constant in a curved line 77 indicating a temporal change in an x coordinate of a left tarsus is a time point at which the left foot touches the ground. Similarly, as illustrated in FIG. 25C, the analyzing circuitry 1406 determines that a time point 88 at which a value of an x coordinate becomes constant in the curved line 78 indicating a temporal change in the x coordinate of the right tarsus is a time point at which the right foot touches the ground. The analyzing circuitry 1406 stores, into the analysis information storage circuitry 1305, skeleton information in a frame corresponding to a time point at which it is determined that a foot touches the ground.

Note that the above-described example is just an example and a coordinate to be used is not limited to the above-described example. That is, for example, there may be a case where not only an x coordinate of a tarsus but also an x coordinate of an ankle or a knee is used. Also, for example, there may be a case where comprehensive determination is made by using not only a change in an x coordinate of a single joint but also a change in an x coordinate of each of two joints of a tarsus and a knee.

Also, in the above-described example, a case of determining that a time point at which a value of an x coordinate of a foot becomes constant is a time point at which the foot touches the ground has been described. However, an embodiment is not limited to this. For example, there may be a case of determining that a time point at which a value of an x coordinate of a foot changes little by little is a time point at which an opposite foot of the foot touches the ground. That is, the analyzing circuitry 1406 determines whether a foot is in the air and determines that the other foot is on the ground when one foot is in the air. For example, when a description is made with FIG. 25C as an example, the analyzing circuitry 1406 determines that a time point at which a value of a z coordinate changes little by little in the curved line 77 indicating a temporal change in the x coordinate of the left tarsus is a time point at which the right foot touches the ground. Similarly, the analyzing circuitry 1406 determines that a time point at which a value of an x coordinate changes little by little in the curved line 78 indicating a temporal change in the x coordinate of the right tarsus is a time point at which the left foot touches the ground.

In the above-described example, a case of determining landing of a foot in normal walking has been described. In the following, a case of determining irregular landing of a foot will be described. When walking training in rehab is executed, for example, there is a case where irregular landing of a foot is caused due to tripping. In the following, determination of irregular landing of a foot by using a value of each of a z coordinate, a y coordinate, and an x coordinate will be described serially.

Figure 25D:
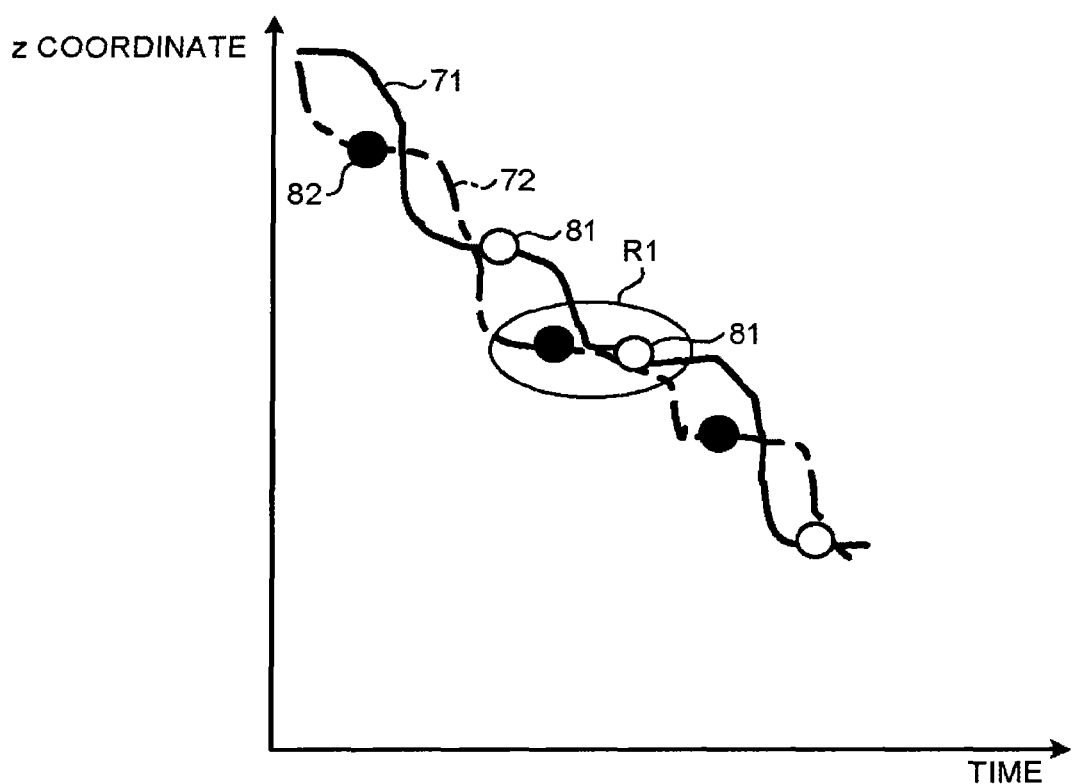
FIG. 25D is a graph for describing an example of an analysis of an irregular landing point performed by the analyzing circuitry according to the third embodiment by using a z coordinate.

First, a case of determining an irregular landing point of a foot by using a z coordinate will be described. FIG. 25D is a graph for describing an example of an analysis of an irregular landing point performed by the analyzing circuitry 1406 according to the third embodiment by using a z coordinate. Here, FIG. 25D is a graph similar to FIG. 25A. For example, as illustrated in FIG. 25D, the analyzing circuitry 1406 determines that a time point in a region R1 in which values of the z coordinate in the curved line 71 indicating a temporal change in the z coordinate of the left tarsus and the curved line 72 indicating a temporal change in the z coordinate of the right tarsus are similar values and there is no change in the values for a certain period of time is a time point at which irregular landing of a foot is caused. Also, for example, the analyzing circuitry 1406 can determine that a time point at which a value of the z coordinate goes back is a time point at which irregular landing of a foot is caused.

Figure 25E:
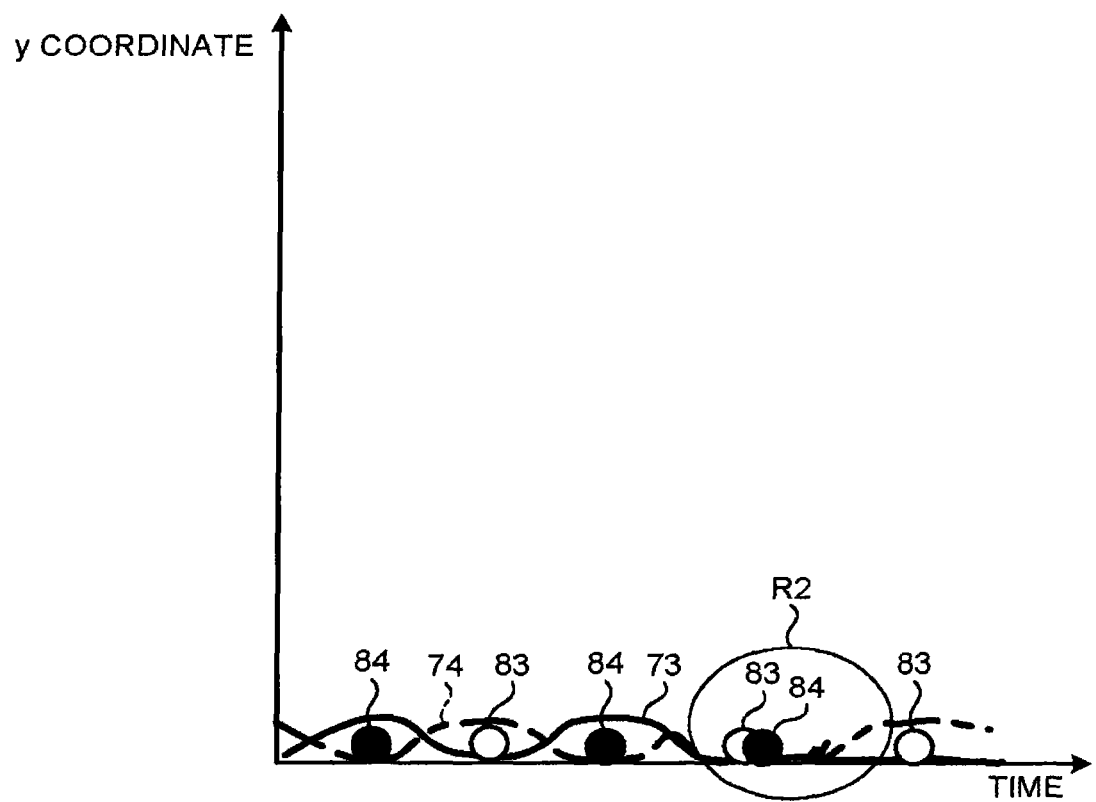
FIG. 25E is a graph for describing an example of an analysis of an irregular landing point performed by the analyzing circuitry according to the third embodiment by using a y coordinate.

Next, a case of determining an irregular landing point of a foot by using a y coordinate will be described. FIG. 25E is a graph for describing an example of an analysis of an irregular landing point performed by the analyzing circuitry 1406 according to the third embodiment by using a y coordinate. Here, FIG. 25E is a graph similar to FIG. 25B. For example, as illustrated in FIG. 25E, the analyzing circuitry 1406 determines that a time point in a region R2, in which a value of the y coordinate becomes "y=0" in each of the curved line 73 indicating a temporal change in the y coordinate of the left tarsus and the curved line 74 indicating a temporal change in the y coordinate of the right tarsus, is a time point at which irregular landing of a foot is caused.

Next, a case of determining an irregular landing point of a foot by using an x coordinate will be described. FIG. 25F is a graph for describing an example of an analysis of an irregular landing point of a foot performed by the analyzing circuitry 1406 according to the third embodiment by using an x coordinate. Here, FIG. 25F is a graph similar to FIG. 25C. For example, as illustrated in FIG. 25F, the analyzing circuitry 1406 determines that a time point 89 in a region R3 in which a value of the x coordinate changes for a degree, which exceeds a predetermined threshold, in the curved line 77 indicating a temporal change in the x coordinate of the left tarsus is a time point at which the left foot touches the ground.

As described above, the analyzing circuitry 1406 can determine an irregular landing point of a foot by using a value of the z coordinate, the y coordinate, or the x coordinate. Thus, for example, the analyzing circuitry 1406 can analyze a landing point of a foot of when a balance is lost during walking training and tripping is performed. Note that the above-described example is just an example and a coordinate to be used is not limited to the above-described example. That is, for example, there may be a case where a coordinate of an ankle or a coordinate of a knee is used in addition to a coordinate of the tarsus. Also, for example, there may be a case where comprehensive determination is made by using not only a change in a coordinate of a single joint but also a change in a coordinate of each of two joints of a tarsus and a knee.

In the above-described example, a case of determining a landing point of a foot by using a single coordinate has been described. However, an embodiment is not limited to this. For example, there may be a case where determination is made by using a plurality of coordinates in a comprehensive manner with respect to each coordinate. For example, there may be a case where a change in the z coordinate and a change in the y coordinate are analyzed and it is determined whether a foot touches the ground based on analysis results. Also, there may be a case where a predetermined coefficient is added to a value of each coordinate. For example, there may be a case where determination is made after a coefficient "a" is added to a value of the y coordinate.

Also, as described above, in addition to determination of landing of a foot, the analyzing circuitry 1406 can make determination that a foot is in the air. That is, for example, when a right foot is in the air during walking, the analyzing circuitry 1406 can determine that a left foot is on the ground. Also, by previously inputting coordinates of the ground into a system, the analyzing circuitry 1406 can determine that a foot is on the ground when the foot becomes close to the coordinates of the ground.

As described above, the analyzing circuitry 1406 analyzes a position (coordinate) of a landing point of a foot. Accordingly, for example, the analyzing circuitry 1406 analyzes an overlapped walking distance, a stride, a step interval, the number of steps, a walking rate, walking time, a period of time in which a foot is on the ground, or the like based on the analyzed position of the landing point. That is, the analyzing circuitry 1406 analyzes the above-described various kinds of information by using coordinates of the landing point. Here, the analyzing circuitry 1406 can calculate an overlapped walking distance, a stride, a step interval, or the like with a walking direction as a basis.

Note that in FIG. 25A to FIG. 25F described above, a case where the object person walks in a depth direction (z-axis direction) (case of walking along z-axis toward motion information collecting circuitry 10) has been described as an example. However, a walking direction of an object person is arbitrary and the analyzing circuitry 1406 can correspond to the direction. First, a case of walking away from the motion information collecting circuitry 10 along the z-axis will be described. In such a case, the analyzing circuitry 1406 can determine a landing point of a foot by the above-described method in any of the z coordinate, y coordinate, and x coordinate. Note that in this case, in a graph of the z coordinate, a value of the z coordinate increases as time passes.

Next, a case where the object person walks along the x-axis will be described. That is, a case where the object person passes in front of the motion information collecting circuitry 10 from the right to the left or from the left to the right will be described. In such a case, the analyzing circuitry 1406 can use, with respect to the x coordinate, the determination method of a landing point of a foot in the z coordinate which method has been described in FIG. 25A and FIG. 25D. That is, in a case where the object person walks along the x-axis, the x coordinate changes along with the walking. Thus, the analyzing circuitry 1406 determines that a foot is on the ground when a change in a value of the x coordinate in a unit time is smaller than a predetermined threshold. Note that when in each of a case where the object person passes in front of the motion information collecting circuitry 10 from the right to the left and a case where the object person passes in front of the motion information collecting circuitry 10 from the left to the right, the value of the x coordinate increases or decreases as time passes.

Also, when the object person walks along the x-axis, the analyzing circuitry 1406 can use, with respect to the z coordinate, the determination method of a landing point of a foot in the x coordinate which method has been described in FIG. 25C and FIG. 25F. For example, the analyzing circuitry 1406 determines that a time point at which a value of the z coordinate is constant is a time point at which a foot is on the ground. Note that the analyzing circuitry 1406 can determine, with respect to the y coordinate, a landing point of a foot by using the above-described method.

Next, a case where an object person walks diagonally in a space where motion information is collected by the motion information collecting circuitry 10 (case of not walking along z-axis and x-axis) will be described. In such a case, for example, when a movement amount in a unit time of a joint corresponding to a tarsus in xz coordinates (direction horizontal to ground) or the like is smaller than a predetermined threshold, the analyzing circuitry 1406 determines that a foot on a side of the tarsus is on the ground. Note that the analyzing circuitry 1406 can determine, with respect to the y coordinate, a landing point of a foot by using the above-described method.

Next, a case where the object person does not walk in one direction in a space where motion information is collected by the motion information collecting circuitry 10 (such as a case of making round trip, zigzagging, or walking around) will be described. Similarly to a case of walking diagonally, in such a case, for example, when a movement amount in a unit time of a joint corresponding to a tarsus in xz coordinates (direction horizontal to ground) or the like is smaller than a predetermined threshold, the analyzing circuitry 1406 determines that a foot on a side of the tarsus is on the ground. Note that the analyzing circuitry 1406 can determine, with respect to the y coordinate, a landing point of a foot by using the above-described method.

As described above, by using the motion information obtained by the obtaining circuitry 1405, the analyzing circuitry 1406 analyzes a position of landing point of a foot of the object person who executes a walking motion. Here, the analyzing circuitry 1406 can further analyze an angle of a body of the object person. In the following, a case of analyzing an angle will be described. In such a case, the analyzing circuitry 1406 further calculates, as a walking state, an angle between a predetermined basis and a predetermined part of the object person.

Here, for example, the analyzing circuitry 1406 according to the third embodiment analyzes an angle similarly to FIG. 8 described above. Note that in FIG. 8, a case of calculating, by using skeleton information in motion information collected by the motion information collecting circuitry 10, an angle between a predetermined basis in a world coordinate system and a predetermined part of the body of the object person during walking. Here, (A) in FIG. 8 is a part illustrating skeleton information in a world coordinate system of an object person executing walking training. Also, (B) to (D) in FIG. 8 are parts illustrating examples of calculation of an angle.

By using skeleton information in each frame which information is obtained by the obtaining circuitry 1405, the analyzing circuitry 1406 calculates an angle between a predetermined basis in the world coordinate system and a predetermined part of the body of the object person. For example, as illustrated in (A) in FIG. 8, when the object person executes walking training in a direction of an arrow in a z-axis direction in a predetermined space (space where motion information collecting circuitry 10 can collect coordinate information) in the world coordinate system, the analyzing circuitry 1406 can calculate various angles such as what has been described in each of (B) to (D) in FIG. 8.

For example, as illustrated in (B) in FIG. 8, the analyzing circuitry 1406 calculates an angle "$\theta 1$," in a vertical direction on an xy plane, of an axis (body axis) from the joint "$2a$" corresponding to a head to a joint "$2d$" corresponding to a center part of a hip. In such a case, the analyzing circuitry 1406 calculates a straight line which passes coordinate information (x1, y1) of the joint "$2a$" corresponding to the head and coordinate information (x4, y4) of the joint "2d" corresponding to the center part of the hip in a predetermined frame and calculates, as the angle "θ1," an angle between the calculated straight line and a straight line in parallel with the y-axis. That is, the analyzing circuitry 1406 calculates a degree of an angle to the right/left of when the object person is seen from the front (right/left angle of object person).

Also, for example, as illustrated in (C) in FIG. 8, the analyzing circuitry 1406 calculates an angle "θ2," in a horizontal direction on an xz plane, of an axis from a joint "2e" corresponding to a right shoulder to a joint "2i" corresponding to a left shoulder. In such a case, the analyzing circuitry 1406 calculates a straight line which passes through coordinate information (x5, z5) of the joint "2e" corresponding to the right shoulder and coordinate information (x9, z9) of the joint "2i" corresponding to the left shoulder in a predetermined frame and calculates, as the angle "θ2," an angle between the calculated straight line and a straight line in parallel with the x-axis. That is, the analyzing circuitry 1406 calculates a degree of shaking of a body in a rotation direction centering on a body axis of when the object person is seen from the above. Note that the analyzing circuitry 1406 can also calculate various angles in a traveling direction in walking which direction is indicated by an arrow in (C) in FIG. 8, although not illustrated.

Also, for example, as illustrated in (D) in FIG. 8, the analyzing circuitry 1406 calculates an angle "θ3," in a vertical direction on a yz plane, of an axis (body axis) from the joint "2a" corresponding to the head to the joint "2d" corresponding to the center part of the hip. In such a case, the analyzing circuitry 1406 calculates a straight line which passes through coordinate information (y1, z1) of the joint "2a" corresponding to the head and coordinate information (y4, z4) of the joint "2d" corresponding to the center part of the hip in a predetermined frame and calculates, as the angle "θ3," an angle between the calculated straight line and a straight line which is in parallel with the y-axis. That is, the analyzing circuitry 1406 calculates a degree of an angle to the right/left in a case where the object person is seen from a side (forward/backward angle of object person).

Also, the analyzing circuitry 1406 can use, as a predetermined basis, a part of a body of the object person. Here, for example, the analyzing circuitry 1406 according to the third embodiment analyzes an angle similarly to FIG. 9 described above. In FIG. 9, a case of calculating an angle between a part of a body of an object person and a predetermined part of the body of the object person during walking by using skeleton information in the motion information collected by the motion information collecting circuitry 10 is illustrated. Here, (A) in FIG. 9 is a part illustrating skeleton information in a world coordinate system of an object person executing walking training. Also, (B) in FIG. 9 is a part illustrating examples of calculation of an angle.

By using skeleton information in each frame which information is obtained by the obtaining circuitry 1405, the analyzing circuitry 1406 calculates an angle between a part of a body of the object person and a predetermined part of the body of the object person. For example, as illustrated in (A) in FIG. 9, when the object person executes walking training in a direction of an arrow in a z-axis direction in a predetermined space (space where motion information collecting circuitry 10 can collect coordinate information) in the world coordinate system, the analyzing circuitry 1406 can calculate various angles between a part of the body of the object person and a predetermined part of the body of the object person.

For example, as illustrated in (B) in FIG. 9, the analyzing circuitry 1406 calculates an angle "θ4" between a bone, which connects the joint "2e" corresponding to the right shoulder and a joint "2f" corresponding to a right elbow, and a bone which connects the joint "2f" corresponding to the right elbow and a joint "2g" corresponding to a right wrist. That is, the analyzing circuitry 1406 analyzes an angle of a right arm (right elbow) of the object person in a walking motion. In such a case, the analyzing circuitry 1406 calculates a straight line which passes through coordinate information (x5, y5, z5) of the joint "2e" corresponding to the right shoulder and coordinate information (x6, y6, z6) of the joint "2f" corresponding to the right elbow in a predetermined frame. Moreover, the analyzing circuitry 1406 calculates a straight line which passes through the coordinate information (x6, y6, z6) of the joint "2f" corresponding to the right elbow and coordinate information (x7, y7, z7) of the joint "2g" corresponding to the right wrist. Then, the analyzing circuitry 1406 calculates, as the angle "θ4," an angle between the two calculated straight lines.

In such a manner, by using coordinate information (x, y, z) of skeleton information in each frame which information is collected by the motion information collecting circuitry 10, the analyzing circuitry 1406 can calculate an angle between a predetermined basis and a predetermined part of the object person. Note that the example illustrated in each of (B) to (D) in FIG. 8 and (B) in FIG. 9 is just an example. That is, the analyzing circuitry 1406 can calculate an angle between a basis set arbitrarily by an operator and an arbitrarily-selected part of a body in each frame.

Here, an angle to be analyzed can be set arbitrarily as described above. For example, it is possible to perform setting in such a manner that an angle prescribed in a "range of joint motion display and measurement method (The Japan Orthopaedic Association and The Japanese Association of Rehabilitation Medicine): http://ci.nii.ac.jp/naid/110001856130" is measured. Also, for example, a reference plane on a body (sagittal plane, horizontal plane, or frontal plane) can be used as a set basis. Also, for example, it is possible to preset an initial state of an object person as a basis and to analyze a difference between a state during walking and the initial state.

Next, a case of analyzing velocity will be described. When analyzing velocity, the analyzing circuitry 1406 calculates a moving distance [m] of a coordinate corresponding to a predetermined part of the object person in a predetermined period of time (such as 0.5 second). Then, based on the calculated moving distance in a predetermined period of time, the analyzing circuitry 1406 calculates moving velocity [m/second] of the object person in the predetermined period of time. Here, the analyzing circuitry 1406 can also calculate, as velocity of walking of the object person, an average value of moving velocity of the object person during walking training. For example, the analyzing circuitry 1406 calculates moving velocity of a part instructed by the operator through the input circuitry 120 (such as any of joints or part of body lead from each joint).

Also, the analyzing circuitry 1406 calculates acceleration by using the calculated velocity. More specifically, the analyzing circuitry 1406 calculates acceleration (change rate of velocity in unit time) by using the velocity in a unit time which velocity is calculated by the above-described method.

Figure 26:
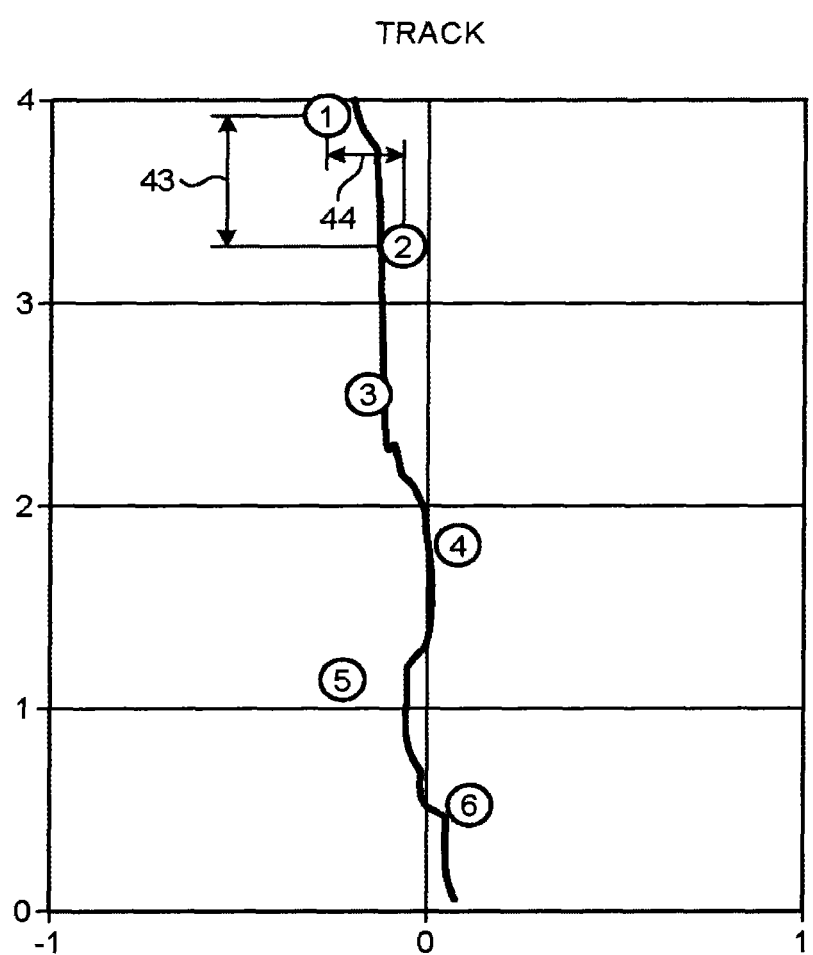
FIG. 26 is a graph for describing an example of measurement processing performed by the analyzing circuitry according to the third embodiment.

Next, a case of analyzing a distance will be described. The analyzing circuitry 1406 measures a distance or the like between predetermined parts of the object person which distance is collected by the motion information collecting circuitry 10. For example, the analyzing circuitry 1406 measures a stride, a step interval, a distance between joints, or the like of the object person. FIG. 26 is a graph for describing an example of measurement processing performed by the analyzing circuitry 1406 according to the third embodiment. FIG. 26 is a graph in which xz coordinates in the world coordinate system where the object person executes walking training is indicated by a region of four meters by two meters and a foot print of the object person and a track of a body of the object person are indicated in the region.

For example, as illustrated in FIG. 26, the analyzing circuitry 1406 calculates a distance of a stride 43 or a step interval 44. For example, when information of a foot print and a track of a body which information is illustrated in FIG. 26 is displayed on output circuitry 110 and an operator inputs a measurement request of each distance through the input circuitry 120, the analyzing circuitry 1406 calculates the stride 43 based on a value of a z coordinate in coordinate information corresponding to a first step and a value of a z coordinate in coordinate information corresponding to a second step. Similarly, the analyzing circuitry 1406 calculates the step interval 44 based on a value of an x coordinate in the coordinate information corresponding to the first step and a value of an x coordinate in the coordinate information corresponding to the second step.

Note that the above-described example is just an example and it is possible to arbitrarily execute measurement of a distance. For example, with a measurement function of the analyzing circuitry 1406, it is possible to calculate a distance from a foot print of a first step to a foot print of a second step based on values of an x coordinate and a z coordinate in coordinate information corresponding to the first step and values of an x coordinate and a z coordinate in coordinate information corresponding to the second step. Also, the analyzing circuitry 1406 can calculate a distance of movement of a value of the x coordinate between predetermined frames by acquiring a value of the x coordinate in each frame of the same part of the object person (such as joint "2a" corresponding to head). Note that frames in such a case can be set arbitrarily. For example, it is also possible to perform calculation between a frame of a time point at which a right foot touches the ground and a frame of a time point at which a left foot touches the ground.

Also, in measurement processing performed by the analyzing circuitry 1406, it is also possible to measure time information. For example, the analyzing circuitry 1406 can measure a period of time between a first step and a second step in walking by the object person, a period of time of landing in each step, a period of time spent for single walking training, or the like. Also, the analyzing circuitry 1406 can measure a walking rate (number of steps in unit time) or the like by using the measured time. In the above, an example of measurement processing performed by the analyzing circuitry 1406 has been described. Here, the above-described measurement processing performed by the analyzing circuitry 1406 can be performed according to an instruction from the operator or can be performed automatically.

As described above, the analyzing circuitry 1406 executes various kinds of analysis by using skeleton information of the object person in each frame which information is obtained by the obtaining circuitry 1405. Also, by using an analysis result, the analyzing circuitry 1406 can determine whether walking by the object person is stable or can predict future walking by the object person.

For example, when determining a shake of a body or the like with respect to walking executed by the object person, the analyzing circuitry 1406 determines the shake of the body or the like of the object person during walking with a previously-set threshold as a determination basis. For example, when a threshold of a shake during walking is set, the analyzing circuitry 1406 analyzes a movement in a rotation direction centering on a body axis of the object person during walking based on motion information (such as change in value of coordinate of joint corresponding to head in xz coordinate) of the object person and determines whether the shake in the rotation direction centering on the body axis exceeds a threshold.

Then, when the shake in the rotation direction centering on the body axis exceeds the threshold, the analyzing circuitry 1406 determines that walking of the object person is not stable. Then, the analyzing circuitry 1406 notifies a determination result to the display controlling circuitry 1407 described later. Accordingly, the display controlling circuitry 1407 described later can display warning in a case where it is determined that walking by the object person is not stable or can display display information for notifying that walking is stable while the walking is stable. In such a manner, the analyzing circuitry 1406 determines an analysis result by using a previously-set predetermined threshold. However, the above-described example is just an example and various kinds of different determination can be performed. For example, the analyzing circuitry 1406 can determine whether walking by the object person is stable based on an angle of a body, velocity, a stride, a step interval, or the like of the object person during walking. That is, a threshold in each piece of analysis information is set previously. The analyzing circuitry 1406 compares a value of each piece of analysis information with the set threshold and determines whether the walking by the object person is stable.

Also, in a case of predicting future walking by the object person, for example, the analyzing circuitry 1406 acquires data of a position of a landing point of a foot, a stride, and a step interval from data of previous walking of the same person performing walking training. Then, the analyzing circuitry 1406 extracts data of a position of a landing point of a foot, a stride, and a step interval in data of walking which data is collected in current walking training and compares the extracted data with previous data. Here, the analyzing circuitry 1406 calculates how the walking by the object person changes from a date the previous data is collected to a date the current data is collected and predicts how the walking by the object person changes in the future (when predetermined time passes). For example, the analyzing circuitry 1406 predicts how each of a position of a landing point of a foot, a stride, and a step interval changes in one month.

Also, for example, the analyzing circuitry 1406 can estimate an effect of rehab in the walking training based on data of walking by a different person executing the same walking training instead of that of the same object person and can predict how the walking by the object person changes. In such a case, the analyzing circuitry 1406 predicts how the walking by the object person changes in the future by analyzing what kind of change is caused in a predetermined period based on the data of the different person and by applying a result of the analysis to data of walking by the object person at a current time point.

Also, the analyzing circuitry 1406 can determine whether actual walking is greatly different from predicted walking by analyzing a difference between the predicted walking and the actual walking. In such a case, an acceptable range of a difference from a state of the predicted walking (such as position of landing point of foot, stride, or step interval) is previously set. The analyzing circuitry 1406 calculates a difference between the predicted walking and the actual walking and determines whether the calculated difference is in the previously-set acceptable range. Here, when the calculated difference exceeds the acceptable range, the analyzing circuitry 1406 determines that the actual walking is greatly different from the predicted walking. Then, the analyzing circuitry 1406 notifies a determination result to the display controlling circuitry 1407 described later. Accordingly, the display controlling circuitry 1407 described later can display warning in a case where it is determined that the actual walking is greatly different from the predicted walking or can display display information to notify that the actual walking is not greatly different from the predicted walking.

Also, when the object person actually executes walking training, the analyzing circuitry 1406 can predict walking in real time. For example, the analyzing circuitry 1406 predicts a next step based on an analysis result of the walking by the object person executing the walking training. For example, the analyzing circuitry 1406 predicts a third step (such as position of landing point of foot or stride) based on analysis results of a first step and a second step of the object person. Here, there may be a case where the analyzing circuitry 1406 uses two analysis results of the first step and the second step or a case where the analyzing circuitry 1406 uses only the analysis result of the second step.

Then, the analyzing circuitry 1406 determines whether the actual walking is greatly different from the predicted walking. For example, the analyzing circuitry 1406 calculates a difference between a predicted third step and an actual third step and determines whether the calculated difference is in a previously-set acceptable range. Here, when the calculated difference exceeds the acceptable range, the analyzing circuitry 1406 determines that the actual third step is greatly different from the predicted third step. Then, the analyzing circuitry 1406 notifies a determination result to the display controlling circuitry 1407 described later. Accordingly, the display controlling circuitry 1407 described later can display warning in real time in a case where it is determined that the actual walking is greatly different from the predicted walking or can display, in real time, display information to notify that the actual walking is not greatly different from the predicted walking.

Note that the above-described example is just an example and an object of prediction is not limited to the above-described example. For example, the analyzing circuitry 1406 can also predict an angle of a body of the object person or how a leg is lifted based on motion information (skeleton information) of the object person.

Then, as described above, the analyzing circuitry 1406 executes various kinds of analysis according to walking by the object person based on motion information of the object person. Then, the analyzing circuitry 1406 outputs the above-described analysis result to the display controlling circuitry 1407.

Referring back to FIG. 23, the display controlling circuitry 1407 performs control in such a manner that walking information analyzed by the analyzing circuitry 1406 is displayed on the output circuitry 110. More specifically, the display controlling circuitry 1407 performs control in such a manner that analysis information stored in the analysis information storage circuitry 1305 is displayed on the output circuitry 110. In the following, with reference to FIG. 27 to FIG. 30, an example of an analysis result displayed according to control performed by the display controlling circuitry 1407 will be described. Each of FIG. 27 to FIG. 30 is a view illustrating an example of an analysis result displayed according to control by the display controlling circuitry 1407 according to the third embodiment.

Figure 27:
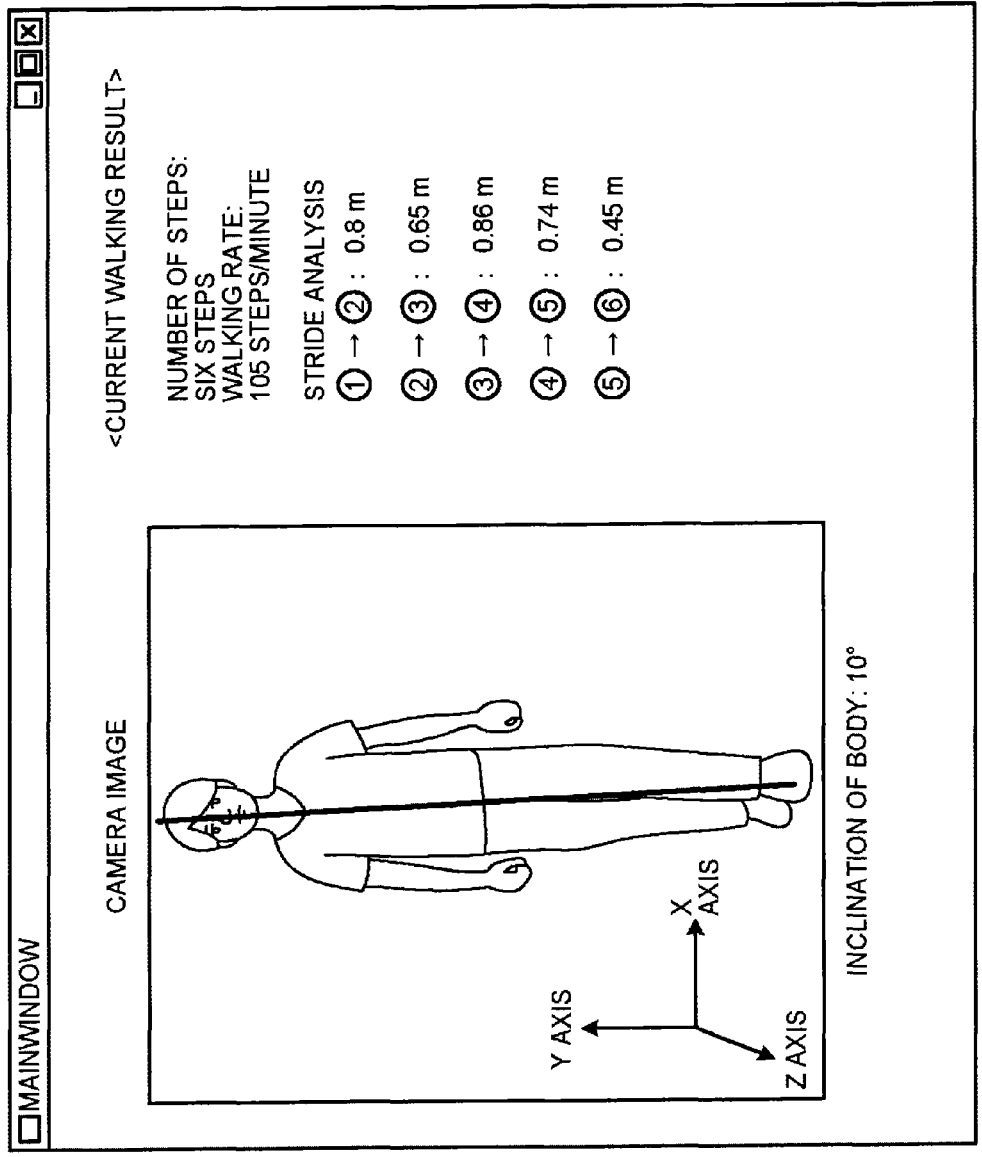
FIG. 27 is a view illustrating an example of an analysis result displayed by control performed by display controlling circuitry according to the third embodiment.

For example, as illustrated in FIG. 27, the display controlling circuitry 1407 displays, on the output circuitry 110, analysis information in which a camera image is arranged on a left-side region in a "MainWindow" and a <current walking result> is arranged on a right side thereof. Here, as illustrated in FIG. 27, the display controlling circuitry 1407 superimposes, on the camera image, a straight line indicating a body axis of the object person and information of three axes and displays an analysis result of a body angle, "body angle: 10°." Then, the display controlling circuitry 1407 displays, as the <current walking result>, the "number of steps: six steps," a "walking rate: 105 steps/minute," and a "stride analysis" which is an analysis result of a stride between steps. Accordingly, the operator can evaluate a walking condition of the object person at a glance.

Figure 28:
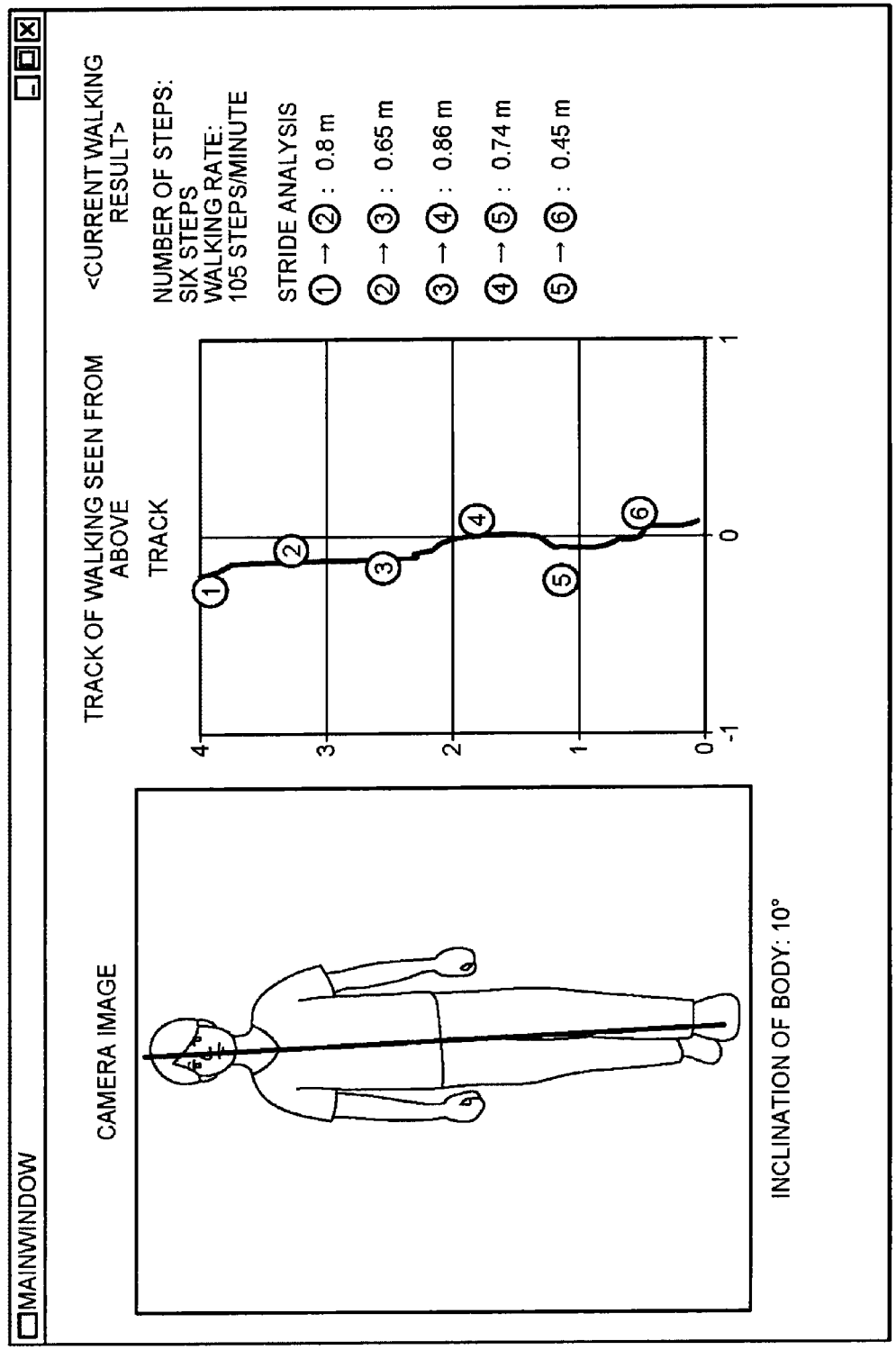
FIG. 28 is a view illustrating an example of an analysis result displayed by control performed by the display controlling circuitry according to the third embodiment.

Here, the analysis information illustrated in FIG. 27 is just an example. That is, the display controlling circuitry 1407 further displays various kinds of information on the output circuitry 110. For example, as illustrated in FIG. 28, the display controlling circuitry 1407 can display, on the output circuitry 110, a "track of walking seen from the above" in addition to the camera image and the <current walking result> illustrated in FIG. 27. Such information is an example of information indicating a landing point of a foot and a track of a body of the object person which information is analyzed by the analyzing circuitry 1406. Accordingly, the operator can further see information of a foot print and a track of a body from the above, which information cannot be seen in a camera image displayed two-dimensionally, and can evaluate an analysis result of a stride analysis or the like.

Also, the display controlling circuitry 1407 can display, on the output circuitry 110, not only an analysis result according to walking but also analysis information in which an angle of a part of a body is analyzed. For example, as illustrated in FIG. 29, the display controlling circuitry 1407 displays, on the output circuitry 110, analysis information in which the camera image is arranged in the left-side region in the "MainWindow" and a graph of an "Arm Angle" indicating analysis information of an angle of an arm is arranged on a right side thereof.

Figure 29:
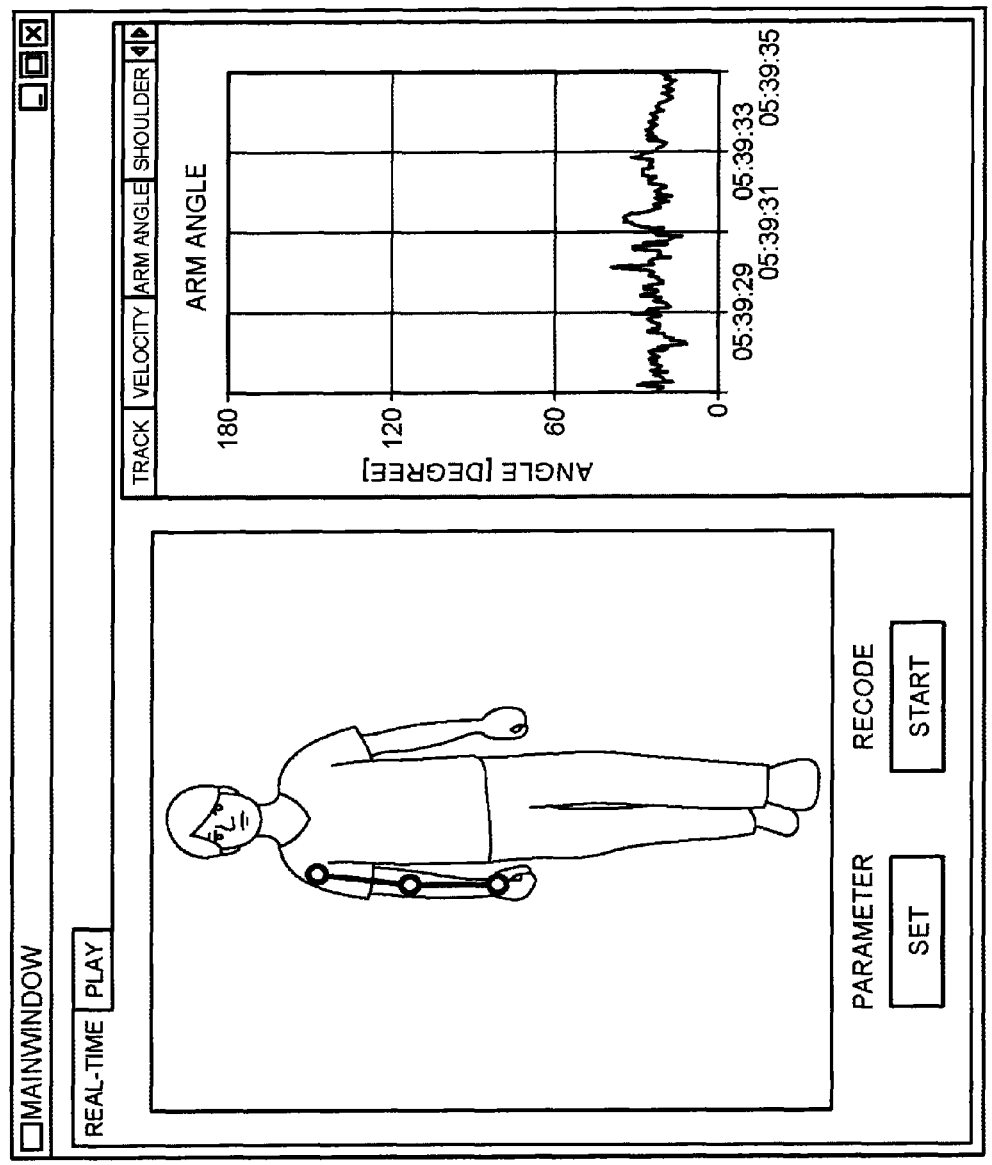
FIG. 29 is a view illustrating an example of an analysis result displayed by control performed by the display controlling circuitry according to the third embodiment.

Here, for example, as illustrated in FIG. 29, the display controlling circuitry 1407 can clearly indicate the analyzed angle of the arm on the camera image. That is, as illustrated in FIG. 29, the display controlling circuitry 1407 indicates each of a joint corresponding to a right shoulder, a joint corresponding to a right elbow, and a joint corresponding to a right wrist as a point and displays information, in which these points are connected to each other with a line, while superimposing the information on an image in such a manner that joints of a right arm which is an analysis object of the "Arm Angle" is indicated clearly.

Note that a display format by the display controlling circuitry 1407 may be a display format illustrated in each of FIG. 27 and FIG. 28 or a display format illustrated in FIG. 29. That is, as illustrated in FIG. 29, the display controlling circuitry 1407 displays, on a left side in a tab displayed in real time, a window including a region to display image information, a "PARAMETER" SET button to set a parameter, and a "RECODE" START button to execute a start and an end of recording.

Also, the display controlling circuitry 1407 displays, on a right side of the same tab, a window including tabs to switch displaying of graphs indicated by a "Track," "Velocity," an "Arm Angle," a "Shoulder Angle," and the like. That is, when a tab is clicked by the operator, the display controlling circuitry 1407 can display information corresponding to the clicked tab. For example, in a case of the "Arm Angle," as illustrated in FIG. 27, the display controlling circuitry 1407 displays a graph with a vertical axis as an angle "Angle [degree]" and a horizontal axis as time.

Figure 30:
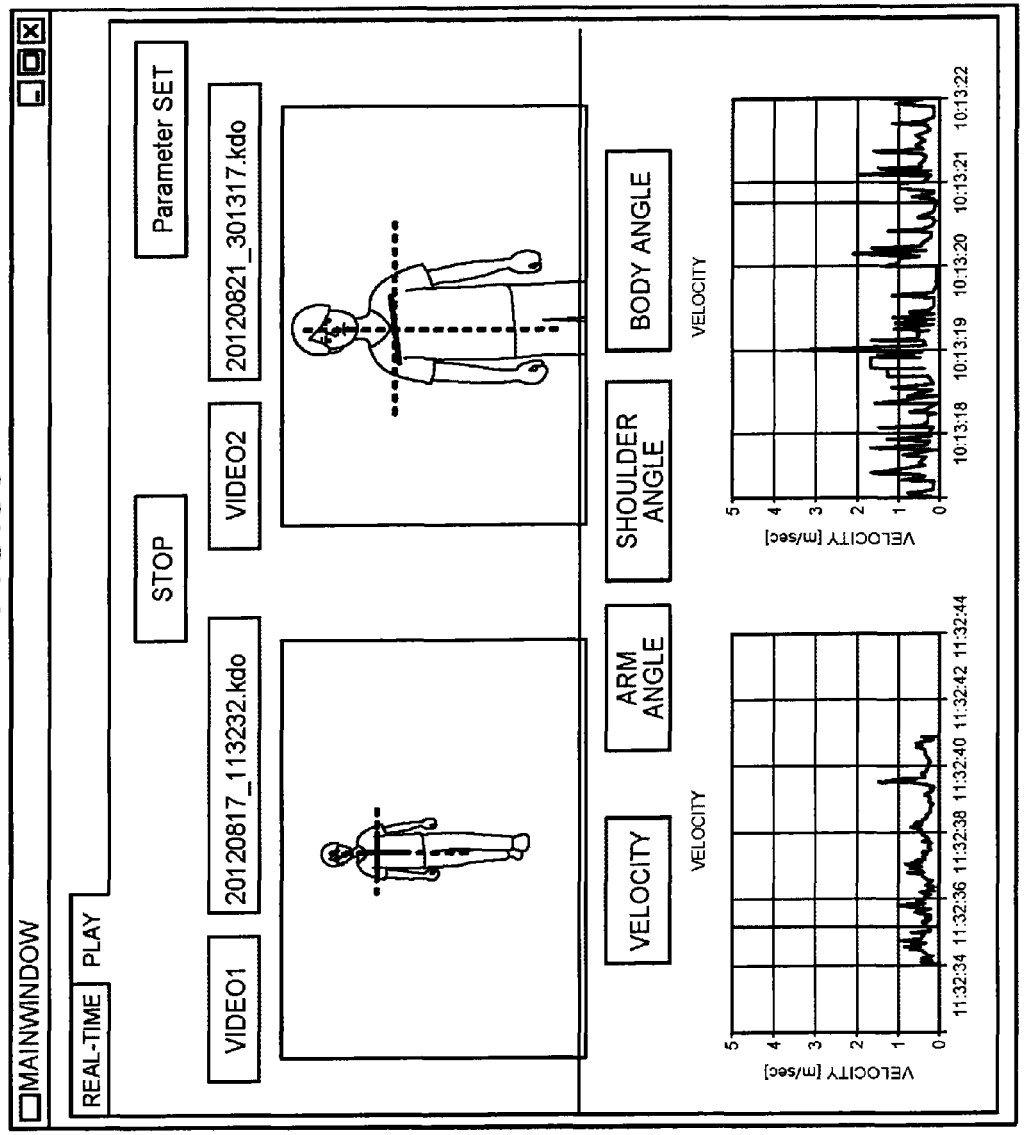
FIG. 30 is a view illustrating an example of an analysis result displayed by control performed by the display controlling circuitry according to the third embodiment.

Also, the display controlling circuitry 1407 can display a plurality of results in parallel. For example, as illustrated in FIG. 30, the display controlling circuitry 1407 displays pieces of walking data in different periods respectively on right and left parts of the window. For example, the display controlling circuitry 1407 displays image information and graph information respectively on the right and left regions. Here, the display controlling circuitry 1407 displays, in these regions, information designated by the operator.

That is, the display controlling circuitry 1407 displays image information such as the color image information or the superimposed image information on an upper side of each of the right and the left regions and displays a track of a foot print or graph information on a lower side of each of the right and the left regions. Here, an object of a comparison display is not limited to data of the same object person. A parallel display with data of a different person can be performed. Thus, for example, the display controlling circuitry 1407 can display pieces of walking data of the same person in different periods in parallel or can display data of a person with a handicap in his/her leg and that of a person with no handicap in his/her leg in parallel.

Note that, for example, as illustrated in FIG. 30, in the window in which pieces data of a plurality of object people are displayed in parallel, a selection region for selection of the analysis information stored in the analysis information storage circuitry 1305, a "Parameter SET" button for selection of a parameter to be displayed, a switch button for switching a graph, or the like is displayed.

Also, the display controlling circuitry 1407 can display, on the output circuitry 110, a determination result indicating whether walking executed by the object person is stable, a prediction result of future walking, or the like. For example, in a case of displaying the determination result, the display controlling circuitry 1407 displays warning by coloring a whole region, where image information is displayed, in red or outputs sound.

Also, in a case of displaying the prediction result, the display controlling circuitry 1407 performs a parallel display with an analysis result in which walking is analyzed in real time or performs a superimposed display onto an analysis result of walking at a current time point.

Also, the display controlling circuitry 1407 can output, from the output circuitry 110, not only the above-described information but also various kinds of different information by using information analyzed by the analyzing circuitry 1406. For example, by using the analysis information analyzed by the analyzing circuitry 1406, the display controlling circuitry 1407 can generate track information, superimposed image information, or the like described in the first and second embodiments and can output the generated information from the output circuitry 110. Here, also in the motion information processing apparatus 100*a* according to the third embodiment, there may be a case where a generating circuitry 1403 illustrated in FIG. 4 is included and the generating circuitry 1403 generates display information by using analysis information analyzed by the analyzing circuitry 1406.

Figure 31:
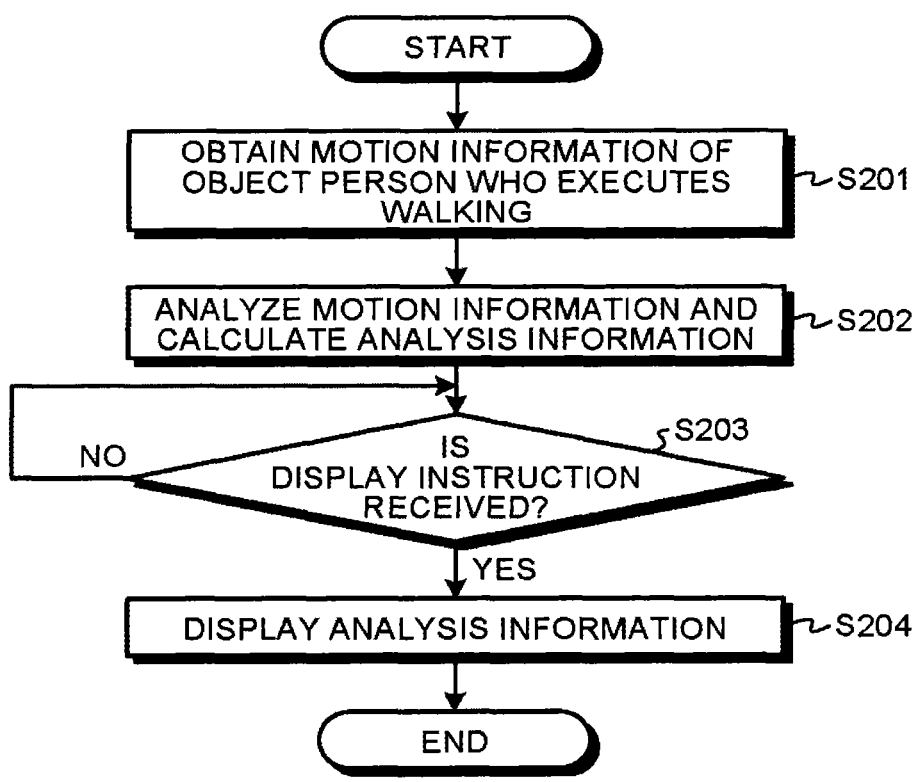
FIG. 31 is a flowchart illustrating a procedure of processing performed by the motion information processing apparatus according to the third embodiment.

Next, with reference to FIG. 31, processing in the motion information processing apparatus 100*a* according to the third embodiment will be described. FIG. 31 is a flowchart illustrating a procedure of processing performed by the motion information processing apparatus 100*a* according to the third embodiment. Note that in FIG. 31, a case of displaying an analysis result is illustrated.

As illustrated in FIG. 31, in the motion information processing apparatus 100*a* according to the third embodiment, when walking training is started, the obtaining circuitry 1405 obtains motion information of an object person who executes the walking (step S201). Then, the analyzing circuitry 1406 analyzes the acquired motion information and calculates analysis information (step S202). Then, the display controlling circuitry 1407 determines whether a display operation is received (step S203).

Here, when the display instruction is received (yes in step S203), the display controlling circuitry 1407 performs control in such a manner that the analysis information is displayed on the output circuitry 110 (step S204). Note that calculation of analysis information is kept performed until the display instruction is received (no in step S203).

As described above, according to the third embodiment, the obtaining circuitry 1405 obtains motion information of the object person executing a walking motion. Then, the analyzing circuitry 1406 analyzes a walking state including a position, where a foot of the object person touches a ground, based on a temporal change in a position of a predetermined part of the object person in the motion information obtained by the obtaining circuitry 1405. Thus, the motion information processing apparatus 100*a* according to the third embodiment can provide an analysis result of a walking state including a landing point of a foot to an operator and can make it easy to evaluate a walking condition. As a result, the motion information processing apparatus 100*a* according to the third embodiment makes it possible to control a difference in evaluation of the walking among doctors, physical therapists, and the like.

Also, according to the third embodiment, the analyzing circuitry 1406 determines whether a foot of the object person is on the ground based on a temporal and three-dimensional change in a position of a predetermined part of the object person in the motion information obtained by the obtaining circuitry 1405. When it is determined that the foot is on the ground, a position of the foot of the object person at a time point of the determination is set as a landing point. Thus, the motion information processing apparatus 100*a* according to the third embodiment can analyze a position of a landing point of a foot based on a movement of each of various parts of the object person during walking and can make it possible to extract landing of the foot accurately.

Also, according to the third embodiment, the analyzing circuitry 1406 determines the landing of the foot of the object person based on a change amount in a unit time of a predetermined part in the foot of the object person. Thus, the motion information processing apparatus 100*a* according to the third embodiment makes it possible to accurately determine whether the foot of the object person is kept still.

Also, according to the third embodiment, based on a change amount of a position of a predetermined part in one foot of the object person, the analyzing circuitry 1406 determines landing of an opposite foot of the one foot. Thus, the motion information processing apparatus 100*a* according to the third embodiment makes it possible to determine landing of a foot based on a movement of an opposite foot of the landing foot.

Also, according to the third embodiment, the analyzing circuitry 1406 analyzes a change amount in a unit time of a position of a predetermined part in a traveling direction of walking by the object person, a body axis direction, or a direction orthogonal to the traveling direction. Thus, the motion information processing apparatus 100*a* according to the third embodiment can analyze a position of a landing point of a foot based on simple coordinate information in a space where a walking motion is executed by the object person and can make it possible to provide analysis information which can be easily recognized by the operator.

Also, according to the third embodiment, the analyzing circuitry 1406 analyzes a change amount in a unit time of a position of a predetermined part in at least two or more of a traveling direction, a body axis direction, and a direction orthogonal to the traveling direction. Thus, the motion information processing apparatus 100*a* according to the third embodiment can correspond to a complicated movement in determination whether the foot of the object person is on the ground.

Also, according to the third embodiment, the analyzing circuitry 1406 calculates a traveling direction based on a change in a position in walking by the object person. More specifically, the analyzing circuitry 1406 sets a direction in which a value of a position increases/decreases along with the walking by the object person as a traveling direction, a direction in which a value of a position varies in a predetermined range during the walking by the object person as a body axis direction, and a direction in which a value of a position is substantially constant during the walking by the object person as a direction orthogonal to the traveling direction. Thus, the motion information processing apparatus 100*a* according to the third embodiment can correspond to a case where the object person walks in any direction.

Also, according to the third embodiment, the analyzing circuitry 1406 further calculates, as a walking state, an angle between a predetermined basis and a predetermined part of the object person. Thus, the motion information processing apparatus 100*a* according to the third embodiment makes it possible to easily provide an important parameter for evaluation of a walking condition.

Also, according to the third embodiment, based on an analyzed position of a landing point of a foot of the object person, the analyzing circuitry 1406 predicts a landing point of a foot of the object person. Thus, the motion information processing apparatus 100*a* according to the third embodiment makes it possible to evaluate a degree of recovery of the object person, optimality of walking training with respect to the object person, or walking training itself.

Also, according to the third embodiment, the display controlling circuitry 1407 performs control in such a manner that walking information analyzed by the analyzing circuitry 1406 is displayed on the output circuitry 110. Thus, the motion information processing apparatus 100*a* according to the third embodiment can provide analysis information to an operator as visual information and can make it easier to evaluate a walking condition.

Fourth Embodiment

In the above, the third embodiment has been described. However, there are various different embodiments other than the above-described third embodiment.

In the above-described third embodiment, a case of analyzing a position of a landing point of a foot or the like by only using information related to walking by an object person has been described. However, an embodiment is not limited to this. For example, there may be a case of using unique information of an object person. That is, analyzing circuitry 1406 analyzes a position of a landing point of a foot of an object person based on a unique motion or instrument of the object person which motion or instrument is included in motion information of the object person executing a walking motion which information is obtained by obtaining circuitry 1405.

For example, there may be a case of determining a position of a landing point of a foot based on a characteristic of the object person during walking (such as leg being dragged or stick or walking shoes being used). In such a case, for example, the analyzing circuitry 1406 may acquire personal information from a medical information system or a personal health record (PHR).

Here, the medical information system is an information system, which is used in a hospital, such as an electronic medical record system, a receipt computing processing system, an ordering system, a reception (person/qualification recognition) system, or a diagnostic support system. Also, for example, the PHR is a record in which medical information, healthcare information, and health information separated in a medical institution, a medical-checkup institution, a gym, and a house are collected and managed. For example, the PHR is managed in an individual-centric manner by using a management system built on a network.

For example, the analyzing circuitry 1406 acquires information of an object person from the medical information system, the PHR, or the like. Then, the analyzing circuitry 1406 analyzes a position of a landing point of a foot of the object person from a characteristic of the object person during walking which characteristic is included in the acquired information of the object person. For example, in a case where "a stick being used" is acquired as a characteristic of the object person during walking, the analyzing circuitry 1406 detects a stick included in color image information by pattern matching or the like. Then, the analyzing circuitry 1406 acquires a coordinate of an end part, of the detected stick, on a side far from a joint corresponding to a hand of the object person. Then, based on the acquired coordinate of the end part, the analyzing circuitry 1406 determines whether the stick is on a ground or in the air. That is, similarly to the above-described case of a predetermined part of the object person, the analyzing circuitry 1406 determines whether the stick is on the ground or in the air based on a change in the coordinate of the end part. Then, the analyzing circuitry 1406 determines whether a foot of the object person is on the ground based on the determination whether the stick is on the ground. For example, when the stick is on the ground, the analyzing circuitry 1406 determines that a foot on a side of the joint corresponding to the hand holding the stick is on the ground.

Note that the above-described example is just an example and an embodiment is not limited to this. That is, information of the object person is not necessarily acquired from the medical information system or the PHR and there may be a case where the information is input by the operator. Also, the above-described basis of determination (when a stick being on the ground, a foot on a side of a joint corresponding to a hand holding the stick being on the ground) can be set arbitrarily by the operator. That is, a determination basis is set arbitrarily according to an object person executing a walking training.

In the above-described third embodiment, a case where an analysis result is displayed on the output circuitry 110 has been described. However, an embodiment is not limited to this. For example, there may be a case where analysis information is printed on a paper medium.

In the above-described third embodiment, a case of predicting future walking such as that in next walking training has been described. However, an embodiment is not limited to this. For example, there may be a case of predicting a foot print of a next step.

In the above-described third embodiment, a case where a prescribed joint (such as tarsus, ankle, or knee) is used as a coordinate used for calculation of a landing point of a foot has been described. However, an embodiment is not limited to this. For example, there may be a case where a landing point of a foot is calculated by using a coordinate of a position set between predetermined joints.

In the above-described third embodiment, a case of determining landing of a foot by using a value of a coordinate has been described. However, an embodiment is not limited to this. For example, there may be a case where velocity or acceleration of a predetermined part of an object person during execution of walking training is used. In such a case, for example, the analyzing circuitry 1406 determines that a foot is on a ground when velocity or acceleration of a predetermined part of the foot becomes equal to or lower than a predetermined threshold. Or, when velocity or acceleration of a predetermined part of a foot exceeds a predetermined threshold, the analyzing circuitry 1406 determines that an opposite foot of the foot is on the ground.

There may be a case where analysis processing performed by the analyzing circuitry 1406 described in the above-described embodiment is executed according to an operation by an operator or a case where the processing is executed automatically based on a previously-set condition.

In the above-described third embodiment, a case where a landing point of a foot is calculated by analyzing coordinate information of a joint of an object person has been described. However, an embodiment is not limited to this. For example, there may be a case where a landing point of a foot is calculated by using information collected by motion capture a sensor of which is attached to a body of an object person or there may be a case where a landing point of a foot is calculated by a sheet using a pressure sensor.

Fifth Embodiment

Next, a configuration of a motion information processing apparatus 100b according to the fifth embodiment will be described. Based on the configuration described in the first embodiment (configuration illustrated in FIG. 1), the motion information processing apparatus 100b according to the fifth embodiment makes it possible to perform a clinically useful gait analysis with a configuration described in detail in the following. In the following, a case where an object person who performs a walking motion walks from the back of a room to the front thereof will be described as an example. Note that an embodiment is not limited to this. For example, application to a case of walking from the front of the room to the back thereof can be also performed.

Figure 32:
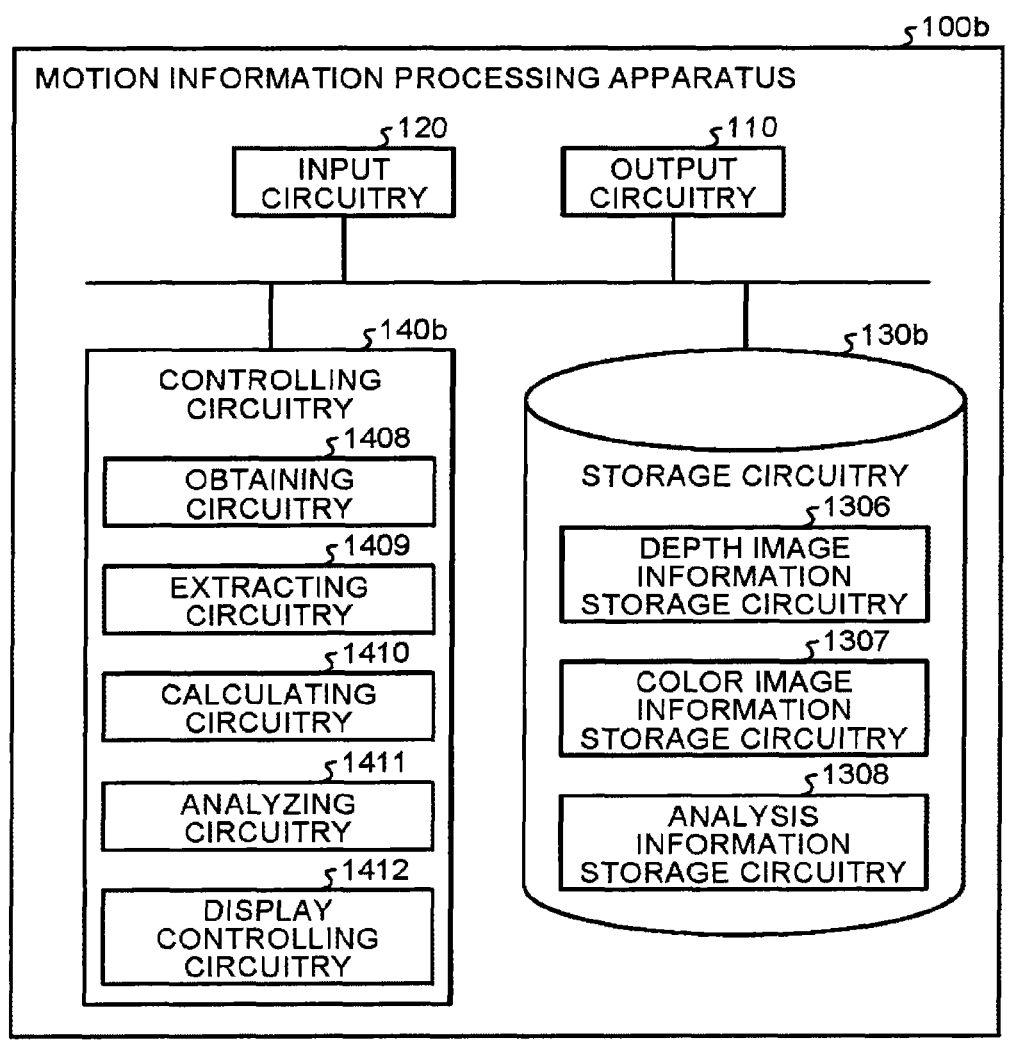
FIG. 32 is a view illustrating an example of a detail configuration of a motion information processing apparatus according to a fifth embodiment.

FIG. 32 is a view illustrating an example of a detail configuration of the motion information processing apparatus 100b according to the fifth embodiment. As illustrated in FIG. 32, in the motion information processing apparatus 100b, storage circuitry 130b includes depth image information storage circuitry 1306, color image information storage circuitry 1307, and analysis information storage circuitry 1308.

The depth image information storage circuitry 1306 stores depth image information generated by motion information collecting circuitry 10. For example, the depth image information storage circuitry 1306 stores, in each frame, depth image information generated by the motion information collecting circuitry 10. Note that as described above, depth image information in one frame is information in which photographing time information, positional information of each pixel included in a photographing range, and a depth of each pixel are associated to each other. Also, as described above, the depth image information is information to which depth information is associated instead of distance information associated to each pixel of distance image information. Each pixel position can be indicated in a distance image coordinate system similar to that of the distance image information. Also, the depth image information is stored into the depth image information storage circuitry 1306 each time being generated by the motion information collecting circuitry 10.

Figure 33:
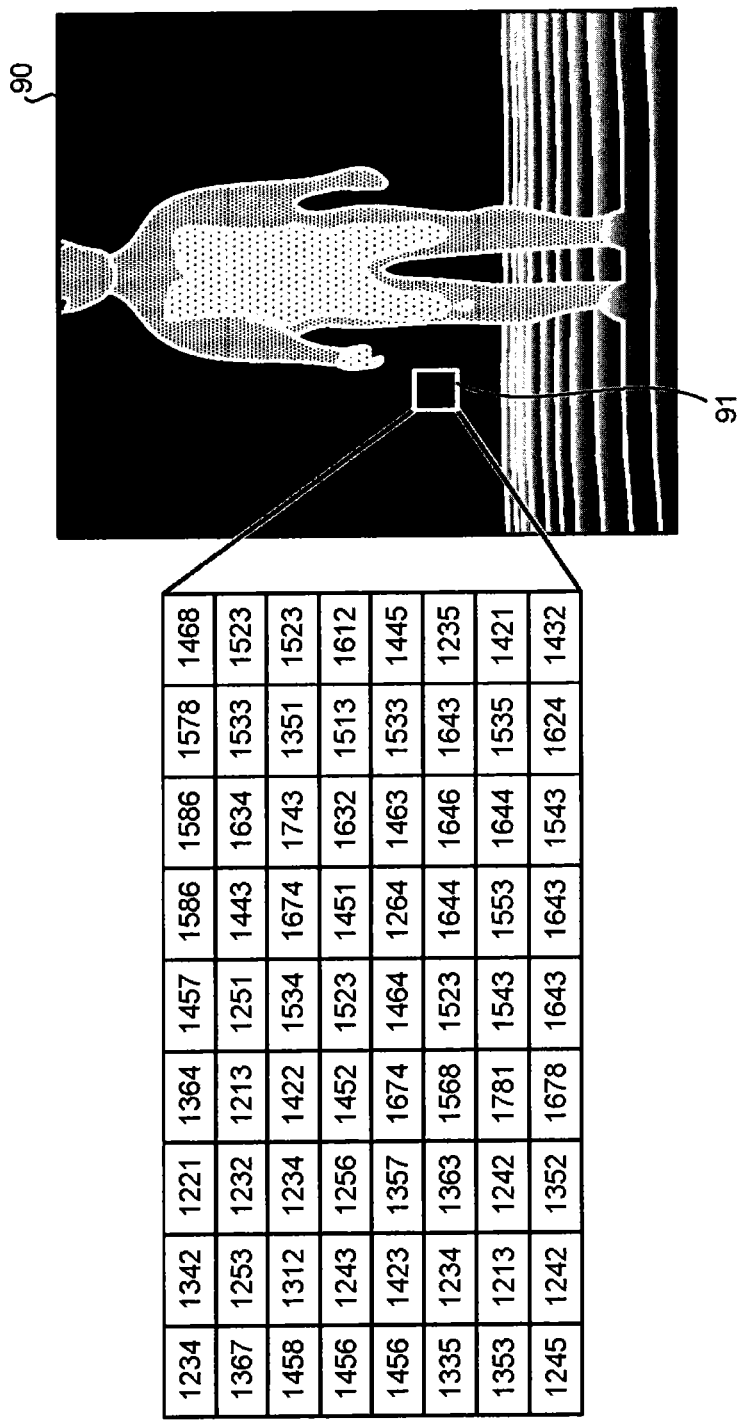
FIG. 33 is a view illustrating an example of information stored in depth image information storage circuitry according to the fifth embodiment.

FIG. 33 is a view illustrating an example of information stored in the depth image information storage circuitry 1306 according to the fifth embodiment. In FIG. 33, a depth image 90 in which gradation of a color corresponding to a depth of each pixel is arranged in a bitmap is illustrated as an example. As illustrated in FIG. 33, in the depth image 90, a depth of each pixel is associated to the pixel. More specifically, for example, in a region 91 in the depth image 90, a depth "1234 mm" is associated to an upper left pixel and a depth "1367 mm" is associated to a pixel under the pixel. That is, the depth image information is three-dimensional information in which a "pixel position X" and a "pixel position Y" in a distance image coordinate system and a "depth z" in a world coordinate system are associated to each other. Also, as described above, the distance image coordinate system and the world coordinate system can be converted mutually. Thus, a three dimensional coordinate in the depth image information can be also indicated in the distance image coordinate system or the world coordinate system.

The color image information storage circuitry 1307 stores color image information collected by the motion information collecting circuitry 10. For example, the color image information is stored into the color image information storage circuitry 1307 each time being generated by the motion information collecting circuitry 10.

Note that in the depth image information storage circuitry 1306 and the color image information storage circuitry 1307, a pixel position of the depth image information and a pixel position of the color image information are previously associated to each other. Also, photographing time information of the depth image information and photographing time information of the color image information are previously associated to each other.

The analysis information storage circuitry 1308 stores an analysis result by controlling circuitry 140b described later. More specifically, the analysis information storage circuitry 1308 stores an analysis result analyzed, by the controlling circuitry 140b described later, by using motion information stored in the storage circuitry 130b. For example, the analysis information storage circuitry 1308 according to the fifth embodiment stores the analysis information illustrated in FIG. 6 described above. Here, a "name number" is an identifier to uniquely identify an object person and is assigned to each name. A "performance date" indicates a date and time on which the object person performs walking training. Also, "analysis information" indicates information of an analysis result analyzed by the controlling circuitry 140b described later.

For example, as illustrated in FIG. 6, the analysis information storage circuitry 1308 stores "a name: A, a name number: 1, a performance date: 20120801_1, and analysis information: a landing point of a foot, an angle, velocity, acceleration, the number of steps, a stride, an overlapped walking distance, a step interval, a walking rate, . . . " The above-described information indicates that analysis information including a "landing point of a foot," an "angle," "velocity," "acceleration," the "number of steps," a "stride," an "overlapped walking distance," a "step interval," and a "walking rate" is stored as information of an analysis result analyzed by using motion information of "first" walking performed on "August 1st" in "2012" by a person with the "name: A" the "name number" of which is "1."

Here, the "landing point of a foot" is information indicating a position, where a foot of an object person touches a ground, and is stored, for example, as coordinate information. Also, the "angle" is information indicating an angle of a body of an object person during walking and information of an angle between a predetermined basis and a part of a body is stored. For example, the analysis information storage circuitry 1308 stores, as the "angle" of the analysis information, information such as an angle of a body in a vertical direction. Note that with respect to the information of the "angle" of the analysis information, a basis and a part of a body are arbitrarily set by an operator. Also, the "velocity" is information indicating velocity of an object person during walking. For example, information of velocity of a predetermined part (such as center of body) is stored. Also, the "acceleration" is information indicating acceleration of an object person during walking. For example, information of acceleration of a predetermined part is stored. Also, the "number of steps" is information indicating the number of steps the object person walks in walking training. Also, the "stride" is information indicating a distance in a traveling direction from a landing point of a right foot (left foot) to a landing point of a left foot (right foot) in walking by an object person. Also, the "overlapped walking distance" is information indicating a distance from landing of one foot to next landing of the foot. Also, the "step interval" is information indicating a distance in a direction orthogonal to a traveling direction from a landing point of a right foot (left foot) to a landing point of a left foot (right foot) in walking by an object person. Also, the "walking rate" is information indicating the number of steps in a unit time.

Similarly, as illustrated in FIG. 6, the analysis information storage circuitry 1308 stores, with respect to a person with "a name: B and a name number: 2," analysis information including a "landing point of a foot," an "angle," "velocity," "acceleration," the "number of steps," a "stride," an "overlapped walking distance," a "step interval," and a "walking rate." In such a manner, the analysis information storage circuitry 1308 stores analysis information, which is motion information of walking collected for each object person and analyzed by the controlling circuitry 140b described later, while associating the analysis information to each object person. Note that the analysis information illustrated in FIG. 6 is just an example. For example, walking time, a period of time in which a foot is on the ground, or the like may be also included. Various kinds of information included in analysis information are arbitrarily changed according to setting performed by an operator with respect to the controlling circuitry 140b described later. For example, there is a case where an item among the pieces of information illustrated in FIG. 6 is not calculated.

In the motion information processing apparatus 100b, the controlling circuitry 140b includes obtaining circuitry 1408, extracting circuitry 1409, calculating circuitry 1410, analyzing circuitry 1411, and display controlling circuitry 1412.

The obtaining circuitry 1408 obtains a frame group which includes depth image information, in which each pixel included in a photographing range and a depth of each pixel are associated to each other, in each frame and which is lined up in time-series. For example, when power of each of the motion information collecting circuitry 10 and the motion information processing apparatus 100b is turned on and each time depth image information in one frame is stored into the depth image information storage circuitry 1306, the obtaining circuitry 1408 obtains the stored depth image information from the depth image information storage circuitry 1306. Also, the obtaining circuitry 1408 obtains, from the color image information storage circuitry 1307, color image information in a frame corresponding to the obtained depth image information. Note that processing in which the obtaining circuitry 1408 obtains depth image information is not limited to the above-described example. For example, a frame group in which frames of photographed depth image information are lined up in time series may be acquired.

Based on depth image information in a frame to be processed and depth image information in a different frame from the depth image information, the extracting circuitry 1409 extracts, from the depth image information in the frame to be processed, an object region which indicates a region of an object to be analyzed and which is in a three-dimensional space.

For example, the extracting circuitry 1409 extracts an object region by one of first extraction processing to extract a moving object, second extraction processing in which depth image information of when there is no person is a basis, and third extraction processing in which depth image information before a predetermined period of time is a basis. In the following, the first to third extraction processing will be described serially.

First Extraction Processing

In the first extraction processing, the extracting circuitry 1409 extracts an object region from depth image information by extracting a moving object. More specifically, the extracting circuitry 1409 calculates, in a frame group, a difference between a depth of each pixel in depth image information in a frame to be processed and that in depth image information in a frame next to the frame in time series. Then, the extracting circuitry 1409 extracts, as an object region, a region of a pixel in which a calculated difference is equal to or larger than a threshold.

Figure 34:
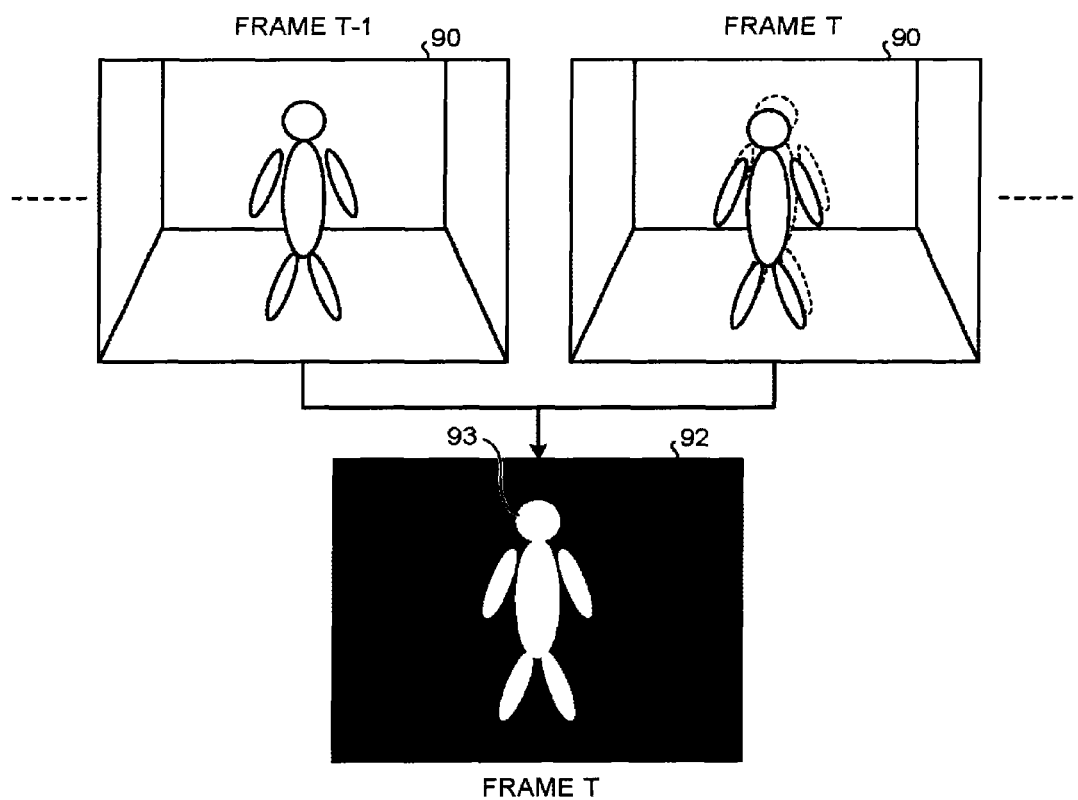
FIG. 34 is a view for describing first extraction processing in which extracting circuitry according to the fifth embodiment extracts an object region.

FIG. 34 is a view for describing first extraction processing in which the extracting circuitry 1409 according to the fifth embodiment extracts an object region. In FIG. 34, a depth image 90 in a frame T−1 and a depth image 90 and a binary image 92 in a frame T are illustrated as examples. In each of the depth image 90 in the frame T and the depth image 90 in the frame T−1, a solid line indicates a position of an object person in each frame. Also, in the depth image 90 in the frame T, a broken line indicates a position of an object person in the frame T−1. That is, the depth image 90 in the frame T indicates that the object person moves from a position of the broken line to a position of the solid line. Note that a "pixel position X" and a "pixel position Y" in the binary image 92 respectively correspond to a "pixel position X" and a "pixel position Y" in a distance image coordinate system. Also, for convenience of description, the broken line indicates a position of the object person in the frame T−1 and a position of the object person in the frame T−1 is not displayed in the depth image 90 in the frame T.

As illustrated in FIG. 34, when the depth image 90 in the frame T is obtained by the obtaining circuitry 1408, the extracting circuitry 1409 subtracts, in each pixel, a depth of the depth image 90 in the frame T−1 from a depth of the depth image 90 in the frame T. Then, the extracting circuitry 1409 generates the binary image 92 in the frame T by performing binarization with a pixel in which the subtracted value is equal to or larger than a threshold in white and a pixel smaller than the threshold in black. In the binary image 92, a region of the black pixel indicates a position of what has a movement smaller than a threshold in a depth direction between the frame T−1 and the frame T. For example, a position of a substance such as a floor, a wall, a desk, or a chair is indicated. Also, a region of the white pixel indicates a position of what has a movement equal to or larger than the threshold in the depth direction between the frame T−1 to the frame T. For example, a position of a photographed person (object) is indicated. That is, the extracting circuitry 1409 extracts an object region 93, which indicates a position of an object person who executes a walking motion, by identifying what has no movement and what has a movement. Note that in FIG. 34, a case of calculating a difference in depth image information between two adjoining frames (frame T and frame T−1) in order to extract what has a movement has been described but this is not a limitation. For example, a difference in depth image information between the frame T and a frame T−t (t is integer number equal to or larger than one) may be calculated. More specifically, for example, the extracting circuitry 1409 may extract what has a movement by subtracting a depth of a depth image 90 in a frame T−2 from a depth of the depth image 90 in the frame T in each pixel with the obtaining circuitry 1408 and performing binarization based on determination whether the subtracted value is equal to or larger than a threshold.

Figure 35:
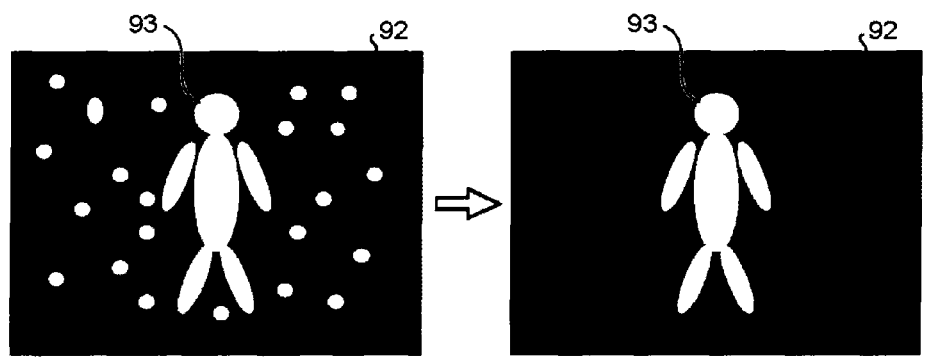
FIG. 35 is a view for describing noise removing processing performed by the extracting circuitry according to the fifth embodiment.

Also, the extracting circuitry 1409 performs noise removing processing to remove a noise from the generated binary image 92. FIG. 35 is a view for describing noise removing processing performed by the extracting circuitry 1409 according to the fifth embodiment. As illustrated in a left view in FIG. 35, there is a case where the binary image 92 generated by the extracting circuitry 1409 includes a region of a white pixel other than the object region 93. This is caused, for example, by a detection error in a distance image collecting circuitry 12. For example, the extracting circuitry 1409 repeatedly executes, with respect to the generated binary image 92, contraction processing to convert a white pixel next to a black pixel into a black pixel and expansion processing to convert a black pixel next to a white pixel into a white pixel for the predetermined number of times. More specifically, the extracting circuitry 1409 executes, with respect to the generated binary image 92, the expansion processing for five times after executing the contraction processing for five times. Accordingly, the extracting circuitry 1409 can keep an original size of a white pixel which does not disappear in five times of the contraction processing and can remove, from the binary image 92, a region of a white pixel which disappears in five times of the contraction processing.

Note that the above-described noise removing processing is just an example and the above-described example is not a limitation. As a different example, the extracting circuitry 1409 may remove a noise by using labeling processing to label coupled pixels with the same number. More specifically, the extracting circuitry 1409 may remove a noise by only leaving white pixels which are labeled with the same number and the number of which is the largest and converting a white pixel with a different number into a black pixel. In addition, this is not a limitation. The extracting circuitry 1409 may remove a noise by different noise removing processing.

In such a manner, each time depth image information is acquired, the extracting circuitry 1409 calculates a difference between a depth of each pixel in depth image information in an acquired frame and that in depth image information in a frame acquired therebefore. Then, the extracting circuitry 1409 generates the binary image 92 based on determination whether the calculated difference is equal to or larger than a threshold. Then, the extracting circuitry 1409 extracts the object region 93 by performing noise removing processing with respect to the generated binary image 92. Note that when a noise in the binary image 92 is equal to or smaller than an acceptable amount, the extracting circuitry 1409 does not necessarily execute noise removing processing.

Second Extraction Processing

In the second extraction processing, the extracting circuitry 1409 extracts an object region from the depth image information by setting, as a basis, depth image information of when there is no person. More specifically, the extracting circuitry 1409 calculates, in a frame group, a difference between a depth of each pixel in depth image information in a frame to be processed and that in depth image information in a frame in which no object is included in a photographing range. Then, the extracting circuitry 1409 extracts, as an object region, a region of a pixel in which a calculated difference is equal to or larger than a threshold.

Figure 36:
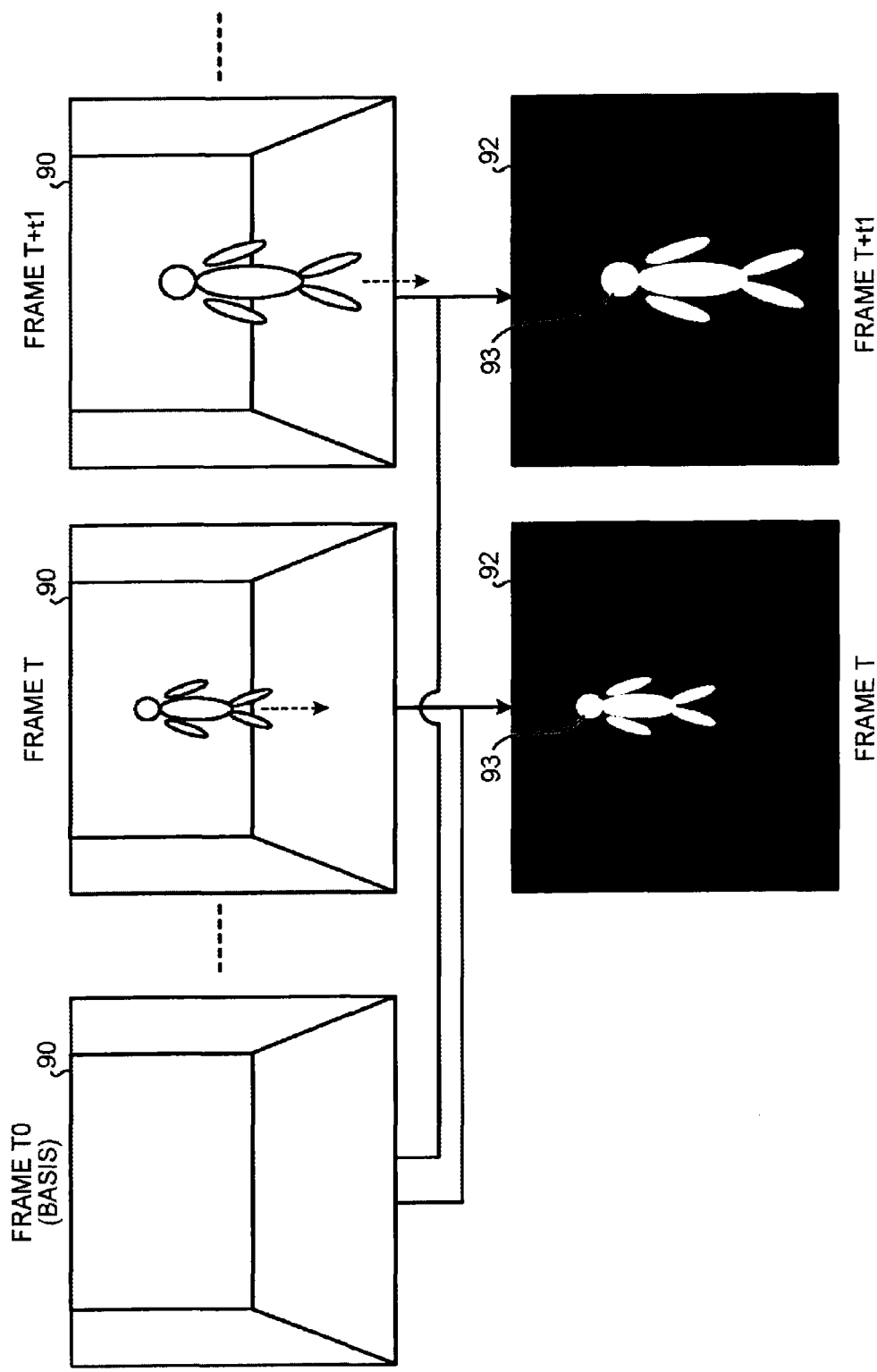
FIG. 36 is a view for describing second extraction processing in which the extracting circuitry according to the fifth embodiment extracts an object region.

FIG. 36 is a view for describing second extraction processing in which the extracting circuitry 1409 according to the fifth embodiment extracts an object region. In FIG. 36, a depth image 90 in a frame TO, the depth image 90 in the frame T, a depth image 90 in a frame T+t1, the binary image 92 in the frame T, and a binary image 92 in the frame T+t1 are illustrated as examples. In FIG. 36, an arrow in a broken line indicates a traveling direction of an object person. Note that in FIG. 36, when there is no person in a photographing range, an operator sets, as a basis, depth image information at the time point.

As illustrated in FIG. 36, the extracting circuitry 1409 previously sets, as a basis, depth image information in the frame TO which information is obtained in a case where no object is included in a photographing range. Then, when the depth image 90 in the frame T is obtained by the obtaining circuitry 1408, the extracting circuitry 1409 subtracts, in each pixel, a depth of the depth image 90 in the frame TO from a depth of the depth image 90 in the frame T. Then, the extracting circuitry 1409 generates the binary image 92 in the frame T by performing binarization with a pixel in which the subtracted value is equal to or larger than a threshold in white and a pixel smaller than the threshold in black. Then, the extracting circuitry 1409 extracts the object region 93 in the frame T by performing noise removing processing with respect to the generated binary image 92. The noise removing processing is similar to the noise removing processing in the above-described first extraction processing, and thus, a description thereof is omitted.

Then, when the depth image 90 in the frame T+t1 is obtained by the obtaining circuitry 1408, the extracting circuitry 1409 subtract, in each pixel, a depth of the depth image 90 in the frame TO from a depth of the depth image 90 in the frame T+t1. Then, the extracting circuitry 1409 generates the binary image 92 in the frame T+t1 by performing binarization with a pixel in which the subtracted value is equal to or larger than a threshold in white and a pixel smaller than the threshold in black. Then, the extracting circuitry 1409 extracts an object region 93 in the frame T+t1 by performing noise removing processing with respect to the generated binary image 92.

In such a manner, each time depth image information is acquired, the extracting circuitry 1409 calculates a difference between a depth of each pixel in depth image information in the acquired frame and that in depth image information in a frame which is a basis. Then, the extracting circuitry 1409 generates the binary image 92 based on determination whether the calculated difference is equal to or larger than a threshold. Then, the extracting circuitry 1409 extracts the object region 93 by performing noise removing processing with respect to the generated binary image 92. Note that when a noise in the binary image 92 is equal to or smaller than an acceptable amount, the extracting circuitry 1409 does not necessarily execute noise removing processing.

Third Extraction Processing

In the third extraction processing, the extracting circuitry 1409 extracts an object region from the depth image information by setting, as a basis, depth image information before a predetermined period of time. More specifically, the extracting circuitry 1409 calculates, in a frame group, a difference between a depth of each pixel in depth image information in a frame to be processed and that in depth image information in a frame before the frame for a predetermined period of time. Then, the extracting circuitry 1409 extracts, as an object region, a region of a pixel in which a calculated difference is equal to or larger than a threshold.

Figure 37:
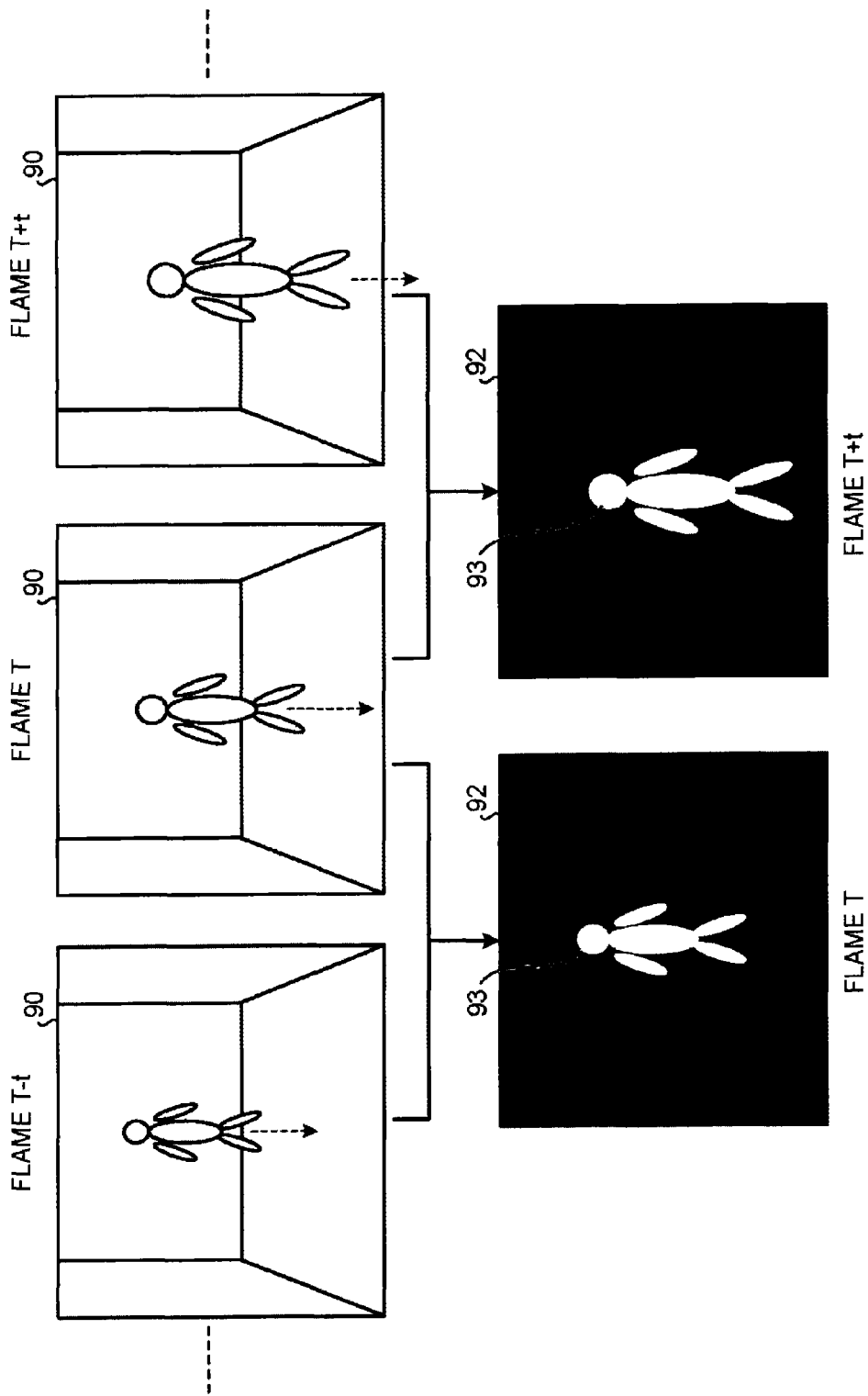
FIG. 37 is a view for describing third extraction processing in which the extracting circuitry according to the fifth embodiment extracts an object region.

FIG. 37 is a view for describing third extraction processing in which the extracting circuitry 1409 according to the fifth embodiment extracts an object region. In FIG. 37, a depth image 90 in the frame T−t, the depth image 90 in the frame T, a depth image 90 in a frame T+t, the binary image 92 in the frame T, and a binary image 92 in the frame T+t are illustrated as examples. In FIG. 37, an arrow in a broken line indicates a traveling direction of an object person.

As illustrated in FIG. 37, when the depth image 90 in the frame T is obtained by the obtaining circuitry 1408, the extracting circuitry 1409 acquires the depth image 90 in the frame T−t acquired before the frame T for t frames (predetermined period of time). Then, the extracting circuitry 1409 subtracts, in each pixel, a depth of the depth image 90 in the frame T−t from a depth of the depth image 90 in the frame T. Then, the extracting circuitry 1409 generates the binary image 92 in the frame T by performing binarization with a pixel in which the subtracted value is equal to or larger than a threshold in white and a pixel smaller than the threshold in black. Then, the extracting circuitry 1409 extracts the object region 93 in the frame T by performing noise removing processing with respect to the generated binary image 92. The noise removing processing is similar to the noise removing processing in the above-described first extraction processing, and thus, a description thereof is omitted.

Then, when the depth image 90 in the frame T+t is obtained by the obtaining circuitry 1408, the extracting circuitry 1409 acquires the depth image 90 in the frame T acquired before the frame T+t for t frames (predetermined period of time). Then, the extracting circuitry 1409 subtracts, in each pixel, a depth of the depth image 90 in the frame T from a depth of the depth image 90 in the frame T+t. Then, the extracting circuitry 1409 generates the binary image 92 in the frame T+t by performing binarization with a pixel in which the subtracted value is equal to or larger than a threshold in white and a pixel smaller than the threshold in black. Then, the extracting circuitry 1409 extracts an object region 93 in the frame T+t by performing noise removing processing with respect to the generated binary image 92.

In such a manner, each time depth image information is acquired, the extracting circuitry 1409 calculates a difference between a depth of each pixel in depth image information in the acquired frame and that in depth image information in a frame before a predetermined period of time. Then, the extracting circuitry 1409 generates the binary image 92 based on determination whether the calculated difference is equal to or larger than a threshold. Then, the extracting circuitry 1409 extracts the object region 93 by performing noise removing processing with respect to the generated binary image 92. Note that here, a case where the number of frames (t frame) is set as a predetermined period of time has been described. However, this is not a limitation and time (such as second) may be set. Also, when a noise in the binary image 92 is equal to or smaller than an acceptable amount, the extracting circuitry 1409 does not necessarily execute noise removing processing.

In such a manner, the extracting circuitry 1409 extracts an object region by any of the first to third extraction processing. Note that, as the motion information processing apparatus 100b, a function of any of the above first to third extraction processing only needs to be included. However, this is not the limitation. For example, functions of all of the first to third extraction processing may be included and selection may be performed arbitrarily each time the object region 93 is extracted.

The calculating circuitry 1410 calculates a position of a foot of an object from the object region. For example, the calculating circuitry 1410 calculates a position of a center of gravity of the object region 93 by using coordinate information in a right/left direction of each pixel included in the object region 93 and coordinate information in an upward/downward direction thereof. Then, the calculating circuitry 1410 calculates, as positions of feet of the object, a position of the lowest point on a right side of the position of the center of gravity in the object region 93 and a position of the lowest point on a left side of the position of the center of gravity in the object region 93.

Figure 38:
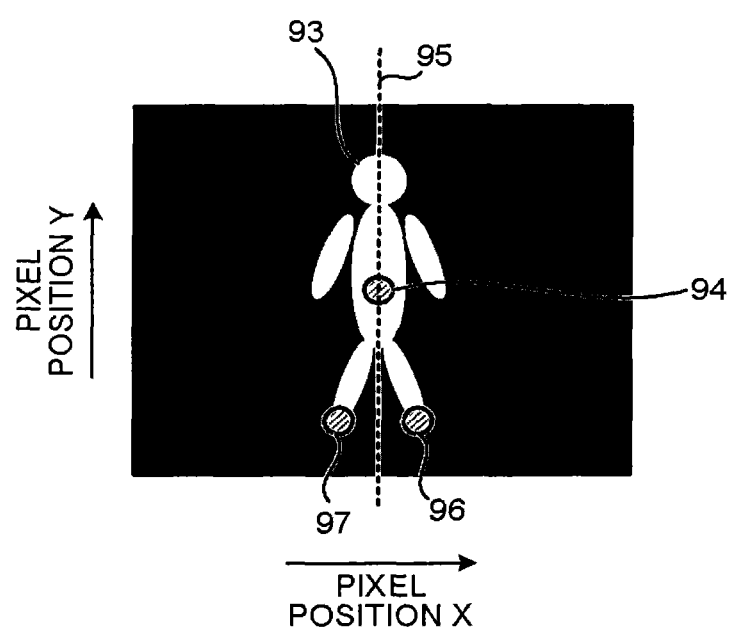
FIG. 38 is a view for describing processing in which calculating circuitry according to the fifth embodiment calculates a position of a foot.

FIG. 38 is a view for describing processing in which calculating circuitry 1410 according to the fifth embodiment calculates a position of a foot. In FIG. 38, a case where the calculating circuitry 1410 calculates a position of a foot by using the object region 93 in the frame T will be described.

As illustrated in FIG. 38, the calculating circuitry 1410 calculates a center of gravity 94 in the object region 93 by using the following equations (1) and (2). Note that in the equations (1) and (2), Xc indicates a value of an X coordinate of the center of gravity 94 and Yc indicates a value of a Y coordinate of the center of gravity 94. Also, X indicates a value of an X coordinate of each pixel included in the binary image 92 and Y indicates a Y coordinate of each pixel included in the binary image 92. Also, f (X, Y) is "1" when a pixel with coordinates (X, Y) is white and f (X, Y) is "0" when the pixel is black.

$$Xc = \Sigma X \times f(X, Y) / \text{sum}(f(X, Y)) \tag{1}$$

$$Yc = \Sigma Y \times f(X, Y) / \text{sum}(f(X, Y)) \tag{2}$$

Then, the calculating circuitry 1410 calculates a perpendicular 95 which passes through the calculated center of gravity 94 (Xc, Yc). Then, the calculating circuitry 1410 calculates, as a position of a left foot, a lowest point 96 in the object region 93 in a region in which the pixel position X is larger than the perpendicular 95. Also, the calculating circuitry 1410 calculates, as a position of a right foot, a lowest point 97 in the object region 93 in the region in which the pixel position X is smaller than the perpendicular 95. Here, a position of each foot calculated from the binary image 92 in the frame T is two-dimensional information to which the pixel position X and the pixel position Y are associated. Thus, the calculating circuitry 1410 acquires a position of a foot (x, y, z) in a world coordinate system from the depth image 90 in the frame corresponding to the binary image 92.

The analyzing circuitry 1411 analyzes a walking state based on a temporal change in a position of a foot. For example, the analyzing circuitry 1411 analyzes a position where a foot of the object touches a ground. Also, by using the information calculated by the calculating circuitry 1410, the analyzing circuitry 1411 calculates analysis information in which a walking state such as an angle of posture, velocity, acceleration, or a distance of the object person is analyzed and stores the calculated analysis information into the analysis information storage circuitry 1308.

Here, in a case of calculating a landing point of a foot of the object person, for example, an operator such as a doctor or a physical therapist first inputs an instruction request of analysis through input circuitry 120. Here, by inputting a name or a name number of the object person, a performance date, and the like, the operator makes the obtaining circuitry 1408 obtain intended depth image information and makes the extracting circuitry 1409 and the calculating circuitry 1410 execute processing. Note that in a case where analysis is executed along with walking training in real time, it is possible to perform setting in such a manner that motion information is obtained automatically without reception of an operation from the operator. For example, by using a position of a foot which position is calculated by the calculating circuitry 1410, the analyzing circuitry 1411 calculates a landing point where the foot of the object person touches the ground.

Here, the analyzing circuitry 1411 according to the fifth embodiment analyzes a landing point of a foot as illustrated in FIG. 25A to FIG. 25F described above. For example, the analyzing circuitry 1411 acquires, from all frames, positions (coordinate) of the right foot and the left foot and creates a graph with a vertical axis as a z coordinate and a horizontal axis as time as illustrated in FIG. 25A.

That is, as illustrated in FIG. 25A, the analyzing circuitry 1411 calculates a curved line 71 indicating a temporal change in the z coordinate of the left foot and a curved line 72 indicating a temporal change in the z coordinate of the right foot. Then, for example, the analyzing circuitry 1411 determines that a time point at which a change in a value of the z coordinate in a unit time in each curved line is equal to or smaller than a predetermined threshold is a time point at which a foot touches a ground.

For example, as illustrated in FIG. 25A, the analyzing circuitry 1411 determines that a time point 81 at which a change in a coordinate in a unit time becomes equal to or smaller than a predetermined threshold in the curved line 71 indicating a temporal change in the z coordinate of the left foot is a time point at which the left foot touches the ground. Similarly, as illustrated in FIG. 25A, the analyzing circuitry 1411 determines that a time point 82 at which a change in a coordinate in a unit time in the curved line 72 indicating a temporal change in the z coordinate of the right foot becomes equal to or smaller than a predetermined threshold is a time point at which the right foot touches the ground. The analyzing circuitry 1411 stores photographing time information in a frame corresponding to a time point at which it is determined that a foot touches the ground and a position of the foot (x, y, z) into the analysis information storage circuitry 1308.

Also, in the above-described example, a case of determining that a time point at which a change in a z coordinate of a foot in a unit time is equal to or smaller than a predetermined threshold is a time point at which the foot touches a ground has been described. However, an embodiment is not limited to this. For example, there may be a case of determining that a time point at which a change in a z coordinate of a foot in a unit time is equal to or larger than a predetermined threshold is a time point at which an opposite foot of the foot touches the ground. For example, as illustrated in FIG. 25A, the analyzing circuitry 1411 determines that a time point at which a change in a unit time is equal to or larger than a predetermined threshold in the curved line 71 indicating a temporal change in the z coordinate of the left foot is a time point at which the right foot touches the ground. Similarly, as illustrated in FIG. 25A, the analyzing circuitry 1411 determines that a time point at which a change in a unit time is equal to or larger than a predetermined threshold in the curved line 72 indicating a temporal change in the z coordinate of the right foot is a time point at which the left foot touches the ground.

Next, a case of determining a landing point of a foot by using a y coordinate will be described. For example, the analyzing circuitry 1411 acquires, from all frames, positions (coordinate) of the right foot and the left foot and creates a graph with a vertical axis as a y coordinate and a horizontal axis as time as illustrated in FIG. 25B.

That is, as illustrated in FIG. 25B, the analyzing circuitry 1411 calculates a curved line 73 indicating a temporal change in a y coordinate of the left foot and a curved line 74 indicating a temporal change in a y coordinate of the right foot. Then, for example, the analyzing circuitry 1411 determines that a time point at which a value of the y coordinate in each curved line becomes a predetermined value (such as "y=0") is a time point at which a foot touches the ground.

For example, as illustrated in FIG. 25B, the analyzing circuitry 1411 analyzes that a time point 83 at which a value of a y coordinate becomes the predetermined value (such as "y=0") in the curved line 73 indicating a temporal change in the y coordinate of the left foot is a time point at which the left foot touches the ground. Similarly, as illustrated in FIG. 25B, the analyzing circuitry 1411 determines that a time point 84 at which a value of a y coordinate becomes the predetermined value (such as "y=0") in the curved line 74 indicating a temporal change in the y coordinate of the right foot is a time point at which the right foot touches the ground. The analyzing circuitry 1411 stores photographing time information in a frame corresponding to a time point at which it is determined that a foot touches the ground and a position of the foot (x, y, z) into the analysis information storage circuitry 1308.

Also, in the above-described example, a case of determining that a time point at which a change in a y coordinate of a foot in a unit time is equal to or smaller than a predetermined threshold is a time point at which the foot touches a ground has been described. However, an embodiment is not limited to this. For example, there may be a case of determining that a time point at which a change in a y coordinate of a foot in a unit time is equal to or larger than a predetermined threshold is a time point at which an opposite foot of the foot touches the ground. That is, the analyzing circuitry 1411 determines whether a foot is in the air and determines that the other foot is on the ground when one foot is in the air. For example, when a description is made with FIG. 25B as an example, the analyzing circuitry 1411 determines that a time point at which a value of a y coordinate becomes a predetermined value (such as "y>b") in the curved line 73 indicating a temporal change in the y coordinate of the left foot is a time point at which the right foot touches the ground. Similarly, the analyzing circuitry 1411 determines that a time point at which a value of a y coordinate becomes the predetermined value (such as "y>b") in the curved line 74 indicating a temporal change in the y coordinate of the right foot is a time point at which the left foot touches the ground.

Next, a case of determining a landing point of a foot by using an x coordinate will be described. For example, the analyzing circuitry 1411 acquires, from all frames, positions (coordinate) of the right foot and the left foot and creates a graph with a vertical axis as an x coordinate and a horizontal axis as time as illustrated in FIG. 25C.

That is, as illustrated in FIG. 25C, the analyzing circuitry 1411 calculates a curved line 77 indicating a temporal change in the x coordinate of the left foot and a curved line 78 indicating a temporal change in the x coordinate of the right foot. Then, for example, the analyzing circuitry 1411 determines that a time point at which a value of the x coordinate in each curved line becomes constant is a time point at which the foot is on the ground.

For example, as illustrated in FIG. 25C, the analyzing circuitry 1411 determines that a time point 87 at which a value of an x coordinate becomes constant in the curved line 77 indicating a temporal change in the x coordinate of the left foot is a time point at which the left foot touches the ground. Similarly, as illustrated in FIG. 25C, the analyzing circuitry 1411 determines that a time point 88 at which a value of an x coordinate becomes constant in the curved line 78 indicating a temporal change in the x coordinate of the right foot is a time point at which the right foot touches the ground. The analyzing circuitry 1411 stores photographing time information in a frame corresponding to a time point at which it is determined that a foot touches the ground and a position of the foot (x, y, z) into the analysis information storage circuitry 1308.

Also, in the above-described example, a case of determining that a time point at which a value of an x coordinate of a foot becomes constant is a time point at which the foot touches the ground has been described. However, an embodiment is not limited to this. For example, there may be a case of determining that a time point at which a value of an x coordinate of a foot changes little by little is a time point at which an opposite foot of the foot touches the ground. That is, the analyzing circuitry 1411 determines whether a foot is in the air and determines that the other foot is on the ground when one foot is in the air. For example, when a description is made with FIG. 25C as an example, the analyzing circuitry 1411 determines that a time point at which a value of a x coordinate changes little by little in the curved line 77 indicating a temporal change in the x coordinate of the left foot is a time point at which the right foot touches the ground. Similarly, the analyzing circuitry 1411 determines that a time point at which a value of an x coordinate changes little by little in the curved line 78 indicating a temporal change in the x coordinate of the right foot is a time point at which the left foot touches the ground.

In the above-described example, a case of determining landing of a foot in normal walking has been described. In the following, a case of determining irregular landing of a foot will be described. When walking training in rehab is executed, for example, there is a case where irregular landing of a foot is caused due to tripping. In the following, determination of irregular landing of a foot by using a value of each of a z coordinate, a y coordinate, and an x coordinate will be described serially.

First, a case of determining an irregular landing point of a foot by using a z coordinate will be described. Here, FIG. 25D is a graph similar to FIG. 25A. For example, as illustrated in FIG. 25D, the analyzing circuitry 1411 determines that a time point in a region R1 in which values of the z coordinate in the curved line 71 indicating a temporal change in the z coordinate of the left foot and the curved line 72 indicating a temporal change in the z coordinate of the right foot are similar values and there is no change in the values for a certain period of time is a time point at which irregular landing of a foot is caused. Also, for example, the analyzing circuitry 1411 can determine that a time point at which a value of the z coordinate goes back is a time point at which irregular landing of a foot is caused.

Next, a case of determining an irregular landing point of a foot by using a y coordinate will be described. Here, FIG. 25E is a graph similar to FIG. 25B. For example, as illustrated in FIG. 25E, the analyzing circuitry 1411 determines that a time point in a region R2, in which a value of the y coordinate becomes "y=0" in each of the curved line 73 indicating a temporal change in the y coordinate of the left foot and the curved line 74 indicating a temporal change in the y coordinate of the right foot, is a time point at which irregular landing of a foot is caused.

Next, a case of determining an irregular landing point of a foot by using an x coordinate will be described. Here, FIG. 25F is a graph similar to FIG. 25C. For example, as illustrated in FIG. 25F, the analyzing circuitry 1411 determines that a time point 89 in a region R3 in which a value of the x coordinate changes for a degree exceeding a predetermined threshold in the curved line 77 indicating a temporal change in the x coordinate of the left foot is a time point at which the left foot touches the ground.

As described above, the analyzing circuitry 1411 can determine an irregular landing point of a foot by using a value of the z coordinate, the y coordinate, or the x coordinate. Thus, for example, the analyzing circuitry 1411 can analyze a landing point of a foot of when a balance is lost during walking training and tripping is performed.

In the above-described example, a case of determining a landing point of a foot by using a single coordinate has been described. However, an embodiment is not limited to this. For example, there may be a case where determination is made by using a plurality of coordinates in a comprehensive manner with respect to each coordinate. For example, there may be a case where a change in the z coordinate and a change in the y coordinate are analyzed and it is determined whether a foot touches the ground based on analysis results. Also, there may be a case where a predetermined coefficient is added to a value of each coordinate. For example, there may be a case where determination is made after a coefficient "α" is added to a value of the y coordinate.

Also, as described above, in addition to determination of landing of a foot, the analyzing circuitry 1411 can make determination that a foot is in the air. That is, for example, when a right foot is in the air during walking, the analyzing circuitry 1411 can determine that a left foot is on the ground. Also, by previously inputting coordinates of the ground into a system, the analyzing circuitry 1411 can determine that a foot is on the ground when the foot becomes close to the coordinates of the ground.

As described above, the analyzing circuitry 1411 analyzes a position (coordinate) of a landing point of a foot. Accordingly, for example, the analyzing circuitry 1411 analyzes an overlapped walking distance, a stride, a step interval, the number of steps, a walking rate, walking time, a period of time in which a foot is on the ground, or the like based on the analyzed position of the landing point. That is, the analyzing circuitry 1411 analyzes the above-described various kinds of information by using coordinates of the landing point. Here, the analyzing circuitry 1411 can calculate an overlapped walking distance, a stride, a step interval, or the like with a walking direction as a basis.

Note that in FIG. 25A to FIG. 25F described above, a case where the object person walks in a depth direction (z-axis direction) (case of walking along z-axis toward motion information collecting circuitry 10) has been described as an example. However, an embodiment is not limited to this. For example, there may be a case where walking is performed in such a manner that the analyzing circuitry 1411 becomes away from the motion information collecting circuitry 10 along the z-axis. In this case, the lowest point 96 calculated by the calculating circuitry 1410 indicates a position of a right foot of the object person and the lowest point 97 indicates a position of a left foot of the object person.

Here, a case of analyzing velocity will be described. When analyzing velocity, the analyzing circuitry 1411 calculates a moving distance [m] of a coordinate corresponding to a predetermined part of the object person in each predetermined period of time (such as 0.5 second). Then, based on the calculated moving distance in a predetermined period of time, the analyzing circuitry 1411 calculates moving velocity [m/second] of the object person in the predetermined period of time. Here, the analyzing circuitry 1411 can also calculate, as velocity of walking of the object person, an average value of moving velocity of the object person during walking training. For example, the analyzing circuitry 1411 calculates moving velocity of a part (such as highest point in object region 93 or center of gravity in object region 93) instructed by the operator through the input circuitry 120.

Also, the analyzing circuitry 1411 calculates acceleration by using the calculated velocity. More specifically, the analyzing circuitry 1411 calculates acceleration (change rate of velocity in unit time) by using the velocity in the unit time which velocity is calculated by the above-described method.

Also, a case of analyzing a distance will be described. The analyzing circuitry 1411 measures a distance or the like between predetermined parts of the object person which distance is collected by the motion information collecting circuitry 10. For example, the analyzing circuitry 1411 measures a stride, a step interval, a distance between joints, or the like of the object person.

For example, the analyzing circuitry 1411 calculates a distance of a stride or a step interval. For example, when information of a foot print and a track of a body is displayed on the output circuitry 110 and an operator inputs a measurement request of each distance through the input circuitry 120, the analyzing circuitry 1411 calculates a stride based on a value of a z coordinate in coordinate information corresponding to a first step and a value of a z coordinate in coordinate information corresponding to a second step. Similarly, the analyzing circuitry 1411 calculates a step interval based on a value of an x coordinate in the coordinate information corresponding to the first step and a value of an x coordinate in the coordinate information corresponding to the second step.

Note that the above-described example is just an example and it is possible to arbitrarily execute measurement of a distance. For example, with a measurement function of the analyzing circuitry 1411, it is possible to calculate a distance from a foot print of a first step to a foot print of a second step based on values of an x coordinate and a z coordinate in coordinate information corresponding to the first step and values of an x coordinate and a z coordinate in coordinate information corresponding to the second step. Also, the analyzing circuitry 1411 can calculate a distance of movement of an x coordinate between predetermined frames by acquiring a value of an x coordinate in each frame of the same part (such as highest point corresponding to head in object region 93) of an object person. Note that frames in such a case can be set arbitrarily. For example, it is also possible to perform calculation between a frame of a time point at which a right foot touches the ground and a frame of a time point at which a left foot touches the ground.

Also, in measurement processing performed by the analyzing circuitry 1411, it is also possible to measure time information. For example, the analyzing circuitry 1411 can measure a period of time between a first step and a second step in walking by the object person, a period of time of landing in each step, a period of time spent for single walking training, or the like. Also, the analyzing circuitry 1411 can measure a walking rate (number of steps in unit time) or the like by using the measured time. In the above, an example of measurement processing performed by the analyzing circuitry 1411 has been described. Here, the above-described measurement processing performed by the analyzing circuitry 1411 can be performed according to an instruction from the operator or can be performed automatically.

As described above, by using the object region 93 in each frame of the object person which region is calculated by the calculating circuitry 1410, the analyzing circuitry 1411 executes various kinds of analyses related to walking by the object person. Then, the analyzing circuitry 1411 stores the above-described analysis result into the analysis information storage circuitry 1308.

Figure 39:
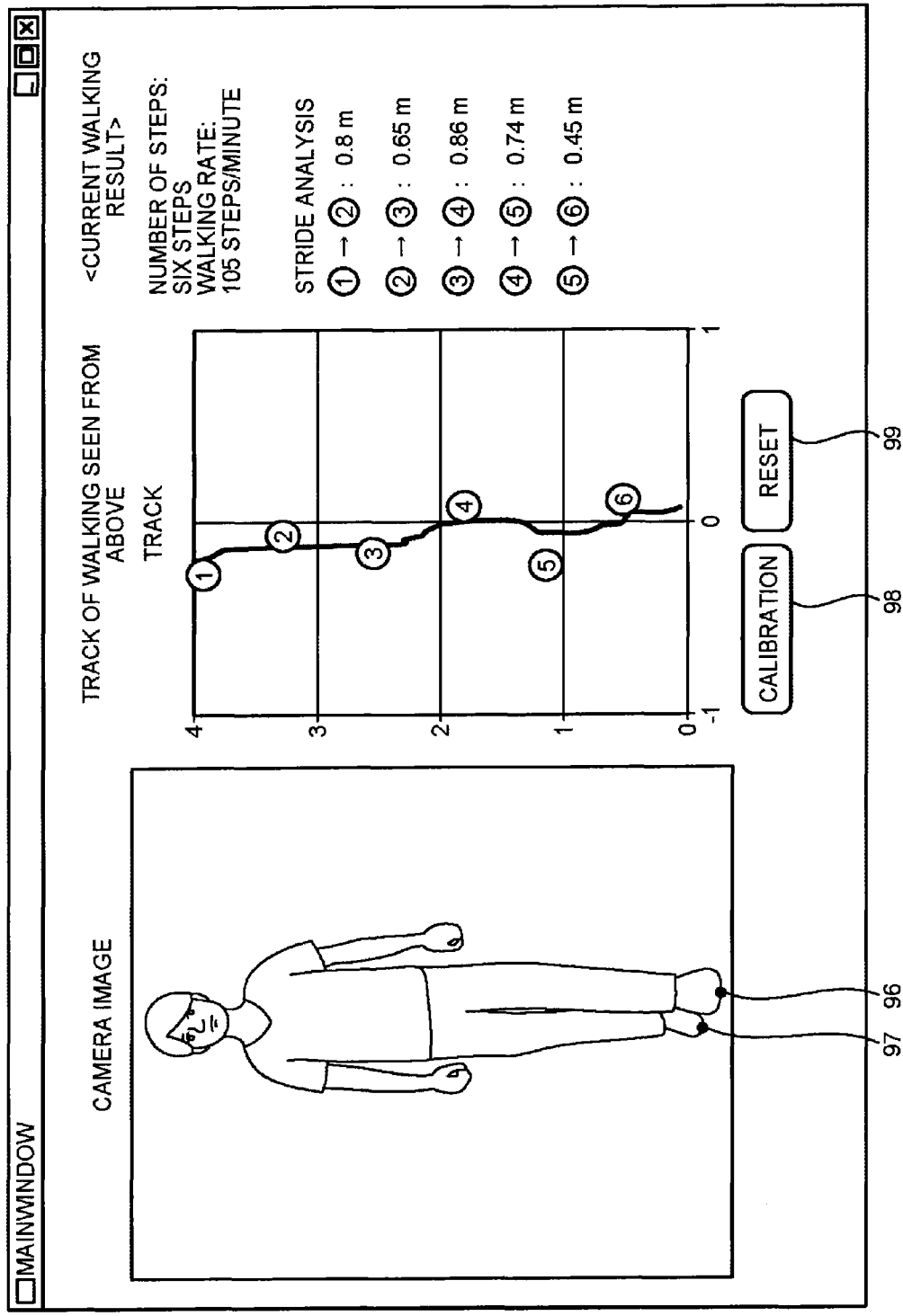
FIG. 39 is a view illustrating an example of an analysis result displayed by control performed by display controlling circuitry according to the fifth embodiment.

Referring back to FIG. 32, the display controlling circuitry 1412 performs control in such a manner that walking information analyzed by the analyzing circuitry 1411 is displayed on the output circuitry 110. More specifically, the display controlling circuitry 1412 performs control in such a manner that analysis information stored in the analysis information storage circuitry 1308 is displayed on the output circuitry 110. In the following, with reference to FIG. 39, an example of an analysis result displayed according to control by the display controlling circuitry 1412 will be described. FIG. 39 is a view illustrating an example of an analysis result displayed by control performed by the display controlling circuitry 1412 according to the fifth embodiment.

As illustrated in FIG. 39, the display controlling circuitry 1412 displays, on the output circuitry 110, analysis information in which a camera image (color image) is arranged in a left-side region in a "MainWindow." More specifically, the display controlling circuitry 1412 displays an image in which positions of feet (lowest point 96 and lowest point 97) calculated from a depth image 90 in a corresponding frame is superimposed on color image information obtained by the obtaining circuitry 1408.

Also, the display controlling circuitry 1412 displays, on the output circuitry 110, analysis information in which a "track of walking seen from the above" is arranged in a center region in the "MainWindow." Here, the "track of walking seen from the above" is an example of information indicating a landing point of a foot and a track of a body of the object person which information is analyzed by the analyzing circuitry 1411. Accordingly, the operator can further see information of a foot print and a track of a body from the above, which information cannot be seen in a camera image displayed two-dimensionally, and can evaluate an analysis result of a stride analysis or the like.

Also, the display controlling circuitry 1412 displays, on the output circuitry 110, analysis information in which a <current walking result> is arranged on a right-side region in the "MainWindow." More specifically, the display controlling circuitry 1412 displays, as the <current walking result>, the "number of steps: six steps," a "walking rate: 105 steps/minute," and a "stride analysis" which is an analysis result of a stride between steps. Accordingly, the operator can evaluate a walking condition of the object person at a glance.

Also, the display controlling circuitry 1412 displays a button 98 and a button 99. Here, the button 98 is a button for setting, as a basis, depth image information of when there is no person in the above-described second extraction processing. That is, by clicking the button 98 in a case where there is no person in a photographing range, the operator sets depth image information at the time point as a basis. Also, the button 99 is a button to reset a basis in the above-described third extraction processing. That is, when walking training is repeatedly executed, the operator resets a basis by clicking the button 99 in the beginning of the walking training in order to prevent depth image information in previously-performed walking training from being used as a basis of analysis in current walking training.

Note that the display controlling circuitry 1412 can output, from the output circuitry 110, not only the above-described information but also various different kinds of information by using information analyzed by the analyzing circuitry 1411. For example, by using the analysis information analyzed by the analyzing circuitry 1411, the display controlling circuitry 1412 can generate track information, superimposed image information, or the like described in the first and second embodiments and can output the generated information from the output circuitry 110. Here, also in the motion information processing apparatus 100b according to the fifth embodiment, there may be a case where a generating circuitry 1403 illustrated in FIG. 4 is included and the generating circuitry 1403 generates display information by using analysis information analyzed by the analyzing circuitry 1411.

Figure 40:
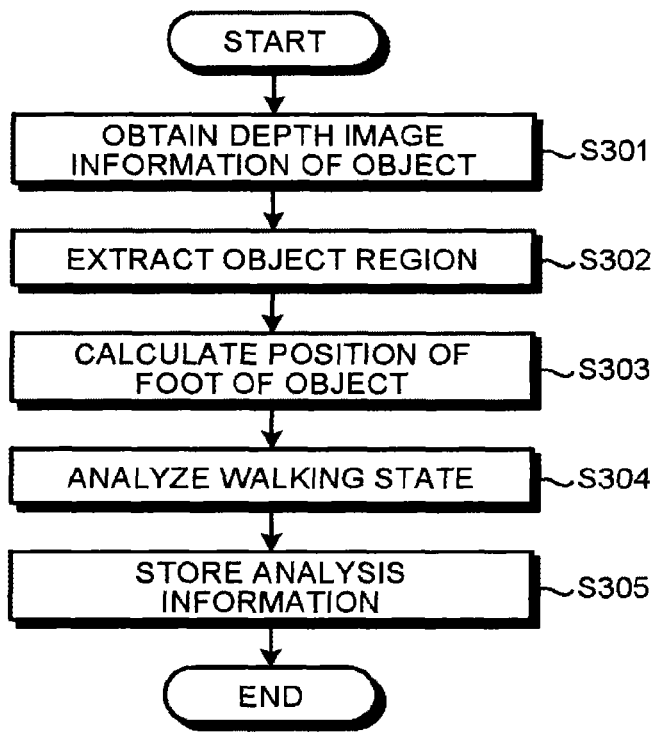
FIG. 40 is a flowchart for describing an example of a procedure of processing performed by the motion information processing apparatus according to the fifth embodiment.
Figure 41:
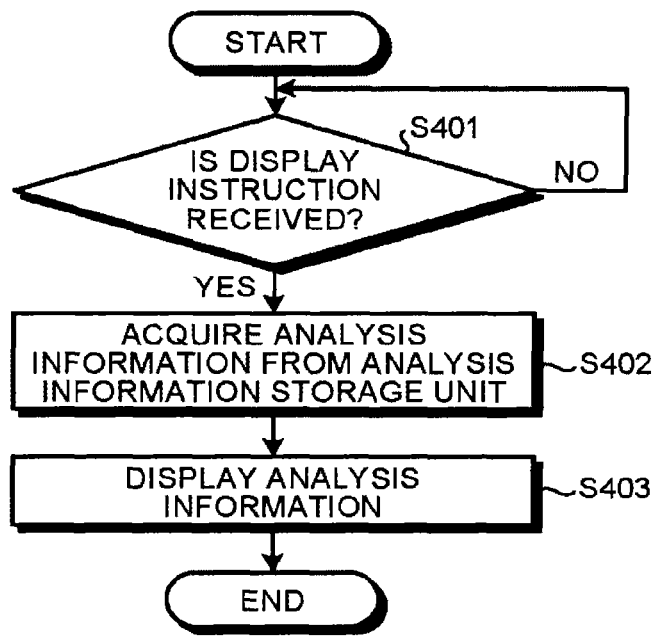
FIG. 41 is a flowchart for describing an example of a procedure of processing performed by the motion information processing apparatus according to the fifth embodiment.

Next, with reference to FIG. 40 and FIG. 41, a processing procedure in the motion information processing apparatus 100b according to the fifth embodiment will be described. Each of FIG. 40 and FIG. 41 is a flowchart for describing an example of a procedure of processing performed by the motion information processing apparatus 100b according to the fifth embodiment. Note that in FIG. 40, processing in which the motion information processing apparatus 100b analyzes a walking state is illustrated and in FIG. 41, processing in which the motion information processing apparatus 100b displays analysis information is illustrated.

First, with reference to FIG. 40, the processing in which the motion information processing apparatus 100b analyzes a walking state will be described. As illustrated in FIG. 40, the obtaining circuitry 1408 obtains depth image information of an object (step S301). For example, when power of each of the motion information collecting circuitry 10 and the motion information processing apparatus 100b is turned on and each time depth image information in one frame is stored into the depth image information storage circuitry 1306, the obtaining circuitry 1408 obtains the stored depth image information from the depth image information storage circuitry 1306.

Then, the extracting circuitry 1409 extracts the object region 93 (step S302). For example, based on depth image information to be processed and depth image information in a different frame from the depth image information, the extracting circuitry 1409 extracts the object region 93 from the depth image information to be processed. More specifically, the extracting circuitry 1409 extracts an object region by one of the above-described first to third extraction processing.

Then, the calculating circuitry 1410 calculates a position of a foot of the object (step S303). For example, the calculating circuitry 1410 calculates a position of a center of gravity in the object region 93 extracted by the extracting circuitry 1409. Then, the calculating circuitry 1410 calculates, as positions of feet of the object, a position of the lowest point on a right side of the position of the center of gravity in the object region 93 and a position of the lowest point on a left side of the position of the center of gravity in the object region 93.

Next, the analyzing circuitry 1411 analyzes a walking state (step S304). For example, the analyzing circuitry 1411 analyzes a position where a foot of the object touches a ground based on a temporal change in a position of the foot calculated by the calculating circuitry 1410. Also, the analyzing circuitry 1411 analyzes an angle of posture, velocity, acceleration, a distance, and the like of the object person. Then, the analyzing circuitry 1411 stores the analyzed analysis information into the analysis information storage circuitry 1308 (step S305).

Next, with reference to FIG. 41, processing in which the motion information processing apparatus 100b displays analysis information will be described. As illustrated in FIG. 41, when receiving a display instruction to display analysis information from the operator (yes in step S401), the display controlling circuitry 1412 acquires analysis information from the analysis information storage circuitry 1308 according to the received display instruction (step S402). Note that the display controlling circuitry 1412 is in a standby state until the display instruction is received (no in step S401).

Then, the display controlling circuitry 1412 displays the analysis information (step S403). For example, the display controlling circuitry 1412 displays, on the output circuitry 110, analysis information in which a camera image (color image) is arranged in a left-side region in the "MainWindow," a "track of walking seen from the above" is arranged in a center region thereof, and a <current walking result> is arranged in a right side-region thereof.

As described above, the motion information processing apparatus 100b according to the fifth embodiment acquires depth image information in time series. Then, based on depth image information to be processed and depth image information in a different frame from the depth image information, the motion information processing apparatus 100b extracts an object region from the depth image information to be processed. The motion information processing apparatus 100b calculates a position of a foot of the object from the object region. Then, the motion information processing apparatus 100b analyzes a walking state of the object based on a temporal change in a position of the foot of the object. Thus, the motion information processing apparatus 100b can perform a clinically useful gait analysis.

For example, in walking training, the object person repeatedly walks for a distance around 10 meters. Thus, clinically, it is required to analyze walking at least for a distance in this degree. Since the motion information processing apparatus 100b according to the fifth embodiment analyzes walking at least in this degree by the above-described processing, a clinically useful gait analysis can be performed. Note that a distance which can be analyzed by the motion information processing apparatus 100b is not limited to 10 meters. A gait analysis for a longer distance can be performed according to performance of a sensor to collect depth image information.

Also, according to the fifth embodiment, the analyzing circuitry 1411 determines whether a foot of the object person is on the ground based on a temporal and three-dimensional change in a position of the foot of the object person. When it is determined that the foot is on the ground, a position of the foot of the object person at a time point of the determination is set as a landing point. Thus, the motion information processing apparatus 100b according to the fifth embodiment can analyze a position of a landing point of a foot based on a movement of each of various parts of the object person during walking and can extract landing of the foot accurately.

Also, according to the fifth embodiment, each time depth image information is acquired, the extracting circuitry 1409 calculates a difference between a depth of each pixel in depth image information in an acquired frame and that in depth image information in a frame acquired therebefore. Then, the extracting circuitry 1409 extracts, as an object region, a region of a pixel in which a calculated difference is equal to or larger than a threshold. Thus, the motion information processing apparatus 100b according to the fifth embodiment can accurately extract an object moving in a photographing range.

Also, according to the fifth embodiment, each time depth image information is acquired, the extracting circuitry 1409 calculates a difference between a depth of each pixel in depth image information in an acquired frame and that in depth image information in a frame acquired in a case where no object is included in a photographing range. Then, the extracting circuitry 1409 extracts, as an object region, a region of a pixel in which a calculated difference is equal to or larger than a threshold. Thus, the motion information processing apparatus 100b according to the fifth embodiment can accurately extract an object from the depth image information.

Also, according to the fifth embodiment, each time depth image information is acquired, the extracting circuitry 1409 calculates a difference between a depth of each pixel in depth image information in an acquired frame and that in depth image information in a frame acquired before the acquired frame for a predetermined period of time. Then, the extracting circuitry 1409 extracts, as an object region, a region of a pixel in which a calculated difference is equal to or larger than a threshold. Thus, the motion information processing apparatus 100b according to the fifth embodiment can accurately extract an object which moves in a predetermined period of time.

Sixth Embodiment

In the fifth embodiment, a case where a walking state is analyzed by using depth image information in which one object person is photographed has been described. However, there is a case where a helper to help an object person or a different person performing rehab is included in depth image information in addition to the object person. Thus, in the sixth embodiment, a case where a motion information processing apparatus 100b analyzes a walking state of the object person by using depth image information in which a plurality of people is photographed.

The motion information processing apparatus 100b according to the sixth embodiment includes a configuration similar to that of the motion information processing apparatus 100b illustrated in FIG. 32 and a part of processing in an extracting circuitry 1409 is different therefrom. Thus, in the sixth embodiment, a point different from the fifth embodiment will be mainly described. To a point including a function similar to the configuration described in the fifth embodiment, a reference sign identical to that in FIG. 32 is assigned and a description thereof is omitted.

The extracting circuitry 1409 according to the sixth embodiment receives a designation operation to designate a predetermined region in depth image information. Then, the extracting circuitry 1409 extracts an object region 93 from depth image information included in the received predetermined region.

Figure 42:
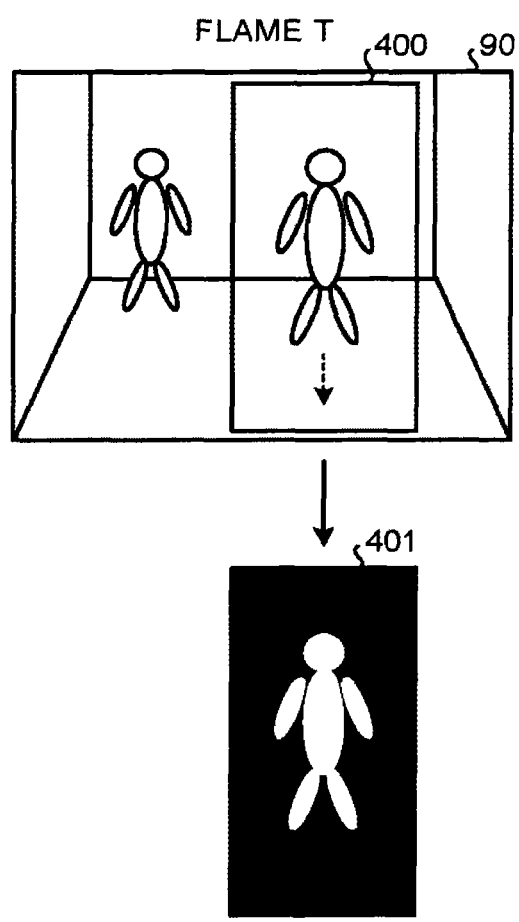
FIG. 42 is a view for describing processing in which extracting circuitry according to a sixth embodiment extracts an object region.

FIG. 42 is a view for describing processing in which the extracting circuitry 1409 according to the sixth embodiment extracts an object region. In FIG. 42, a depth image 90 in a frame T and a binary image in a frame T are illustrated. In this case, in the depth image 90 in the frame T, two objects are included. Here, a person on a right side in the depth image 90 is an object person to execute walking training and an arrow in a broken line indicates a traveling direction of the object person. Also, a person on a left side in the depth image 90 is a helper.

As illustrated in FIG. 42, the extracting circuitry 1409 receives, from the operator, a designation operation to designate a region 400 including an object person in the depth image 90 in the frame T. When the designation operation is received, the extracting circuitry 1409 extracts an object region 93 of the object person based on a pixel included in the region 400 in the depth image 90 in the frame T and a pixel included in a region 400 of a depth image 90 in a frame different from the frame T.

For example, in a case of extracting the object region 93 by the above-described first extraction processing, the extracting circuitry 1409 subtracts a depth of each pixel included in a region 400 in a depth image 90 in a frame T−1 from the depth of each pixel included in the region 400 in the depth image 90 in the frame T. Then, the extracting circuitry 1409 generates a binary image 401 corresponding to the region 400 in the depth image 90 in the frame T by performing binarization with a pixel in which the subtracted value is equal to or larger than a threshold in white and a pixel smaller than the threshold in black. Then, the extracting circuitry 1409 extracts the object region 93 of the object person by performing noise removing processing with respect to the generated binary image 401.

Note that here a case where the extracting circuitry 1409 according to the sixth embodiment extracts an object region 93 by the first extraction processing has been described. However, this is not the limitation and the object region 93 may be extracted by the above-described second or third extraction processing.

In such a manner, the extracting circuitry 1409 according to the sixth embodiment receives a designation operation to designate a predetermined region in depth image information. Then, the extracting circuitry 1409 extracts an object region 93 of the object person from depth image information included in the received predetermined region. Thus, since the motion information processing apparatus 100b according to the sixth embodiment can extract the object region 93 of the object person even in a case where a person other than the object person is included in the depth image information, a walking state of the object person can be analyzed.

Seventh Embodiment

In the above, the fifth and sixth embodiments have been described. However, there are various different embodiments other than the above-described embodiments.

For example, in the above-described embodiments, a case where the calculating circuitry 1410 calculates a position of a foot by using a position of a center of gravity calculated from the object region 93 has been described but an embodiment is not limited thereto. For example, a calculating circuitry 1410 may calculate a position of a foot by using a position of a head of an object person. Also, as a different example, the calculating circuitry 1410 may calculate a position of a foot by using a quartic function. In the following, these two cases will be described.

Processing to Calculate Position of Foot by Using Position of Head of Object Person First, processing to calculate a position of a foot by using a position of a head of an object person will be described. For example, the calculating circuitry 1410 calculates, as a position of a head of the object person, the highest point in an object region 93 by using coordinate information in a right/left direction and coordinate information in an upward/downward direction of each pixel included in the object region 93. Then, the calculating circuitry 1410 calculates, as positions of feet, a position of the lowest point on a right side of the highest point in the object region 93 and a position of the lowest point on a left side of the highest point in the object region.

Figure 43:
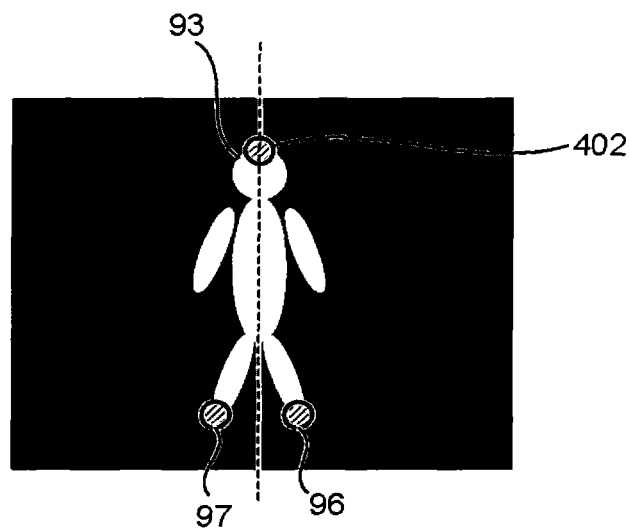
FIG. 43 is a view for describing processing performed by calculating circuitry according to a seventh embodiment.

FIG. 43 is a view for describing processing performed by the calculating circuitry 1410 according to the seventh embodiment. As illustrated in FIG. 43, the calculating circuitry 1410 calculates a position of a highest point 402 in the object region 93 from a binary image generated by an extracting circuitry 1409. Then, the calculating circuitry 1410 calculates a perpendicular which passes through the calculated highest point 402. Then, the calculating circuitry 1410 calculates, as a position of a left foot, the lowest point 96 in the object region 93 in a region in which a pixel position X is larger than the calculated perpendicular. Also, the calculating circuitry 1410 calculates, as a position of a right foot, the lowest point 97 in the object region 93 in a region in which the pixel position X is smaller than the calculated perpendicular. In such a manner, the calculating circuitry 1410 calculates a position of a foot by using a position of a head of the object person.

Processing to Calculate Position of Foot by Using Quartic Function

First, processing to calculate a position of a foot by using a position of a head of an object person will be described. For example, the calculating circuitry 1410 calculates an approximate curve of a quartic function indicating an outline of the object region 93 with respect to a region, in which coordinate information in an upward/downward direction is equal to or smaller than a threshold, in the depth image information from which the object region 93 is extracted. Then, the calculating circuitry 1410 calculates, as positions of feet, positions of two minimum values in the calculated approximate curve.

Figure 44:
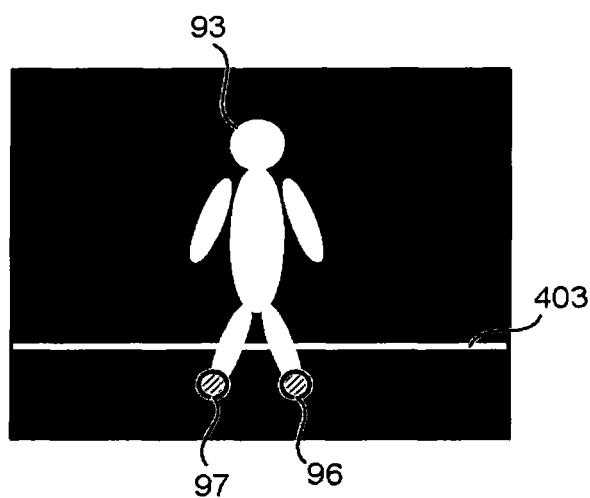
FIG. 44 is a view for describing processing performed by the calculating circuitry according to the seventh embodiment.

FIG. 44 is a view for describing processing performed by the calculating circuitry 1410 according to the seventh embodiment. As illustrated in FIG. 44, the calculating circuitry 1410 sets a horizontal line 403 at a predetermined height with respect to the binary image generated by the extracting circuitry 1409. Then, the calculating circuitry 1410 calculates an equation of a curved line formed by the outline of the object region 93 and the horizontal line 403 with respect to a region lower than the horizontal line 403. More specifically, in a region lower than the horizontal line 403 in the binary image, a curved line indicating a boundary between a white pixel and a black pixel is approximate to the quartic function. Thus, the calculating circuitry 1410 calculates an equation of the approximate curve of the quartic function. Then, the calculating circuitry 1410 calculates, as positions of feet of the object person, two minimum values in the approximate curve of the quartic function. In this case, the calculating circuitry 1410 calculates, with respect to the two minimum points, one with a larger value of an x coordinate as a position of a left foot 96 and one with a smaller value of an x coordinate as a position of a right foot 97. In such a manner, the calculating circuitry 1410 calculates positions of the feet by using the quartic function.

Case where Object Person Uses Walking Supporting Device

Also, in the above-described embodiment, a case where an object person does not use a walking supporting device such as a stick has been described. However, there is a case where the object person uses a walking supporting device such as a stick. In this case, with a configuration described in the following, the motion information processing apparatus 100*b* calculates a position of a foot accurately without erroneously recognizing a lowest point of the walking supporting device as a position of the foot.

For example, by removing a walking supporting device from the binary image 92 by using the above-described noise removing processing, the extracting circuitry 1409 extracts an object region 93 not including the walking supporting device. More specifically, the extracting circuitry 1409 removes the walking supporting device from the binary image 92 by executing the predetermined number of times of contraction processing and executing expansion processing for the same number of times thereafter according to a depth of the extracted object region 93.

FIG. 45 is a view illustrating an example of correspondence information stored in storage circuitry 130*b* according to the seventh embodiment. As illustrated in FIG. 45, the storage circuitry 130*b* stores correspondence information in which a depth (m) and the number of times are associated to each other. Here, the depth (m) indicates a depth from motion information collecting circuitry 10 to the object region 93. Also, the number of times indicates the number of times of each of the contraction processing and the expansion processing corresponding to the depth of the object region 93.

As illustrated in FIG. 45, the storage circuitry 130*b* stores information in which a depth (m) "0 to 4" and the number of times "4" are associated to each other. That is, the storage circuitry 130*b* stores that the expansion processing is to be executed for four times after the contraction processing is executed for four times when the depth of the object region 93 is zero to four meters. Note that as illustrated in FIG. 45 as an example, the number of times of the contraction processing and the expansion processing is decreased as the depth becomes deeper since a region of the walking supporting device in the binary image 92 becomes smaller as the depth becomes deeper.

Figure 46:
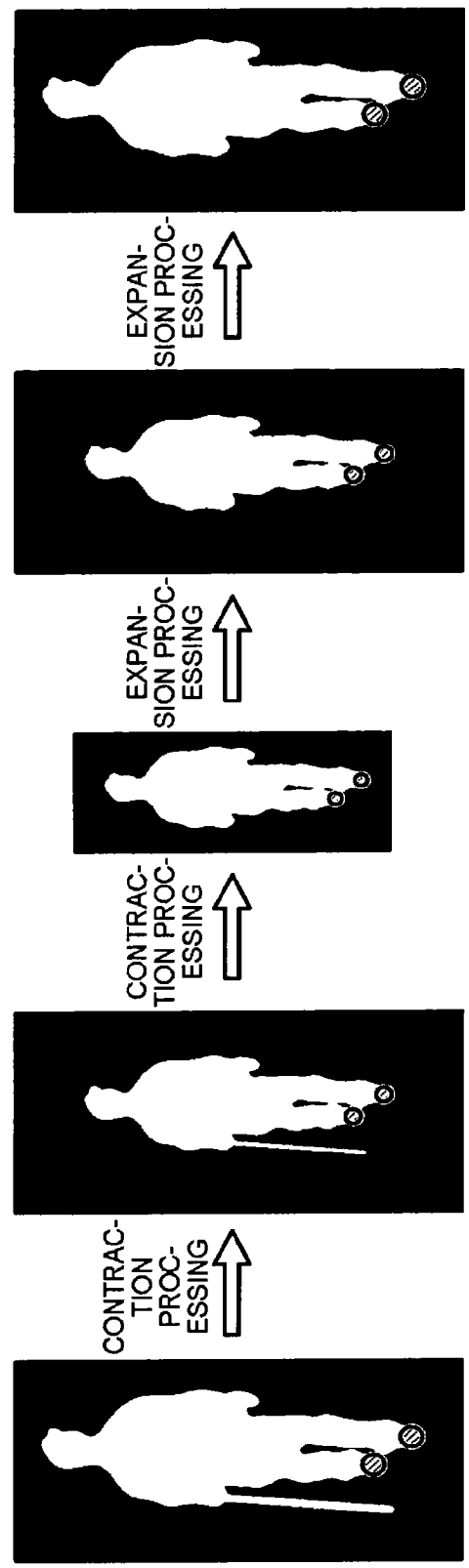
FIG. 46 is a view for describing processing performed by extracting circuitry according to the seventh embodiment.

FIG. 46 is a view for describing processing performed by the extracting circuitry 1409 according to the seventh embodiment. In FIG. 46, an example of a binary image 92 of an object person using a stick as a walking supporting device is illustrated. As illustrated in FIG. 46, the extracting circuitry 1409 extracts the object region 93 by the above-described processing. Then, the extracting circuitry 1409 acquires a z coordinate corresponding to the highest point in the object region 93 from the depth image 90. Then, the extracting circuitry 1409 refers to the correspondence information stored in the storage circuitry 130*b* and acquires the number of times corresponding to a value of the acquired z coordinate. Here, for example, when the z coordinate is 10 meters, the extracting circuitry 1409 acquires the number of times "2" from the correspondence information in the storage circuitry 130*b*. Then, after executing the contraction processing twice, the extracting circuitry 1409 executes the expansion processing twice with respect to the binary image 92 from which the object region 93 is extracted. As a result, the extracting circuitry 1409 removes the walking supporting device from the binary image 92. That is, since the calculating circuitry 1410 calculates a position of a foot of the object person by using the binary image 92 from which the walking supporting device is removed by the extracting circuitry 1409, it is possible to accurately calculate the position of the foot without erroneously recognizing the lowest point of the walking supporting device as the position of the foot.

Eighth Embodiment

In the above, the first to seventh embodiments have been described. However, there are various different embodiments other than the above-described first to seventh embodiments.

In the above-described first and second embodiments, a case where the motion information processing apparatus 100 acquires motion information of an object person executing walking training and displays display information has been described. However, an embodiment is not limited to this. For example, there may be a case where each kind of processing is executed by a service providing apparatus on a network.

Figure 47:
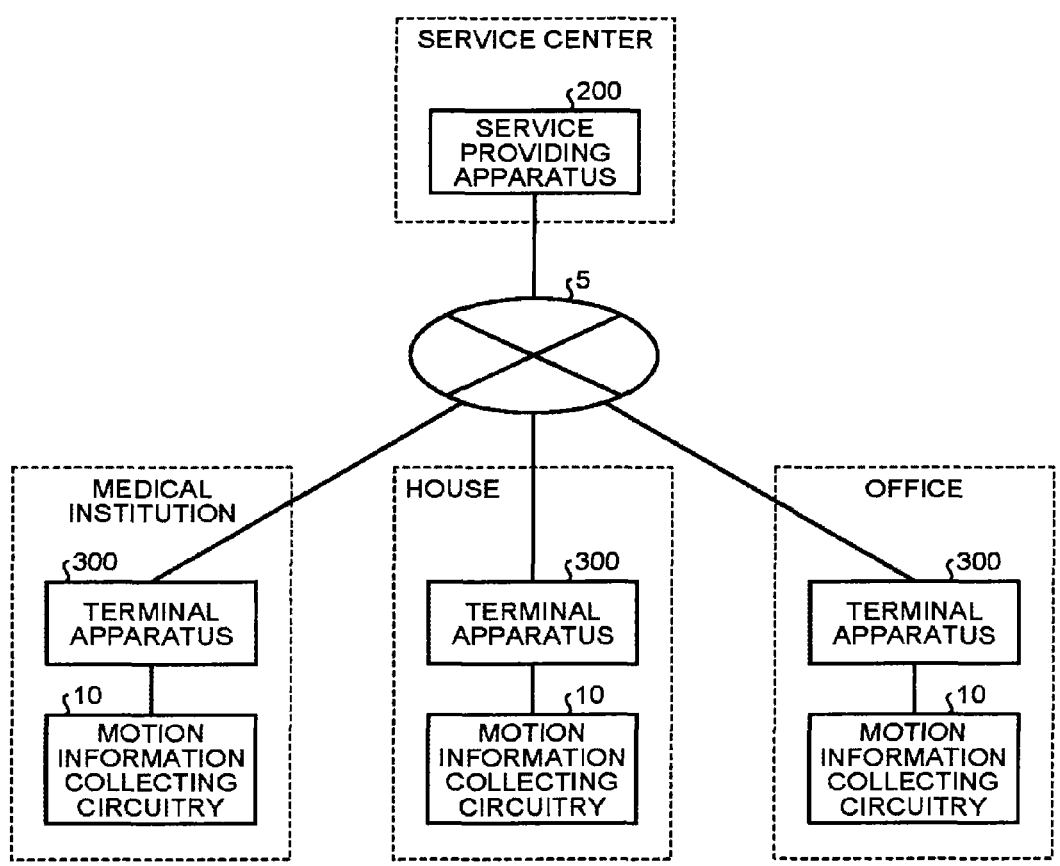
FIG. 47 is a view for describing an example of application to a service providing apparatus according to an eighth embodiment.

FIG. 47 is a view for describing an example of application to a service providing apparatus according to the eighth embodiment. As illustrated in FIG. 47, a service providing apparatus 200 is arranged in a service center and is connected, for example, through a network 5 to a terminal apparatus 300 arranged in each of a medical institution, a house, or an office. To the terminal apparatus 300 arranged in each of the medical institution, the house, and the office, motion information collecting circuitry 10 is connected. Then, each terminal apparatus 300 includes a client function which uses a service provided by the service providing apparatus 200.

To the terminal apparatus 300, the service providing apparatus 200 provides, as a service, processing similar to that by the motion information processing apparatus 100. That is, the service providing apparatus 200 includes a function circuitry similar to each of the obtaining circuitry 1401, the generating circuitry 1403, and the display controlling circuitry 1404. Then, the function circuitry similar to the obtaining circuitry 1401 obtains motion information of an object person who executes a walking motion. Then, based on the motion information obtained by the function circuitry similar to the obtaining circuitry 1401, the function circuitry similar to the generating circuitry 1403 generates track information in which a position of a landing point of a foot of the object person and a track of a movement of the object person are indicated on a plane surface. Then, the function circuitry similar to the display controlling circuitry 1404 displays, on a monitor of the terminal apparatus 300, the display information generated by the function circuitry similar to the generating circuitry 1403. Note that as the network 5, an arbitrary kind of wired or wireless communication network such as the Internet or a wide area network (WAN) can be employed.

Accordingly, for example, contents photographed or recorded in a house or an office can be managed in a service center and a doctor or the like can remotely make a diagnosis in a medical institution while referring to a video (such as superimposed image information) or quantitative data (such as analysis result). That is, the present embodiment can be applied, for example, to "to observe a motor function, a blood pressure, a pulse, or the like through an information communication device such as a video phone and to give continuous advice/instruction necessary for care for a cerebral vascular disease with respect to a home-care cerebral vascular disease patient" which is described with respect to a "home-care cerebral vascular disease patient" in the "telemedicine act amendment."

Also, a configuration of the motion information processing apparatus 100 in each of the above-described first and second embodiments is just an example. Integration and separation of parts can be arbitrarily performed. For example, the analysis information storage circuitry 1302 and the display information storage circuitry 1303 can be integrated or the generating circuitry 1403 can be separated into a track information generating circuitry to generate track information and an image information generating circuitry to generate image information.

Also, in the above-described third and fourth embodiments, a case where the motion information processing apparatus 100a analyzes a walking condition by acquiring motion information of an object person who executes walking training has been described. However, an embodiment is not limited to this. For example, there may be a case where each kind of processing is executed by a service providing apparatus on a network.

For example, to the terminal apparatus 300, the service providing apparatus 200 illustrated in FIG. 47 provides, as a service, processing similar to that by the motion information processing apparatus 100a illustrated in FIG. 23. That is, the service providing apparatus 200 includes function circuitry similar to each of the obtaining circuitry 1405, the analyzing circuitry 1406, and the display controlling circuitry 1407. Then, the function circuitry similar to the obtaining circuitry 1405 obtains motion information of an object person who executes a walking motion. Then, based on a temporal change in a position of a predetermined part of the object person in the motion information obtained by the obtaining circuitry 1405, the function circuitry similar to the analyzing circuitry 1406 analyzes a walking state including a position of a landing point of a foot of the object person. Then, the function circuitry similar to the display controlling circuitry 1407 displays, on a monitor of the terminal apparatus 300, the analysis information generated by the function similar to the analyzing circuitry 1406. Note that as the network 5, an arbitrary kind of wired or wireless communication network such as the Internet or a wide area network (WAN) can be employed.

Also, a configuration of the motion information processing apparatus 100a in each of the above-described third and fourth embodiments is just an example. Integration and separation of parts can be arbitrarily performed. For example, the motion information storage circuitry 1304 and the analysis information storage circuitry 1305 can be integrated or the analyzing circuitry 1406 can be separated into calculating circuitry to calculate a position of a landing point of a foot and determination circuitry to determine whether walking is stable.

Also, for example, in the above-described fifth to seventh embodiments, a case where a clinically useful gait analysis of motion information collected by the motion information collecting circuitry 10 is performed by the motion information processing apparatus 100b has been described. However, an embodiment is not limited to this. For example, each kind of processing may be executed by a service providing apparatus on a network.

For example, the service providing apparatus 200 illustrated in FIG. 47 includes a function similar to that of the motion information processing apparatus 100b described in FIG. 32 and provides a service to the terminal apparatus 300 by the function. That is, the service providing apparatus 200 includes function circuitry similar to each of the obtaining circuitry 1408, the extracting circuitry 1409, the calculating circuitry 1410, and the analyzing circuitry 1411. Then, the function circuitry similar to the obtaining circuitry 1408 obtains a frame group which includes depth image information, in which each pixel included in a photographing range and a depth of each pixel are associated to each other, in each frame and which is lined up in time-series. Then, based on depth image information in a frame to be processed and depth image information in a different frame from the depth image information, the function circuitry similar to the extracting circuitry 1409 extracts, from the depth image information in the frame to be processed, an object region indicating a region of an object in a three-dimensional space. Then, the function circuitry similar to the calculating circuitry 1410 calculates a position of a foot of the object from the object region. For example, the calculating circuitry 1410 calculates a position of a center of gravity of the object region 93 by using coordinate information in a right/left direction of each pixel included in the object region 93 and coordinate information in an upward/downward direction thereof. Then, the function circuitry similar to the analyzing circuitry 1411 analyzes a walking state based on a temporal change in a position of a foot. From what has been described above, the service providing apparatus 200 can analyze a walking motion easily.

For example, the service providing apparatus 200 receives, from the terminal apparatus 300, an upload of a frame group of depth image information to be processed. Then, the service providing apparatus 200 analyzes a walking state by performing the above-described processing. Then, the service providing apparatus 200 downloads analysis information into the terminal apparatus 300.

Also, a configuration of the motion information processing apparatus 100b in each of the above-described fifth to seventh embodiments is just an example. Integration and separation of parts can be arbitrarily performed. For example, the obtaining circuitry 1408 and the extracting circuitry 1409 can be integrated.

Also, a function of each of the obtaining circuitry 1401, the analyzing circuitry 1402, the generating circuitry 1403, and the display controlling circuitry 1404 described in each of the above-described first and second embodiments, the obtaining circuitry 1405, the analyzing circuitry 1406, and the display controlling circuitry 1407 described in each of the third and fourth embodiments, and the obtaining circuitry 1408, the extracting circuitry 1409, the calculating circuitry 1410, and the analyzing circuitry 1411 described in each of the fifth to seventh embodiments can be realized by software. For example, a function of each part is realized by making a computer execute a motion information processing program in which a procedure of processing described as what is to be performed by each circuitry in each of the above-described embodiments is prescribed. For example, the motion information processing program is stored in a hard disk, a semiconductor memory element, or the like and is read and executed by a processor such as a CPU or an MPU. Also, the motion information processing program can be recorded in a computer-readable recording medium such as a compact disc-read only memory (CD-ROM), a magnetic optical disk (MO), or a digital versatile disc (DVD) when being distributed.

Note that an angle of a part, a basis, or the like analyzed in each of the above-described first to seventh embodiments is not limited to what is prescribed in The Japan Orthopaedic Association or the like. There may be a case where what is prescribed in a different organization is used. For example, there may be a case where an angle of a part, a basis, or the like prescribed in the "International Society of Orthopaedic Surgery and Traumatology (SICOT)," the "American Academy of Orthopaedic Surgeons (AAOS)," the "European Orthopaedic Research Society (EORS)," the "International Society of Physical and Rehabilitation Medicine (ISPRM)," or the "American Academy of Physical Medicine and Rehabilitation (AAPM&R)" is used.

As described above, according to each of the first to eighth embodiments, a motion information processing apparatus and a program of the present embodiment make it possible to provide display information with which a walking condition can be easily evaluated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A motion information processing apparatus comprising:
processing circuitry configured to
obtain motion information of an object person who executes a walking motion;
generate track information, in which a relative position of landing points of both feet of the object person and a relative position between the landing points of the both feet and a movement track of a feature position of the object person are indicated, based on the motion information obtained; and
perform control in such a manner that the track information generated is displayed on a display.

2. The motion information processing apparatus according to claim 1, wherein the processing circuitry is configured to generate track information further indicating an angle of a predetermined part of a body of the object person.

3. The motion information processing apparatus according to claim 2, wherein an angle of the predetermined part is at least one of a rotation angle indicating forward/backward shaking in a traveling direction of the object person and a rotation angle indicating shaking in an upward/downward direction of the object person.

4. The motion information processing apparatus according to claim 1, wherein
the feature position is at least one of a position of a predetermined part of the object person, a position calculated by using positions of a plurality of parts, a plurality of center positions of the object person, and a position of a center of gravity of the object person.

5. The motion information processing apparatus according to claim 1, wherein the processing circuitry is configured to generate information included in the track information in a predetermined format in such a manner that identification thereof becomes possible.

6. The motion information processing apparatus according to claim 1, wherein the processing circuitry is further configured to
receive a selection operation to select information to be displayed on the display from pieces of information included in the track information generated, and perform control in such a manner that the information selected by the selection operation received is displayed on the display.

7. The motion information processing apparatus according to claim 1, wherein the processing circuitry is configured to
further obtain image information of when the object person executes the walking motion, and
perform control in such a manner that the track information generated and image information obtained are displayed on the display.

8. The motion information processing apparatus according to claim 7, wherein the processing circuitry is configured to
generate superimposed image information in which information of an angle between a predetermined basis and a predetermined part of the object person is superimposed on an object person drawn onto the image information obtained, and
perform control in such a manner that the track information and the superimposed image information generated are displayed on the display.

9. The motion information processing apparatus according to claim 1, the processing circuitry is further configured to
analyze whether a walking motion corresponding to the motion information obtained is walking which satisfies a predetermined basis,
when the walking motion does not satisfy the predetermined basis, execute a warning display on track information corresponding to a walking motion determined to be the walking motion which does not satisfy the predetermined basis.

10. The motion information processing apparatus according to claim 1, wherein the processing circuitry is configured to
analyze predetermined analysis information according to a walking motion corresponding to the motion information obtained,
generate display information including an analysis result of the analysis information analyzed, and
perform control in such a manner that the display information which includes the analysis result and which is generated is displayed on the display.

11. A motion information processing apparatus comprising:
processing circuitry configured to
obtain motion information and image information of an object person who executes a walking motion;
calculate at least one of an angle between a reference in a space where the object person executes the walking motion and a predetermined part of a body of the object person and an angle between a reference part of the body and a predetermined part of a body;
generate superimposed image information in which information of the angle calculated is superimposed on the image information obtained; and
perform control in such a manner that the superimposed image information generated is displayed on a display.

12. The motion information processing apparatus according to claim 11, wherein the processing circuitry is configured to
generate track information, in which a position of a landing point of a foot of the object person and a track of a movement of the object person are indicated on a plane view, based on the motion information obtained, and display the track information, which is generated, on the display in addition to the superimposed image information.

13. A motion information processing apparatus comprising:
processing circuitry configured to
obtain motion information of an object person who executes a walking motion;
generate graph information, which indicates a relative position of landing points of both feet of the object person on a graph with one axis as a position of the object person and the other axis as time in the walking motion, based on the motion information obtained; and
perform control in such a manner that the graph information generated is displayed on a display.

14. A method comprising:
acquiring motion information of an object person who executes a walking motion;
generating track information, in which a relative position of landing points of both feet of the object person and a relative position between the landing points of the both feet and a movement track of a feature position of the object person are indicated, based on the obtained motion information; and
displaying the generated track information on a display.

15. A motion information processing apparatus comprising processing circuitry configured to
obtain motion information of an object person who executes a walking motion;
generate track information, in which a position of a landing point of a foot of the object person and a track of a movement of the object person are indicated, based on the motion information obtained;
perform control in such a manner that the track information generated is displayed on a display; and
analyze a walking state, which includes a position where the foot of the object person touches a ground, based on a temporal change in a position of a predetermined part of the object person in the motion information obtained, wherein
the processing circuitry is configured to determine whether the foot of the object person is on the ground based on a temporal and three-dimensional change in the position of the predetermined part of the object person in the motion information obtained and set a position of the foot of the object person at a time point of determination as the landing point when it is determined that the foot is on the ground.

16. The motion information processing apparatus according to claim 15, wherein the processing circuitry is configured to determine landing of the foot of the object person based on a change amount in a unit time of a position of a predetermined part in the foot of the object person.

17. The motion information processing apparatus according to claim 16, wherein the processing circuitry is configured to analyze a change amount in the unit time of the position of the predetermined part in a traveling direction of walking by the object person, a body axis direction, or a direction orthogonal to the traveling direction.

18. The motion information processing apparatus according to claim 17, wherein the processing circuitry is configured to calculate the traveling direction based on a change in a value of the position along with walking by the object person.

19. The motion information processing apparatus according to claim 16, wherein the processing circuitry is configured to analyze a change amount in the unit time of the position of the predetermined part in at least two of the traveling direction, the body axis direction, and the direction orthogonal to the traveling direction.

20. The motion information processing apparatus according to claim 15, wherein the processing circuitry is configured to determine, based on a change amount of a position of a predetermined part in one foot of the object person, landing of an opposite foot of the one foot.

21. The motion information processing apparatus according to claim 15, wherein the processing circuitry is configured to further calculate, as the walking state, an angle between a predetermined basis and the predetermined part of the object person.

22. The motion information processing apparatus according to claim 15, wherein the processing circuitry is configured to analyze a position of a landing point of the foot of the object person based on a unique motion or instrument of the object person which motion or instrument is included in the motion information of the object person who executes the walking motion, the motion information being obtained.

23. The motion information processing apparatus according to claim 15, wherein the processing circuitry is configured to predict a landing point of the foot of the object person based on an analyzed position of a landing point of the foot of the object person and a temporal change in the position of the predetermined part of the object person.

24. The motion information processing apparatus according to claim 15, wherein the processing circuitry is configured to perform control in such a manner that the walking information analyzed is displayed on the display.

25. A motion information processing apparatus comprising processing circuitry configured to
obtain motion information of an object person who executes a walking motion;
generate track information, in which a position of a landing point of a foot of the object person and a track of a movement of the object person are indicated, based on the motion information obtained; and
perform control in such a manner that the track information generated is displayed on a display, wherein
the processing circuitry is further configured to
extract an object region which is in a three-dimensional space and which indicates a region of an object to be analyzed, in a frame group which is in time series and which includes, in each frame, depth image information in which each pixel included in a photographing range and a depth of the pixel are associated to each other, from depth image information in a frame to be processed based on the depth image information in the frame to be processed and depth image information in a different frame from the depth image information,
calculate a position of the foot of the object from the object region,
analyze a walking state based on a temporal change in the position of the foot, and
acquire the frame group.

26. The motion information processing apparatus according to claim 25, wherein the processing circuitry is configured to analyze, as the walking state, a position where the foot of the object touches a ground.

27. The motion information processing apparatus according to claim 25, wherein the processing circuitry is configured to calculate, in the frame group, a difference between a depth of each pixel in the depth image information in the frame to be processed and that in depth image information in a frame next to the frame in time series and extract, as the object region, a region of a pixel in which the calculated difference is equal to or larger than a threshold.

28. The motion information processing apparatus according to claim 25, wherein the processing circuitry is configured to calculate, in the frame group, a difference between a depth of each pixel in the depth image information in the frame to be processed and that in depth image information in a frame in which no object is included in the photographing range and extract, as the object region, a region of a pixel in which the calculated difference is equal to or larger than a threshold.

29. The motion information processing apparatus according to claim 25, wherein the processing circuitry is configured to calculate, in the frame group, a difference between a depth of each pixel in the depth image information in the frame to be processed and that in depth image information in a frame before the frame for a predetermined period of time and extract, as the object region, a region of a pixel in which the calculated difference is equal to or larger than a threshold.

30. The motion information processing apparatus according to claim 25, wherein the processing circuitry is configured to calculate a position of a center of gravity of the object region or a highest point in the object region based on coordinate information in a right/left direction of each pixel included in the object region and coordinate information in an upward/downward direction thereof and calculate, as positions of feet, a position of a lowest point on a right side of the position in the object region and a position of a lowest point on a left side of the position of the center of gravity in the object region.

31. The motion information processing apparatus according to claim 25, wherein the processing circuitry is configured to calculate an approximate curve of a quartic function indicating an outline of the object region in a region in which coordinate information in an upward/downward direction is equal to or smaller than a threshold in the depth image information from which the object region is extracted and calculate, as positions of feet, two minimum positions in the calculated approximate curve.

32. The motion information processing apparatus according to claim 25, wherein the processing circuitry is configured to receive a designation operation to designate a predetermined region in the depth image information and extract the object region from depth image information included in the received predetermined region.

* * * * *